United States Patent
Lin et al.

(10) Patent No.: US 10,519,440 B2
(45) Date of Patent: Dec. 31, 2019

(54) COMPOSITION AND METHOD OF USING MIR-302 PRECURSORS AS DRUGS FOR TREATING ALZHEIMER'S DISEASES

(71) Applicant: Mello Biotechnology, Inc., Santa Fe Springs, CA (US)

(72) Inventors: Chih-Li Lin, Taichung (TW);
Hsin-Hua Li, Taichung (TW);
Shi-Lung Lin, Arcadia, CA (US);
Te-Jen Lai, Taichung (TW)

( * ) Notice: Subject to any disclaimer, the term of this patent is extended or adjusted under 35 U.S.C. 154(b) by 408 days.

(21) Appl. No.: 15/048,964

(22) Filed: Feb. 19, 2016

(65) Prior Publication Data
US 2017/0218362 A1    Aug. 3, 2017

Related U.S. Application Data

(60) Continuation-in-part of application No. 14/527,439, filed on Oct. 29, 2014, now Pat. No. 9,637,747, and a continuation-in-part of application No. 14/502,608, filed on Sep. 30, 2014, now Pat. No. 9,783,811, said application No. 14/527,439 is a division of application No. 13/572,263, filed on Aug. 10, 2012, now abandoned, said application No. 14/502,608 is a division of application No. 13/572,263, filed on Aug. 10, 2012, now abandoned.

(60) Provisional application No. 62/262,280, filed on Dec. 2, 2015.

(51) Int. Cl.
| | |
|---|---|
| *C12N 15/113* | (2010.01) |
| *C12N 5/0793* | (2010.01) |
| *C12N 5/10* | (2006.01) |
| *C12N 15/63* | (2006.01) |
| *C12N 1/38* | (2006.01) |

(52) U.S. Cl.
CPC .......... *C12N 15/113* (2013.01); *C12N 5/0619* (2013.01); *C12N 5/10* (2013.01); *C12N 15/63* (2013.01); *C12N 1/38* (2013.01); *C12N 15/635* (2013.01); *C12N 2310/141* (2013.01); *C12N 2310/531* (2013.01)

(58) Field of Classification Search
CPC ........ C12N 15/113; C12N 5/093; C12N 5/10; C12N 15/63; C12N 2310/531; C12N 2310/141
USPC ............... 435/325, 320.1, 368; 536/24.1
See application file for complete search history.

(56) References Cited

PUBLICATIONS

Li et al. (2011) Nucl. Acids. Res., vol. 39, 1054-1065.*
Li et al. (2011) Stem Cells, vol. 29, 1645-1649.*

* cited by examiner

*Primary Examiner* — Anne Marie S Wehbe
(74) *Attorney, Agent, or Firm* — Procopio, Cory, Hargreaves & Savitch LLP

(57) ABSTRACT

This invention generally relates to a composition and method of using recombinant microRNAs (miRNA) and their hairpin-like precursors (pre-miRNA) as therapeutic drugs for treating Alzheimer's diseases (AD). More specifically, the present invention relates to the use of man-made miRNA miR-302 precursors (pre-miR-302) for AD therapy in humans. These pre-miR-302 molecules can be mass produced in prokaryotes as a form of DNA expression-competent DNA vectors and/or hairpin-like RNAs. As prokaryotic cells do not transcribe or process hairpin-like RNAs, the present invention also teaches a method for expressing pre-miRNAs in prokaryotes, i.e. pro-miRNA, using a novel hairpin-like RNA transcription mechanism newly found in prokaryotes. Additionally, since miR-302 is a well-known embryonic stem cell (ESC)-specific factor in humans, our novel findings of this invention can be further used to advance the designs and development of novel regenerative medicine for treating many other ageing-related degenerative diseases, such as Parkinson's diseases, osteoporosis, diabetes, and cancers.

15 Claims, 33 Drawing Sheets
(28 of 33 Drawing Sheet(s) Filed in Color)
Specification includes a Sequence Listing.

Add MOPS+glycerin (red color) — No Addition (original color)

pLVX-Grn-miR302+367 — Green
+MOPS
pLenti-EF1α-RGFP-miR302 — Red

FIG. 9A Example of control section shows large area of scare tissue underneath (190-CR3)
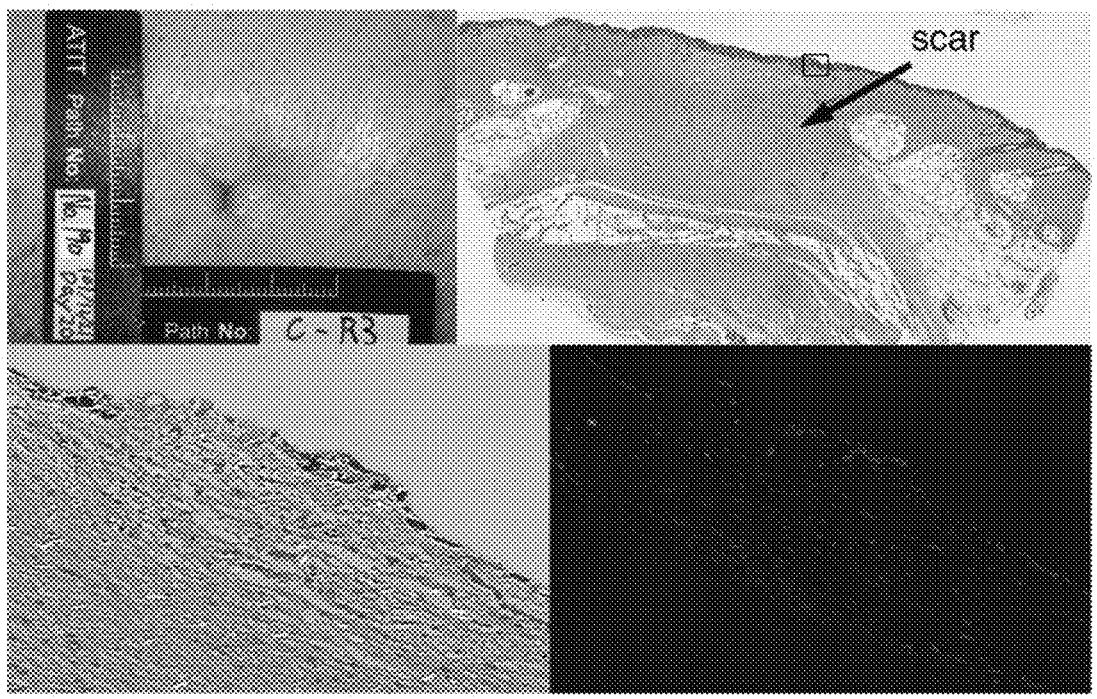
FIG. 9B Example of treated section shows no scare tissue underneath (190-BR2)
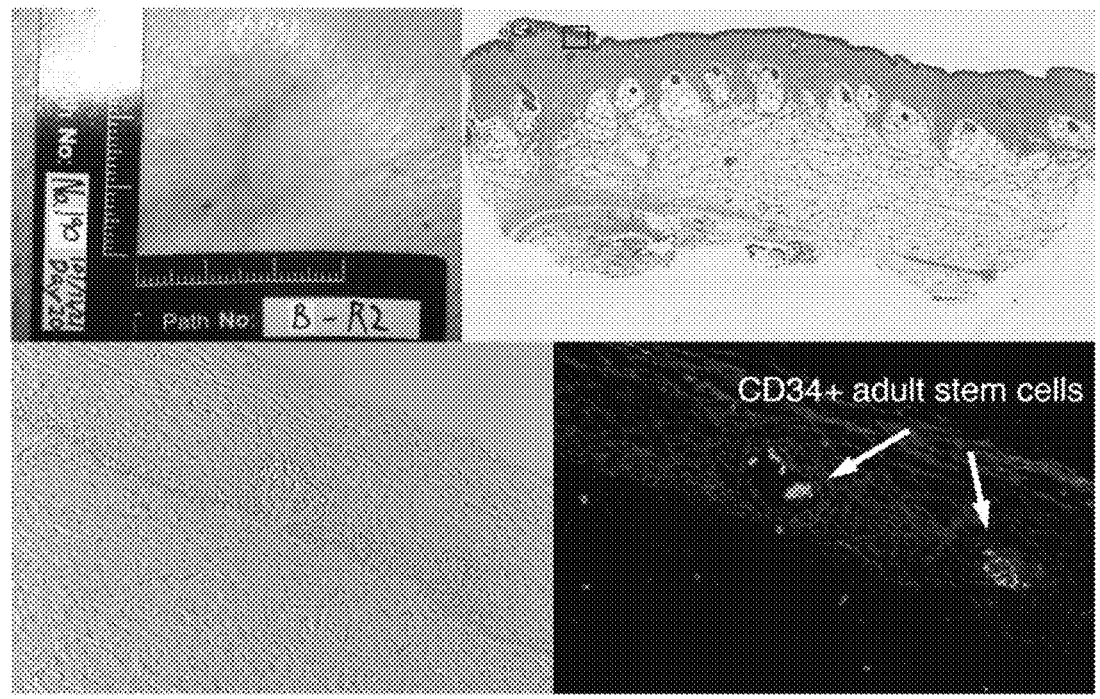

small RNAs extracted from blank *E. coli* competent cells (control):

small RNAs extracted from RGFP-miR302 transformed E. coli cells:

FIG. 12

| | | | FIG.11A | FIG.11B | |
| | | | Group 1 | Group 2 | |
| | | | #1 | #2 | |
| Rpter Index | Reporter Name | p-value | Mean | Mean | Log2 (G2/G1) |
|---|---|---|---|---|---|
| 445 | hsa-miR-302c-5p | 1.28E-03 | 0 | 52,804 | 22.65 |
| 443 | hsa-miR-302a-5p | 1.38E-03 | 0 | 26,579 | 21.85 |
| 441 | hsa-miR-302a-3p | 1.52E-03 | 0 | 66,718 | 22.92 |
| 444 | hsa-miR-302c-3p | 3.51E-03 | 0 | 15,973 | 20.71 |
| 447 | hsa-miR-302d-5p | 2.23E-02 | 3 | 22,124 | 12.87 |
| 313 | hsa-miR-302b-5p | 3.09E-02 | 1 | 940 | 3.75 |
| 442 | hsa-miR-302d-3p | 4.86E-02 | 0 | 9,579 | 18.53 |
| 591 | hsa-miR-320b-3p | 4.88E-02 | 6 | 1,963 | 2.23 |
| 131 | hsa-miR-1275 | 8.78E-02 | 749 | 364 | -1.22 |
| Following transcripts are not statistically significant due to low signals (signal < 500) | | | | | |
| 554 | hsa-miR-3177-3p | 2.06E-02 | 402 | 76 | -2.40 |
| 986 | hsa-miR-4459 | 3.59E-02 | 66 | 135 | 1.04 |
| 967 | hsa-miR-4442 | 4.52E-02 | 32 | 65 | 1.02 |
| 1298 | hsa-miR-4758-5p | 4.93E-02 | 7 | 74 | 3.45 |
| 993 | hsa-miR-4466 | 5.70E-02 | 58 | 137 | 1.23 |
| 1120 | hsa-miR-4649-5p | 5.76E-02 | 187 | 385 | 1.04 |
| 1500 | hsa-miR-5195-3p | 5.81E-02 | 49 | 316 | 2.68 |
| 851 | hsa-miR-4253 | 5.86E-02 | 296 | 136 | -1.12 |
| 299 | hsa-miR-146a-5p | 5.93E-02 | 7 | 62 | 3.21 |
| 1156 | hsa-miR-4668-5p | 7.08E-02 | 315 | 70 | -2.17 |
| 974 | hsa-miR-4447 | 7.41E-02 | 13 | 89 | 2.76 |
| 1251 | hsa-miR-4728-3p | 7.96E-02 | 42 | 16 | -1.42 |
| 750 | hsa-miR-146a-3p | 8.97E-02 | 23 | 88 | 1.92 |
| 870 | hsa-miR-4270 | 9.39E-02 | 29 | 113 | 1.95 |
| 1123 | hsa-miR-4651 | 9.46E-02 | 25 | 116 | 2.19 |

FIG. 13A

Sequence of the miR-302 Family

1 AATTTTTTTC TTCTAAAGTT ATGCCATTTT GTTTTCTTTC TCCTCAGCTC TAAATACTCT

61 GAAGTCCAAA GAAGTTGTAT GTTGGGTGG<u>G CTCCCTTCAA CTTTAACATG GAAGTGCTTT</u>   302B

121 <u>CTGTGACTTT AAAAGTAAGT GCTTCCATGT TTTAGTAGGA GTG</u>AATCCAA TTTACTTCTC

181 CAAAATAGAA CACGCTAACC TCATTTGAAG GGATCC<u>CCTT TGCTTAACA TGGGGGTACC</u>  302C

241 <u>TGCTGTGTGA AACAAAAGTA AGTGCTTCCA TGTTTCAGTG GAGGT</u>GTCTC CAAGCCAGCA

301 CACCTTTTGT TACAAAATTT TTTTGTTATT GTGTTTTAAG GTTACTAAGC TTGTTACAGG

361 TTAAAGGATT CTAACTTTTT CCAAGACTGG GCTCC<u>CCACC ACTTAAACGT GGATGTACTT</u>  302A

421 <u>GCTTTGAAAC TAAAGAAGTA AGTGCTTCCA TGTTTTGGTG ATGG</u>TAAGTC TTCTTTTTAC

481 ATTTTTATTA TTTTTTTAGA AAATAACTTT ATTGTATTGA CCGCAGCTCA TATATTTAAG

541 CTTTATTTTG TATTTTTACA TCTGTTAAGG GGCCC<u>CCTCT ACTTTAACAT GGAGGCACTT</u>  302D

601 <u>GCTGTGACAT GACAAAAATA AGTGCTTCCA TGTTTGAGTG TGG</u>TGGTTCC TACCTAATCA

661 GCAATTGAGT TAACGCCCAC ACTGTGTGCA GTTCTTGGCT ACAGGCCATT ACTGTTGCTA

FIG. 13B
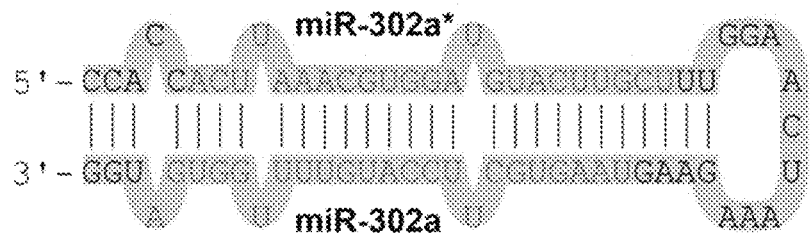
pro-miR302a
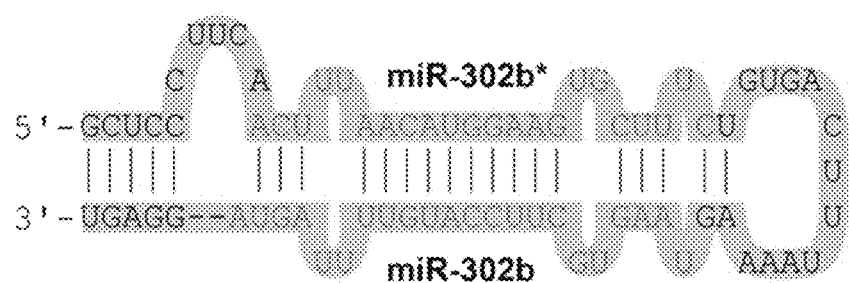
pro-miR-302b
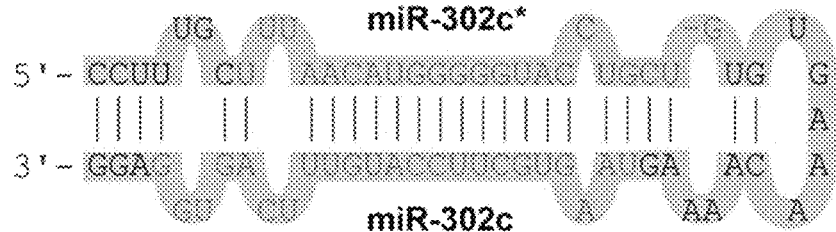
pro-miR-302c
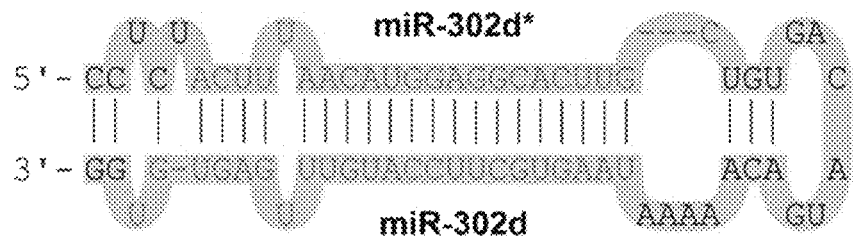
pro-miR-302d

FIG. 14E
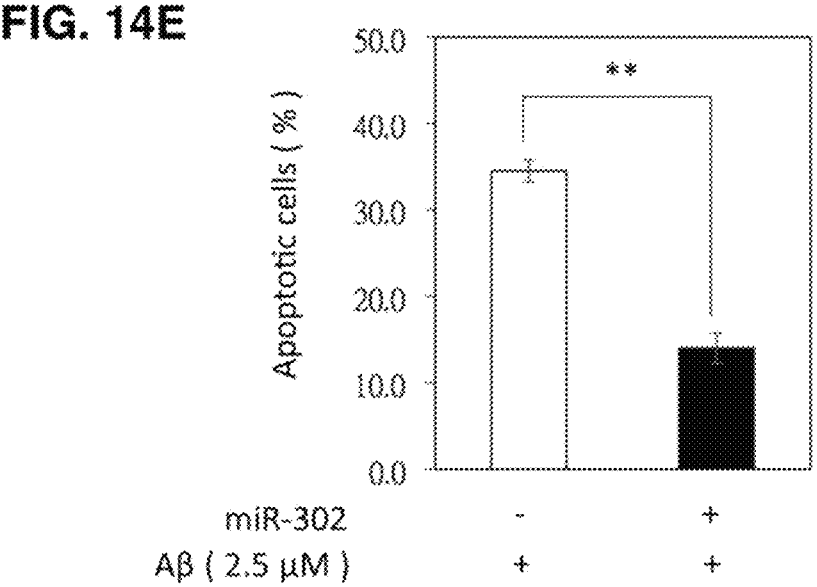
FIG. 14F
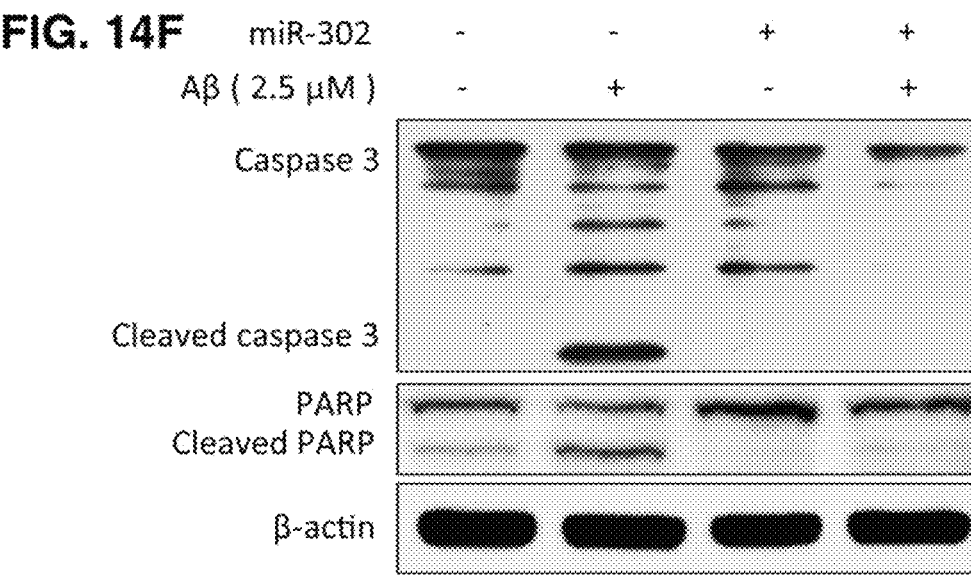
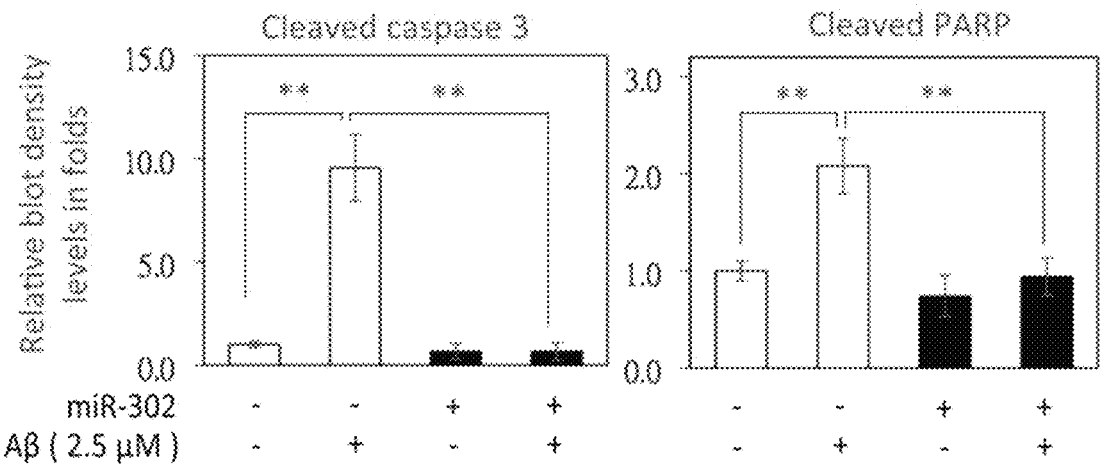

FIG. 15D
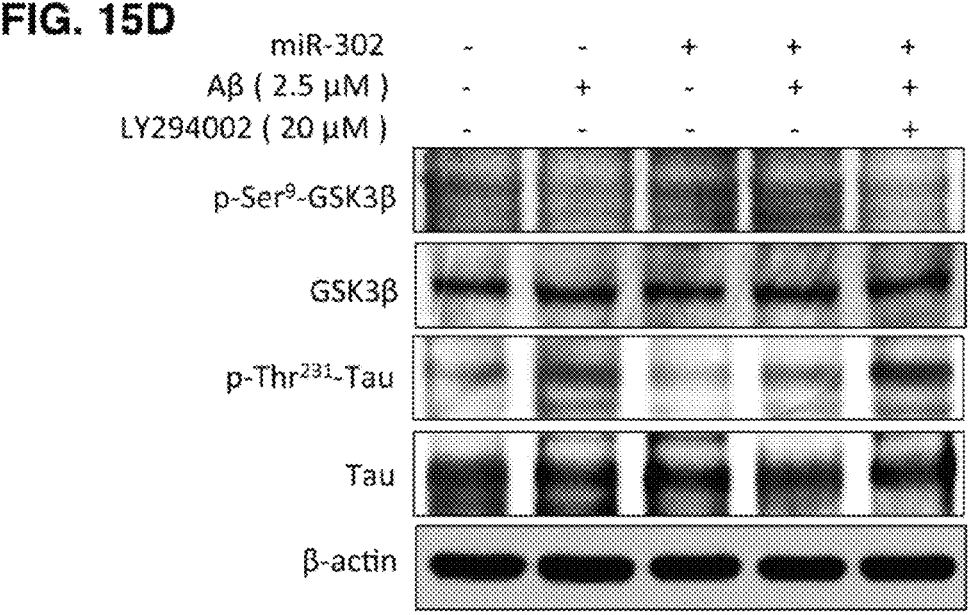
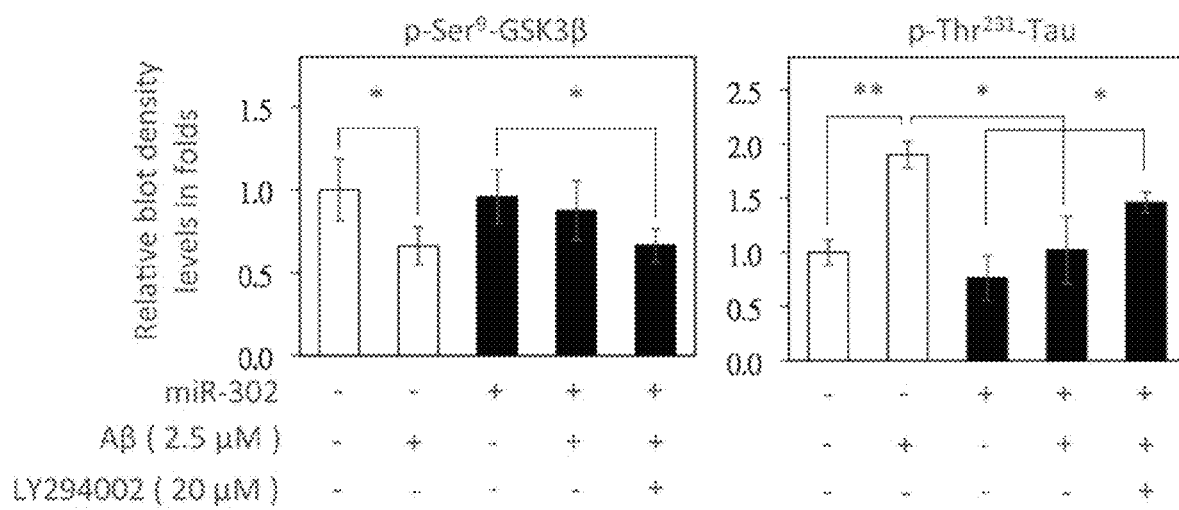

FIG. 16A
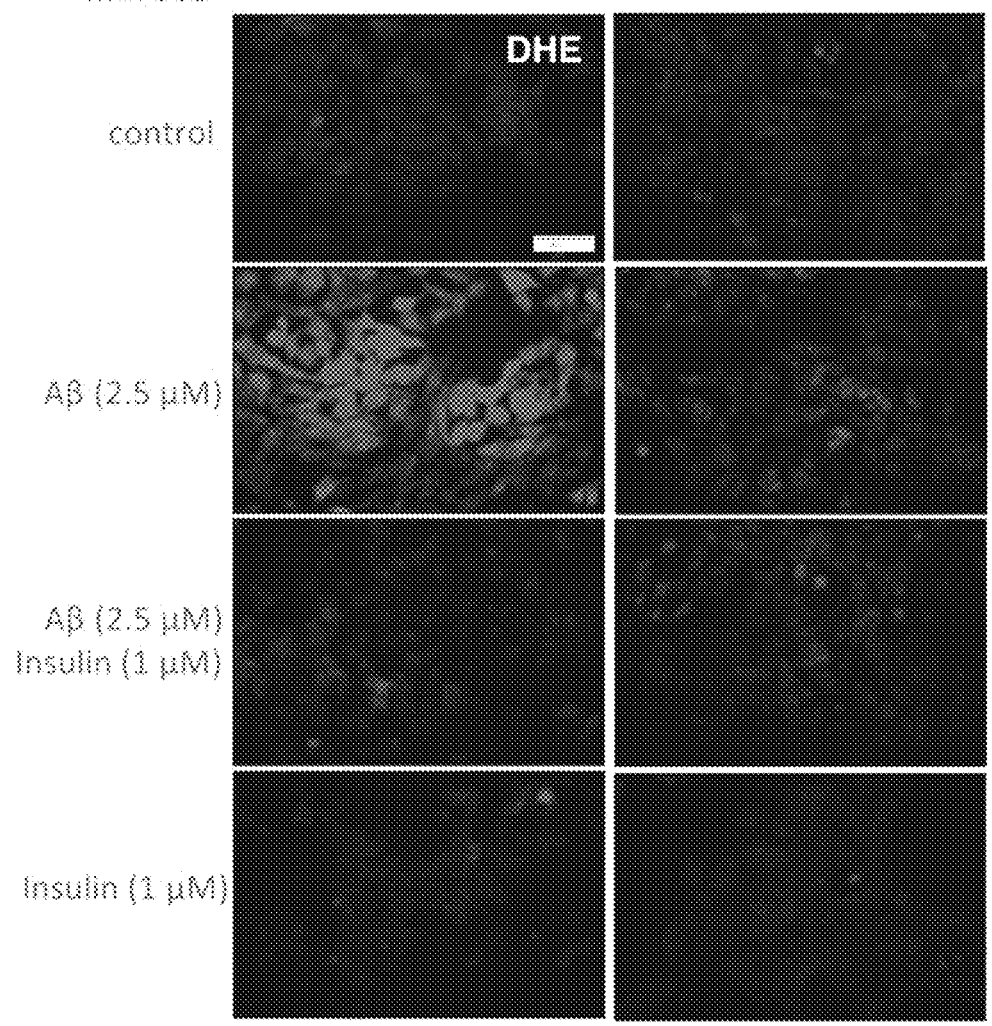
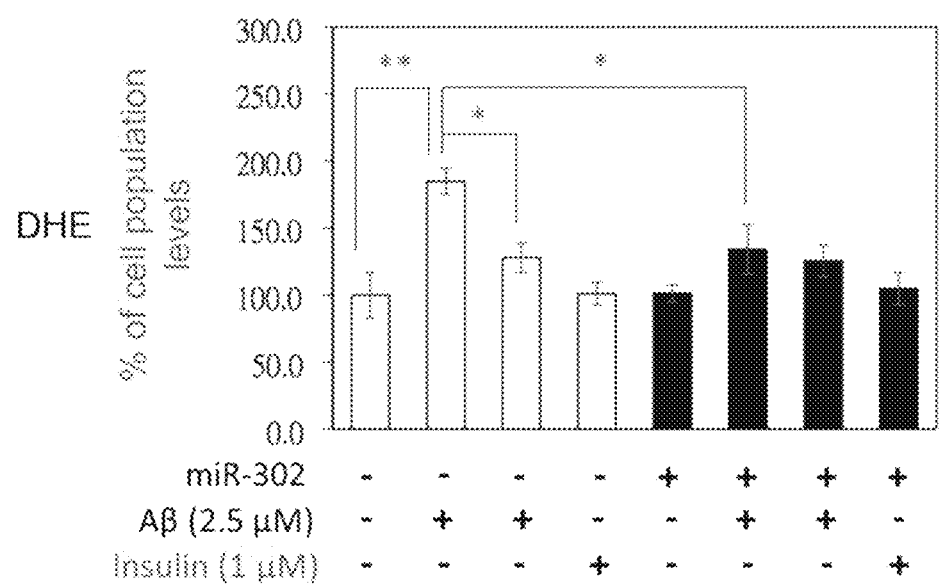

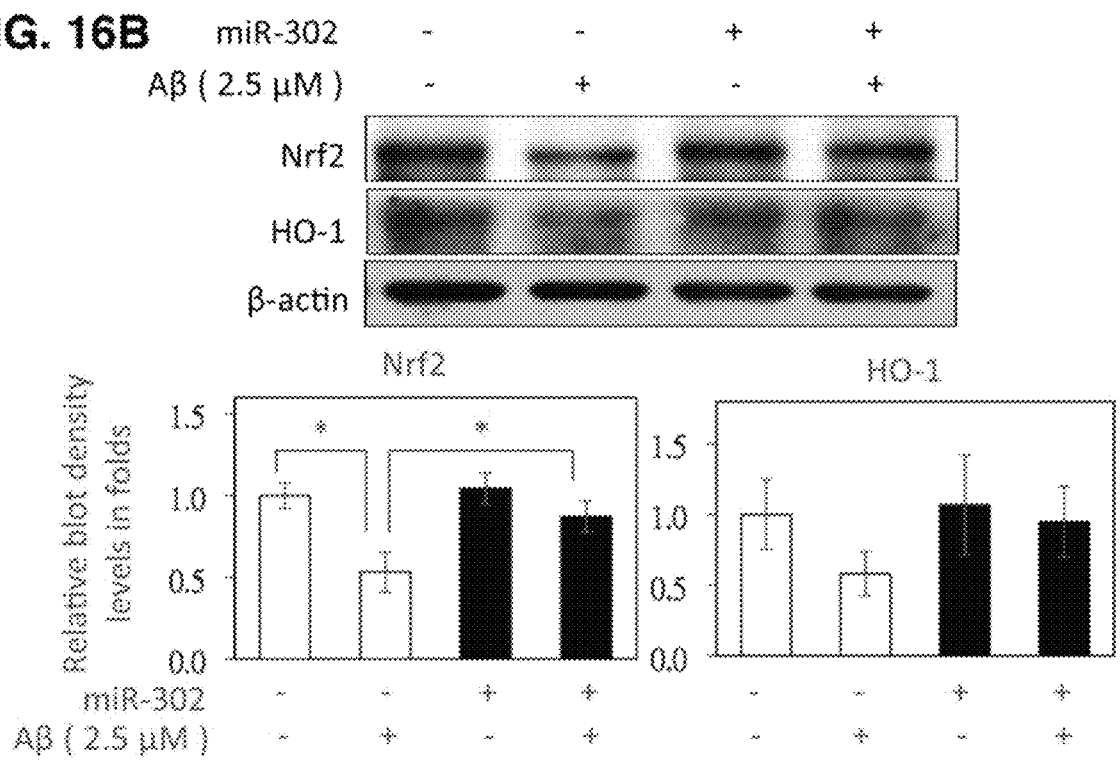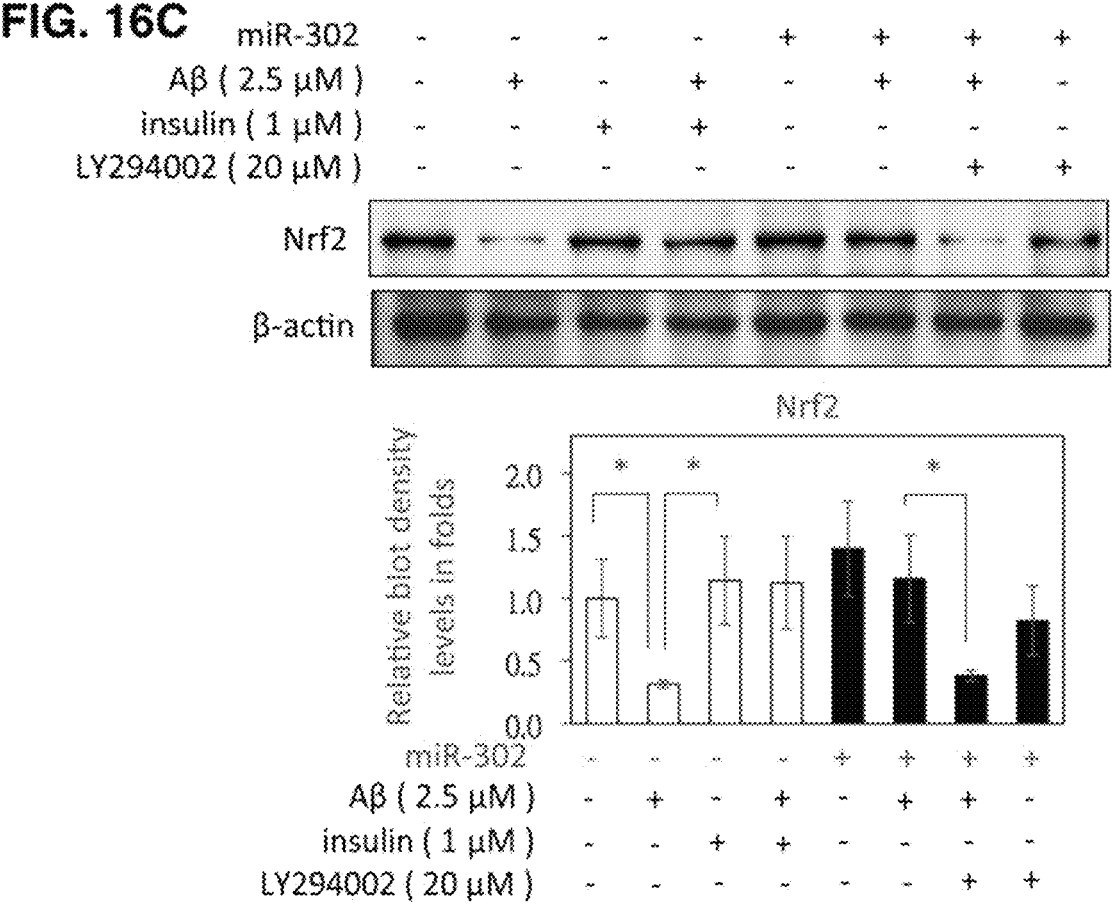

FIG. 16D
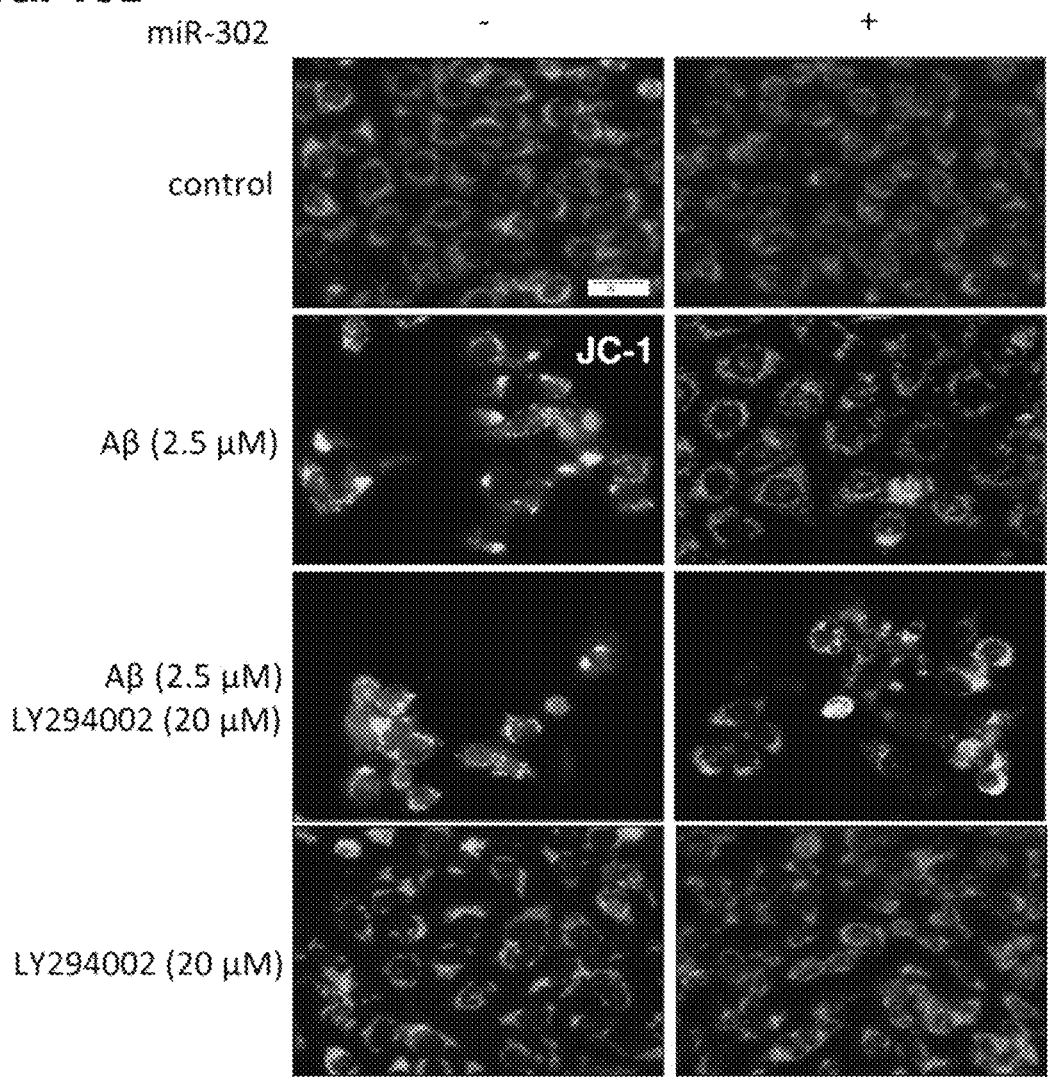
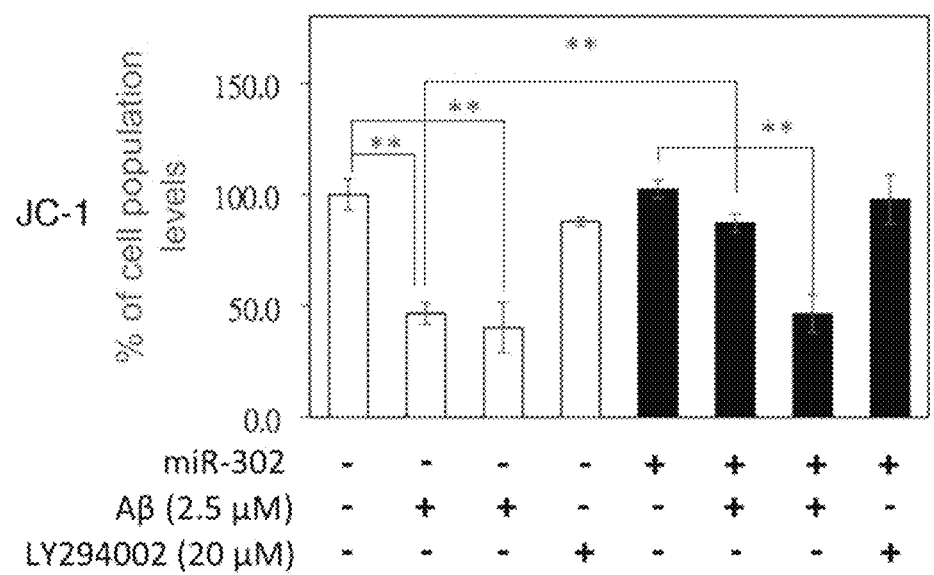

Human PTEN 3'UTR (3303 bp)

Position 277-284 of PTEN 3'UTR
Seed match: 7mer-m8

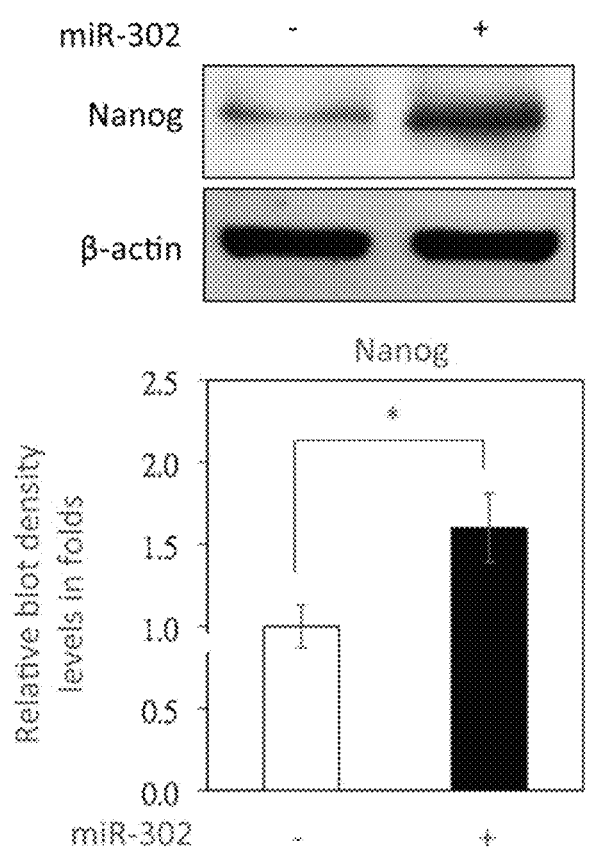

FIG. 20

Table 1. AD patients and age-matched healthy individuals included in the study. The table presents gender, age, MMSE and CASI score for AD patients and healthy controls respectively.

| Characteristics | AD* patients (n=7) | Healthy individuals (n=6) |
|---|---|---|
| Age (years) | | |
| Mean ±SD | 80.0 ± 4.9 | 80.0 ± 5.9 |
| Range | 74-86 | 72-86 |
| Gender | | |
| Female/Male | 4/3 | 3/3 |
| MMSE score | | |
| Mean ±SD | 19.3 ± 2.6 | N/A |
| Range | 16-23 | N/A |
| CASI score | | |
| Mean ±SD | 65.1 ± 10.3 | N/A |
| Range | 49-79 | N/A |

*AD, Alzheimer diseases; MMSE, mini-mental status examination; CASI, cognitive abilities screening instrument N/A, not available; Values shown are means ± SD.

COMPOSITION AND METHOD OF USING MIR-302 PRECURSORS AS DRUGS FOR TREATING ALZHEIMER'S DISEASES

PRIORITY

The present invention claims priority to the U.S. Provisional Application Ser. No. 62/262,280 filed on Dec. 2, 2015, which was entitled "miR-302 Attenuates Aβ-induced Neurotoxicity through Activation of Akt Signaling". The present application also claims priority to the U.S. patent application Ser. No. 13/572,263 filed on Aug. 10, 2012, Ser. No. 14/502,608 filed on Sep. 30, 2014, and Ser. No. 14/527,439 filed on Oct. 29, 2014, all of which are entitled "An Inducible Gene Expression Composition for Using Eukaryotic Pol-2 Promoter-Driven Transcription in Prokaryotes and The Applications Thereof". The present application is a continuation-in-part (CIP) application of the U.S. patent application Ser. No. 13/572,263 filed on Aug. 10, 2012, Ser. No. 14/502,608 filed on Sep. 30, 2014, and Ser. No. 14/527,439 filed on Oct. 29, 2014, all entitled "An Inducible Gene Expression Composition for Using Eukaryotic Pol-2 Promoter-Driven Transcription in Prokaryotes and The Applications Thereof", which are hereby incorporated by reference as if fully set forth herein.

FIELD OF INVENTION

This invention generally relates to a composition and method of using recombinant microRNAs (miRNA) and their hairpin-like precursors (pre-miRNA) as therapeutic drugs for treating Alzheimer's diseases (AD). More specifically, the present invention relates to the use of man-made miRNA miR-302 precursors (pre-miR-302) for AD therapy in humans. These pre-miR-302 drugs can be produced in prokaryotes as a form of expression-competent DNA vectors and/or hairpin-like structured RNAs. As prokaryotic cells do not transcribe or process hairpin-like RNAs, which resemble a transcriptional termination code in prokaryotes, and further in view of the lack of several essential eukaryotic enzymes such as type-II RNA polymerases (Pol-2) and RNaseIII Dicers in prokaryotes, the present invention herein further teaches a method for expressing pre-miRNAs in prokaryotes, or called pro-miRNA, using a novel hairpin-like RNA transcription mechanism newly found in prokaryotes (as disclosed in our priority U.S. patent application Ser. No. 13/572,263). In addition, since miR-302 is a well-known embryonic stem cell (ESC)-specific factor in humans, our findings of this invention can be further used to advance the designs and development of novel regenerative medicine for treating many other ageing-related degenerative diseases, such as Parkinson's diseases, diabetes, osteoporosis, and cancers.

BACKGROUND

Insulin resistance represents a loss or reduction in its normal functionality on target tissues and hence affects our cognitive and memory functions, ultimately leading to the onset of Alzheimer disease (AD) (Cholerton et al, 2011). Insulin resistance has been linked to several previously identified risk factors that accelerate the cognitive dysfunction and ageing process, including diabetes, obesity, hypertension, hyperlipidemia, and metabolic syndrome (Spielman et al, 2014). Particularly, brains exhibit defective insulin receptor (IR) and insulin receptor substrate-1 (IRS-1) show alteration or aberrant activation of insulin signaling in progression of AD, the most common cause of dementia (Williamson et al, 2012). These findings suggest that neuronal insulin signaling becomes dysfunction in the AD brains similar to the dementia symptoms of Type 2 diabetes. The pathogenesis of AD is initially triggered by the presence of extracellular amyloid-β (Aβ) peptides, which impair mitochondrial membrane potential (MMP) and contribute to an increase in the accumulation of intracellular reactive oxygen species (ROS), ultimately leading to neuronal cell death (Butterfield D A, 2002; Li et al, 2015). It has been well established that Aβ deposition may play a pathogenic role in age-associated AD pathogenesis (Lesne et al, 2013). In addition, our previous studies have indicated that Aβ induces p-Ser307 IRS-1 expression and inhibits IRS-1 tyrosine phosphorylation and its downstream target protein kinase B (PKB, also called Akt) (Kornelius et al, 2015). Subsequently, Aβ further suppresses Ser9 phosphorylation of glycogen synthase kinase 3β (GSK3β), which is one of the enzymes responsible for causing tau hyperphosphorylation and neurotoxicity (Hernandez et al, 2013). These findings all indicate that insulin signaling plays a key regulatory role in Aβ-induced neurotoxicity and neuronal cell death in AD patients.

Cell survival is maintained by external factors such as growth factors, the lack of which often causes apoptosis. The Akt signaling pathway has been reported as a major downstream effector of growth factor-mediated cell survival mechanisms that inhibit apoptosis (Bhat and Thirumangalakudi, 2013). To this, Akt functions to promote cell survival by inactivating certain pro-apoptotic mediators such as Bid, a pro-apoptotic member of the Bcl-2 family involved in the induction of death receptor-mediated apoptosis (Majewski et al, 2004). Also, Akt signaling can reduce oxidative stress via activating the nuclear factor erythroid 2-related factor 2 (Nrf2)/heme oxygenase-1 (HO-1) antioxidant pathway (Surh et al, 2008), subsequently leading to prevention of Aβ-induced neurotoxicity (Kwon et al, 2015). As a result, both of these reported Akt-mediated protective mechanisms against cell apoptosis and oxidative stress may be useful for preventing neurodegeneration and mitochondrial dysfunction in human brains. Interestingly, in human embryonic stem cells (hESC), microRNA miR-302 has been found to mediate Akt activation through downregulating phosphatase and tensin homolog (PTEN) in order to maintain the pluripotency of hESCs (Alva et al, 2011). Moreover, Akt signaling also regulates the pluripotency-associated gene Nanog to maintain stem cell self-renewal and anti-ageing (Kuijk, 2010; Han et al, 2012). Taken together, based on all the above findings, we have proposed that miR-302 may be able to stimulate the activation of the Akt signaling pathway in neurons, so as to prevent Aβ-induced neurotoxicity in AD patients. Yet, neurons as one type of somatic cells normally do not express miR-302.

MicroRNA (miRNA) miR-302 is the most abundant non-coding RNA species specifically found in human embryonic stem cells (hESCs) and induced pluripotent stem cells (iPSCs). Our previous studies have shown that ectopic expression of miR-302 in mammalian somatic cells is able to reprogram the somatic cells to hESC-like iPSCs (as demonstrated in Lin et al., 2008, 2010 and 2011; EP 2198025; U.S. Ser. No. 12/149,725; U.S. Ser. No. 12/318,806; U.S. Ser. No. 12/792,413). Moreover, we have also observed that introduction of miR-302 into mammalian cells can further stimulate the expression of many other miRNA species, such as miR-92, miR-93, miR-367, miR-369, miR-371373, miR-374, miR-517, and the whole miR-520 familial members (Lin et al., 2008, 2010 and 2011; EP 2198025;

U.S. Ser. No. 12/149,725; U.S. Ser. No. 12/318,806; U.S. Ser. No. 12/792,413). Further analyses using the online "TARGETSCAN" and "PICTAR-VERT" programs, published in the Sanger Institute miRBase website (http://www.mirbase.org/), revealed that miR-302 shares over 400 target genes with these stimulated miRNAs, suggesting that they may play a similar or partially functional role like miR-302. Based on ours and many other previous reports, these shared target genes include, but not limited, members of RAB/RAS-related oncogenes, ECT-related oncogenes, pleiomorphic adenoma genes, E2F transcription factors, cyclin D binding Myb-like transcription factors, HMG-box transcription factors, Sp3 transcription factors, transcription factor CP2-like proteins, NFkB activating protein genes, cyclin-dependent kinases (CDKs), MAPK/JNK-related kinases, SNF-related kinases, myosin light chain kinases, TNF-alpha-induce protein genes, DAZ-associated protein genes, LIM-associated homeobox genes, DEAD/H box protein genes, forkhead box protein genes, BMP regulators, Rho/Rac guanine nucleotide exchange factors, IGF receptors (IGFR), endothelin receptors, left-right determination factors (Lefty), cyclins, p53 inducible nuclear protein genes, RB-like 1, RB binding protein genes, Max-binding protein genes, c-MIR cellular modulator of immune recognition, Bcl2-like apoptosis facilitator, protocadherins, TGFβ receptors, integrin β4/β8, inhibin, ankyrins, SENP1, NUFIP2, FGF9/19, SMAD2, CXCR4, EIF2C, PCAF, MECP2, histone acetyltransferase MYST3, nuclear RNP H3, and many nuclear receptors and factors. Notably, the majority of these target genes are highly involved in embryonic development and cancer tumorigenecity. Hence, it is conceivable that miR-302 can stimulate these downstream homologous miRNAs, such as miR-92, miR-93, miR-367, miR-371373, miR-374, and miR-520s, to enhance and/or maintain its functionality.

Particularly, we noted that miR-302, miR-9293, miR-367, miR-371374, and miR-520s are all hESC-specific miRNAs that are abundantly expressed in hESCs and iPSCs (Lin et al, 2008; EP 2198025; U.S. Ser. No. 12/149,725), all of which are also useful for designing and developing novel regenerative medicine. To achieve this goal, stem cells such as hESCs and iPSCs can be used as a treasure box as well as a tool for us to screen, search, extract, and produce novel effective drug-like ingredients that are useful for designing and developing many pharmaceutical and therapeutic applications, including but not limited, for stimulating tissue/organ regeneration, for repairing and/or rejuvenating damaged/aged cells/tissues, for treating ageing-associated degenerative diseases (i.e. Alzheimer's diseases, Parkinson's diseases, osteoporosis, diabetes and cancers), and for preventing tumor and/or cancer formation/progression/metastasis. As a result, it is conceivable that we can use these hESC-specific miRNAs as candidate drugs for developing novel therapies and treating human diseases in vivo. To fulfill this goal, we need a method for producing a significantly large amount of hairpin-like miRNAs and their precursors (pre-miRNAs) using modern DNA recombination and amplification technologies with bacterial cells; yet, it has been widely known that hairpin-like DNA/RNA structures resemble signals of intrinsic transcription termination mechanisms in prokaryotes (McDowell et al., *Science* 1994) and hence make it impossible for prokaryotic cells to transcribe hairpin-like RNAs, such as small hairpin RNAs (shRNA), microRNAs (miRNA) and the related precursors (i.e. pre-miRNA). To this problem, neither the first finder of miR-302—Houbaviy et al. (*Developmental Cell* (2003) 5, 351-358) nor the next follower Kim et al. (WO 2005/056797) could provide any solution for it.

Furthermore, as learning from current textbooks, a person of ordinary skill in the art must know that prokaryotic and eukaryotic transcription machineries are different and thus are not compatible to each other in many aspects. For example, based on most current understandings, eukaryotic RNA polymerases do not directly bind to gene promoter sequences and hence require additional accessory proteins to help it to initiate RNA transcription, whereas prokaryotic RNA polymerases can form a holoenzyme that binds directly to gene promoters, so as to initiate RNA transcription. However, because the holoenzyme can not process through a DNA sequence with a high degree of secondary structures, such as a hairpin DNA, the prokaryotic promoters naturally do not contain any hairpin-like structure, which otherwise resembles a transcription termination code in prokaryotes (McDowell et al, 1994). In addition, it is a common sense for a person of ordinary skill in the art to understand that eukaryotic messenger RNA (mRNA) is transcribed in the nucleus by type II RNA polymerases (pol-2) and then processed and exported to the cytoplasm for protein synthesis, whereas prokaryotic RNA transcription and protein translation take place simultaneously off the same piece of DNA in the same place (cytoplasm) because prokaryotic cells such as bacteria and archaea do not possess any nucleus-like structure. Due to these differences, it makes prokaryotes difficult or even impossible to produce eukaryotic RNAs and the related peptides/proteins using eukaryotic RNA promoters, which tend to contain DNA motifs with specific secondary structures in the 5'-untranslational regions (5'-UTR).

Prior arts attempt at producing mammalian gene products in bacterial cells, such as U.S. Pat. No. 7,959,926 to Buechler and U.S. Pat. No. 7,968,311 to Mehta, used bacterial or bacteriophage promoters. Since prokaryotes do not contain any splicing machinery such as spliceosome to process introns, the intron-less complementary DNA (cDNA) of a desired gene was made and cloned into a plasmid vector driven by a bacterial or bacteriophage promoter. Then, the vector so obtained was introduced into a competent strain of bacterial cells, such as *Escherichia coli* (*E. coli*), for expressing the gene transcripts (i.e. mRNAs) and subsequently translating the mRNAs into proteins. Nevertheless, the bacterial and bacteriophage promoters, such as Tac, Lac, Tc, T1, T3, T7, and SP6 RNA promoters, are not pol-2 promoters and their transcription activities tend to be an error-prone process, which causes mutations and can not express hairpin-like miRNAs or shRNAs as reported by McDowell et al (*Science* 1994). In addition, Mehta further taught that glycerol/glycerin might be used to increase the efficiency of bacterial transformation; yet, no teaching was related to enhancement of RNA transcription, in particular pol-2 promoter-driven hairpin-like RNA transcription. Due to lack of compatibility between eukaryotic and prokaryotic transcription systems, these prior arts were still limited by the use of prokaryotic RNA promoters for expressing gene cDNA in prokaryotes and none of them were useful for expressing hairpin-like RNAs, such as miRNAs and shRNAs.

Using a novel hairpin-RNA transcription mechanism newly found in prokaryotes (Lin et al, U.S. patent application Ser. No. 13/572,263, Ser. No. 14/502,608, and Ser. No. 14/527,439), we now can overcome the prokaryotic transcription termination mechanisms and thus induce overexpression of hairpin-like microRNA precursors (pre-miRNA) and shRNAs in prokaryotic cells, particularly useful for expressing human miR-302 familial microRNAs (miR-302a, b, c, d, e, and f) and their precursors (pre-miR-302). By adding certain transcriptional inducer chemicals into bacterial culture medium, we are able to transform prokaryotes to adopt eukaryotic pol-2 and/or viral pol-2-like promoters for transcribing our desired hairpin RNAs and the related miRNAs/shRNAs thereof. The advantages of this production method are: first, cost-effective production due to the fast and cheap growth of single-cell prokaryotes such as bacterial cells; second, easy handling because of no need for culturing dedicate hybridomas or mammalian cells; third, high product quality in view of the improved reading fidelity of pol-2 promoter-driven transcription; fourth, industrial level bulk production for desired hairpin RNAs and their related miRNAs/shRNAs as well as the introduced vectors all at once in prokaryotes; and last, multiple task capacity in that the desired RNAs and other desired peptides/proteins can be produced together but separately isolated and purified from the resulting bacterial extracts and/or lysates for further applications. Therefore, taken together, a composition and method for producing hairpin RNAs and/or their related miRNAs/shRNAs using eukaryotic RNA promoter-driven transcription in prokaryotes is highly desirable for the need of mass production of hairpin-like RNA drugs.

SUMMARY OF THE INVENTION

Our previous invention European patent No 2198025 has demonstrated the use of miR-302-like small hairpin RNAs (shRNAs) and/or short interfering RNAs (siRNAs) to reprogram mammalian somatic cells to hESC-like induced pluripotent stem cells (iPSCs). These miR-302-like shRNAs/siRNAs possess the same functional structures as native miR-302 molecules and are all share the same 17-nucleotide seed sequence of 5'-UAAGUGCUUC CAUGUUU-3' (SEQ.ID.NO.1) in order to specifically and concurrently target over 400 genes in humans. In our special designs and methods, these miR-302-like shRNAs/siRNAs are transcribed from a recombinant miR-302 familial gene (SEQ.ID.NO.2, as shown in FIG. 13A), of which the transcripts can be further processed into precursors (i.e. pre-miRNAs) of miR-302a (pro-miR-302a, SEQ.ID.NO.3), miR-302b (pro-miR-302b, SEQ.ID.NO.4), miR-302c (pro-miR-302c, SEQ.ID.NO.5), and (pro-miR-302d, SEQ.ID.NO.6), as shown in FIG. 13B. As a result, the present invention further discloses a novel composition and method of using these miR-302-like shRNAs/siRNAs for treating diabetes-associated Alzheimer's diseases (AD) in humans.

In one preferred embodiment, the desired miR-302-like shRNA/siRNA molecules of the present invention are derived from a vector-based expression composition, such as plasmid and/or viral vector, which can be delivered into at least a targeted cell type, tissue and/or organ, in particular brain and/or pancreas, for releasing the desired miR-302-like shRNAs/siRNAs for AD therapy. In another preferred embodiment, the desired miR-302-like shRNAs/siRNAs can be produced in a mass amount in vitro and then further purified and used for in vivo delivery into at least a targeted cell type, tissue and/or organ, in particular brain and/or pancreas, for AD therapy. For in vivo treatments, the delivery/transfection method includes, but not limited, all kinds of injection, lipid-/glycerin-/chemical-mediated infusion/perfusion, peptide-/sugar-/liposome-/chemical-mediated transfection, antigen-/antibody-/receptor-mediated endocytosis, transposon-/retrotransposon-mediated cell penetration, adenoviral/retroviral/lentiviral infection, and a combination thereof. For facilitating in-vivo delivery efficiency, the desired miR-302-like shRNAs/siRNAs can be further formulated with at least a kind of lipid-/liposome-, peptide-/protein-, sugar-, and/or glycylglycerin-based molecules, and/or the combination thereof, which are able to stabilize the structural integrity of shRNAs/siRNAs as well as to enhance drug penetration rates in vivo.

In our experimental design, which is provided here as an example of practical evidence, FIGS. 1A and 1B show the basic construct of a miR-302-expressing lentiviral plasmid vector (called pLenti-EF1alpha-RGFP-miR302 or pLVX-GFP-miR302) that has been tested for treating ageing-related diseases (i.e. cancers, diabetes and AD) in animal models in vivo as well as been used for performing mass production of miR-302-like microRNAs/shRNAs/siRNAs in prokaryotes (such as E. coli and Lactobacillus spp bacterial cells). As demonstrated in FIG. 1A, components of the miR-302-expressing plasmid vector can be re-arranged to be located in different regions of the vector or even deleted for providing more compact and effective delivery into targeted cells. In view of this example, a person of ordinary skill in the art would understand that any vector with similar structural features can be used for achieving the same functional purpose as the present invention. Additionally, after vector delivery into the targeted cells, the natural processes of miR-302 generation from a miR-302-expressing plasmid/vector are further demonstrated in FIG. 1B.

For using prokaryotes to produce hairpin-like microRNAs/shRNAs, the recombinant miR-302 familial gene (SEQ.ID.NO.2; FIG. 13A) must be placed in the 5'-UTR of its encoding gene (i.e. RGFP), as shown in FIGS. 1A and 1B. Because prokaryotic cells do not contain any splicing machinery such as spliceosomes to process in-frame introns, the original vectors used in our prior inventions, such as EP 2198025; U.S. Ser. No. 12/149,725; U.S. Ser. No. 12/318,806; U.S. Ser. No. 12/792,413 to Lin, can not be used for produce hairpin-like microRNAs/shRNAs in prokaryotes. Also, since a hairpin-like DNA/RNA structure resembles the stop signal of intrinsic transcription termination mechanisms in prokaryotes (McDowell et al., 1994), our design of the recombinant miR-302 familial gene located in the 5'-UTR of the RGFP gene can not be transcribed in prokaryotes without adding any chemical inducer like MOPS, glycerin, and/or ethanol (FIGS. 3, 4 and 5). To overcome this problem, our claimed priority invention, U.S. patent application Ser. No. 13/572,263, Ser. No. 14/502,608, and Ser. No. 14/527,439 to Lin, had found a novel hairpin-RNA transcription mechanism existing in prokaryotic cells. As shown in FIGS. 2, 3, 4, 5 and 6, by adding certain transcription inducers such as 3-morpholinopropane-1-sulfonic acid (MOPS), ethanol, and/or glycerin (or called glycerol) in bacterial culture, we can further transform the prokaryotes to adopt eukaryotic pol-2 and viral pol-2-like promoters for transcribing hairpin-like RNAs (i.e. the recombinant miR-302 familial gene, SEQ.ID.NO.2; FIG. 13A), so as to achieving mass production of the miR-302-like shRNA/siRNA molecules. These eukaryotic pol-2 and viral pol-2-like promoters include, but not limited, mammalian EF1alpha and/or cytomegalovirus (CMV) promoters, as shown in FIG. 1A.

In experiments, competent cells (i.e. E. coli) are transformed or transfected by a vector with a structural design similar to pLenti-EF1alpha-RGFP-miR302 and then cultivated in Luria-Bertani (LB)-based culture broth at about 37° C. with frequent agitation at about 150~300 rpm. After ≥8-hour incubation, the transformed cells grown in LB broth supplemented with about 0.05%~8% (v/v) MOPS and/or about 0.05%~4% (v/v) glycerin show abundant expression of red RGFP proteins that can stain the LB broth into red, whereas other blank controls without any inducer addition fail to produce any RGFP, as shown in FIG. 2 and Example 1. The presence of red fluorescent RGFP indicates that both its RNAs and proteins are successfully produced. To further confirm the specificity of RNA transcription induced by the chemical inducers, such as MOPS and/or glycerin, two strains of transformed competent cells are prepared as follows: one carries a pLVX-GFP-miR302+367 plasmid vector that has a modified CMV promoter-driven green fluorescent protein (AcGFP) gene encoding the whole miR-302~miR-367 cluster in its 5'-UTR and the other carries the aforementioned pLenti-EF1alpha-RGFP-miR302 vector (FIG. 1A). After ≥8-hr incubation in culture medium/broth supplemented with ≥0.1% (v/v) MOPS, the cells transformed with pLVX-GFP-miR302+367 produce green AcGFP only, while the other cells transformed with pLenti-EF1alpha-RGFP-miR302 show red RGFP (FIG. 3). This result clearly indicates that the chemicals like MOPS and glycerin can induce specific hairpin-like RNA expression through both eukaryotic pol-2 promoter-driven and pol-2-like viral promoter-driven transcription mechanisms. Based on our practical evidence shown in FIGS. 2, 3 and 4, these "transcription inducer" chemicals include, but not limited, ethanol, glycerin (glycerol), MOPS and their chemical isoforms as well as derivatives, such as 2-(N-morpholino) ethanesulfonic acid (YMS), and 4-(2-hydroxyethyl)-1-piperazineethanesulfonic acid (HEPES), mannitol, and/or a mixture thereof. The quantitative levels of the induced RGFP protein production can be measured by Western blot analysis, as shown in FIG. 5, in which Bacterial RuvB protein is served as a house-keeping standard to normalize the RGFP expression. In addition, the quantitative levels of the induced hairpin-like miR-302/pre-miR-302 expression can also be measured by Northern blot analysis, as shown in FIG. 6. Due to the structural similarity of all microRNAs (miRNAs) and shRNAs, it is obvious for a person of ordinary skill in the art to use the vector design of the present invention for producing other kinds of miRNAs, shRNAs and/or their precursors/homologs in prokaryotes.

Due to our discovery of the hairpin-RNA transcription mechanism in prokaryotic cells, the present invention is able to use either miRNA/shRNA-expressing viral vectors (i.e. pLenti-EF1alpha-RGFP-miR302; FIG. 1A) or hairpin-like shRNA/siRNA molecules (i.e. pro-miR-302a, b, c, and d; FIG. 13B) so obtained for disease therapy, in particular AD therapy as demonstrated in the present invention. In eukaryotic cells, these hairpin-like miRNAs/shRNAs can be further processed into mature microRNA molecules (i.e. miR-302a, b, c and d) for eliciting their functions. Alternatively, some non-coding RNAs (ncRNAs), such as short interfering RNAs (siRNAs) and small hairpin RNAs (shRNAs), can be designed to mimic native microRNAs. These ncRNAs preferably contain at least a sequence sharing 30% to 100% homology to a microRNA or a part of its precursor (pre-miRNA). Also, these shRNAs/siRNAs can be manually designed to contain perfectly matched hairpin-stem regions, while native microRNA precursors (pre-miRNAs or pri-miRNAs) often contain mismatched base pairs. Given that most of microRNAs function as specific gene silencers and may play a variety of distinctive roles in many physiological and pathological mechanisms, including but not limited to biological development, stem cell generation, nuclear reprogramming, cell differentiation, cell cycle regulation, tumor suppression, immunological defense, apoptosis, rejuvenation, wound healing, and many other more, the potential applications in theses pharmaceutical and therapeutical fields are therefore highly expected.

Induction of Eukaryotic Promoter-Driven miRNA/shRNA Expression in Prokaryotes.

As aforementioned, the lentiviral pLenti-EF1alpha-RGFP-miR302 plasmid vector contains a recombinant miR-302 familial cluster gene (SEQ.ID.NO.2; FIG. 13A) located in the 5'-UTR of its encoding RGFP gene (FIGS. 1A and 1B); as a result, the induced expression of the RGFP gene will also generate miR-302 molecules (miR-302a, b, c and d; SEQ.ID.NOs.3~6; FIG. 13B), as shown in the schematic mechanism of FIG. 1B. Due to lack of RNA splicing machinery (e.g. spliceosomes) in prokaryotic cells, the miR-302 molecules so obtained will remain as hairpin-like microRNA precursors (pre-miR-302s and pri-miR-302s), as shown in FIG. 6, which are useful for being isolated and delivered into eukaryotic cells for eliciting the desired function of miR-302. Using this production method, both of the vector and miR-302 molecules can be simultaneously amplified in the transformed prokaryotic cells, such as *E. coli*. The method for isolating the amplified pLenti-EF1alpha-RGFP-miR302 vector DNA and the transcribed miR-302 molecules are disclosed in Examples 5 and 6, respectively. The methods for delivering/transfecting miR-302, pre-miR-302 and/or its encoding expression vector (i.e. pLenti-EF1alpha/CMV-RGFP/GFP-miR302; FIG. 1A) into prokaryotic and/or eukaryotic cells can be selected from the group consisting of injection, microinjection, lipid-/glycerin-/chemical-mediated infusion/perfusion, peptide-/sugar-/liposome-/chemical-mediated transfection, antigen-/antibody-/receptor-mediated endocytosis, transposon-/retrotransposon-mediated cell penetration, viral infection, gene gun penetration, electroporation, and a combination thereof.

After vector delivery into cells (Example 1), we observed the induced expression of red RGFP and green GFP, respectively, in the transformed cells cultivated in LB broth supplemented with either MOPS or glycerin, or ethanol, or in combination, but not in LB broth without any inducer added (FIGS. 3, 4 and 5), indicating that this transcriptional induction effect is highly dependent on these chemical inducers and hence no transcriptional leakage can be found in blank negative controls. The expression of RGFP protein was confirmed by Western blot analysis, as shown in FIG. 5. After confirming the induced RGFP expression, we further measured the induced miR-302 expression levels in the pLenti-EF1alpha-RGFP-miR302-transformed cells with or without inducer addition. The result of induced hairpin-like miR-302/pre-miR-302 expression was confirmed by Northern blot analysis, as shown in FIG. 6. In agreement with the result of induced RGFP expression, the miR-302 expression was detected only in transformed cells treated with MOPS, glycerin and/or ethanol, but not in blank negative controls, indicating that in the absence of any chemical inducer no transcription activity can function through a gene promoter containing a hairpin-like structure in prokaryotic cells, as reported by McDowell et al (*Science* 1994). Hence, the hairpin-like miR-302 expression shown in FIG. 6 is a specific result induced by the added transcription inducers of the present invention, not a random transcription leakage event.

Functional Applications of the Present Invention in Neural Stem Cell Generation.

MicroRNA miR-302 has been found to reprogram mammalian somatic cells to embryonic stem cell (ESC)-like induced pluripotent stem cells (iPSC) (Lin, 2008, 2010, 2011; U.S. patent application Ser. Nos. 12/149,725 and 12/318,806 to Lin). Using these iPSCs, many stem cell-associated applications and therapies have been developed for advancing modern regenerative medicine. Yet, miR-302 is only abundantly found in human ESCs rather than differentiated tissue cells. Also, isolation of miR-302 from human ESCs is highly debatable, costly and tedious. To solve these problems, the present invention provides a simple, cheap, fast and inducible composition and method for mass production of hairpin-like miR-302 molecules and/or their precursors/homologs in prokaryotes. Moreover, the isolation of miR-302 and/or its precursors from prokaryotic cells is relatively easy and cost-effective, as shown in FIG. 6 and Example 6 of the present invention.

We have used the pLenti-EF1alpha-RGFP-miR302-transformed E. coli cells to produce and isolate high quantity and quality of the pLenti-EF1alpha-RGFP-miR302 vector and pre-miR-302s, as shown in Examples 5 and 6. The use of pLenti-EF1alpha-RGFP-miR302 had been shown to produce human ESC-like iPSCs in view of our previous U.S. patent application Ser. No. 12/149,725 and Ser. No. 12/318, 806. Also, the iPSCs so obtained can be further differentiated into neuron cells as demonstrated in our previous studies (Lin et al, 2008, 2010 and 2011). In FIG. 7 and Example 2 of the present invention, we further used a high concentration (≥600 µg/mL) of pre-miR-302s obtained by the method of the present invention to reprogram human keratinocytes to iPSCs, which then expressed strong ESC marker Oct4. Further analysis using bisulfate DNA sequencing assays showed that global DNA demethylation did occur in the nuclei of these iPSCs, particularly in the promoter regions of Oct4 and Sox2 genes, two of the most important reprogramming factors and markers in human ESCs and iPSCs (FIG. 8 and Example 8). As global DNA demethylation and Oct4 expression are widely known to be the first and most important sign of stem cell pluripotency (Simonsson and Gurdon, (2004) Nat Cell Biol. 6:984-990), the present invention may also provide a composition and method for inducing iPSC derivation using isolated miR-302 and/or pre-miR-302 molecules. To this application, the methods for delivering miR-302 and/or pre-miR-302 molecules into mammalian cells can be selected from the group of microinjection, lipid-/glycerin-/chemical-mediated infusion/perfusion, peptide-/sugar-/liposome-/chemical-mediated transfection, antigen-/antibody-/receptor-mediated endocytosis, transposon-/retrotransposon/caspase-mediated cell penetration, viral infection, gene gun penetration, electroporation, and a combination thereof.

The applications of isolated miR-302 and/or pre-miR-302 molecules may further include the induction and expansion of CD34-positive adult stem cells. As shown in FIGS. 9A and 9B, our recent studies in wound healing therapy using a novel miR-302-formulated drug revealed that treatments of relatively low concentrations (50~500 µg/mL) of the isolated miR-302/pre-miR-302 molecules not only greatly enhance scar-less wound healing but also induce CD34-positive adult stem cell expansion around the wounded area in pig skins in vivo. Based on the miR-302-treated (glycyl-glycerin-formulated miR-302s/pre-miR-302s+antibiotic ointment) result of FIG. 9B in comparison with that of control (only antibiotic ointment) result of FIG. 9A, it clearly showed a ≥40-fold increase of CD34-positive adult stem cell populations (labeled by green fluorescent antibodies) in vivo after miR-302 treatments. The currently known CD34-positive adult stem cell types include, but not limited, skin, hair, muscle, blood (hematopoietic), mesenchymal, and neural stem cells. As a result, since miR-302 can be used to induce CD34-positive adult stem cell expansion in vivo, this therapeutic effect may also help to re-grow and/or revive functional neurons for treating AD in patients.

MiR-302 Protects SK-N-MC Cells Against Aβ-Induced Apoptosis.

Recent studies have demonstrated the crucial functions of miR-302 in regulating oxidative stress-induced apoptosis. To address whether miR-302 exerts any protective effect on neuronal cells against Aβ-induced apoptosis, we transfected human neuronal SK-N-MC cells with a cytomegalovirus (CMV)-promoter-driven miR-302 expression lentivector as previously reported (Lin et al, 2008, 2010 and 2011), and then exposed to Aβ (2.5 µM) for 24 hours. After that, the miR-302-transfected cells were identified by the presence of a co-expressed AcGFP green fluorescent protein under an inverted fluorescent microscope (FIG. 14A) and the expression of miR-302 was further confirmed by RT-qPCR (n=3, p<0.01, FIG. 14B) and miRNA microarray analysis (FIG. 12), showing successful transcription of the whole miR-302 familial cluster (i.e. miR-302a, b, c, and d). Notably, FIG. 14C further demonstrated that Aβ treatment triggered massive cell death in control cell groups, whereas miR-302-transfected cells showed marked attenuation of such Aβ-induced cell death (n=3, p<0.01). To determine which kind of cell death induced by Aβ, we further examined the nuclei fragmentation by DAPI staining. As shown in FIGS. 14D and 14E, Aβ treatment disrupted nucleus margin and significantly increased the apoptotic cell population in the control groups compared to those of miR-302-transfected cells (n=3, p<0.01). In addition, FIG. 14F revealed that Aβ treatment markedly increased the cleavage formation of both caspase 3 and PARP in control cells but not in miR-302-transfected cells (n=3, p<0.01), further confirming this point. Taken together, our data strongly suggest that miR-302 plays a protective role in preventing Aβ-induced cell apoptosis.

Activation of Akt Signaling is Involved in miR-302-Mediated Neuroprotection.

We have previously reported that restoration of insulin sensitivity in neurons leads to Akt activation and so as to inhibit Aβ-induced apoptosis (Kornelius et al, 2015). To determine whether miR-302 expression can restore neuronal insulin sensitivity and prevent Aβ-induced neurotoxicity, we used western blot analyses to measure the expression levels of major insulin signaling-related proteins, such as pSer307-IRS-1, tyrosine phosphorylation of IRS-1, and their downstream target pSer473-Akt. As shown in FIG. 15A, Aβ treatment in control cells significantly increased p-307 IRS-1 serine phosphorylation (n=3, p<0.05) while decreasing IRS-1 tyrosine phosphorylation (n=3, p<0.01), both of which are considered as hallmarks of insulin resistance; yet, in miR-302-transfected cells this Aβ-induced insulin resistance was markedly attenuated (n=3, p<0.05). Moreover, Aβ treatment also led to a significant decrease of p-Ser 473-Akt in control groups but not in miR-302-transfected cells (n=3, p<0.01) (FIG. 15A). To further elucidate the protective role of PI3K/Akt signaling in miR-302-transfected cells, we applied a PI3K inhibitor LY294002. As a result, FIG. 15B revealed that co-treatment of Aβ (2.5 µM) and LY294002 (20 µM) could disrupt miR-302-mediated Akt signaling (n=3, p<0.01) and thus resulted in a marked reduction of the viable cell population, as determined by MTT assay (n=3, p<0.01, FIG. 15C). All these findings suggest that miR-302 prevents Aβ-induced neurotoxicity and neuronal death via activating PI3K/Akt signaling. Alternatively, Aβ-impaired insulin signaling may also lead to an increase of GSK3β activity as well as tau hyperphosphorylation, a relevant step in AD pathogenesis. To this, we found that miR-302 expression could stimulate Akt signaling to slightly increase p-Ser 9-GSK3β levels and hence may provide a mild inhibitory effect on tau hyperphosphorylation (n=3, p<0.05) (FIG. 15D). As a result, FIG. 15D also showed that co-treatment of Aβ and LY294002 totally abolished the inhibitory effect of miR-302 on p-Ser 9-GSK3β expression and tau phosphorylation in control cells compared to those of miR-302-transfected cells (n=3, p<0.05). Taken together, our data demonstrate that miR-302 may exert its protective effects mainly through activating and/or restoring the Akt/GSK3β signaling pathway.

MiR-302 Attenuates Aβ-Induced Oxidative Stress Through Akt-Upregulated Nrf2/HO-1

To determine whether miR-302-mediated Akt activation can prevent Aβ-induced intracellular ROS accumulation, we performed a fluorometric assay to measure the concentration of hydrogen peroxide accumulated in the cells. As shown in FIG. 16A, Aβ treatment stimulated a significant elevation of intracellular superoxide radical anions in control groups but not in miR-302-transfected cells (n=3, p<0.01). Co-treatment of Aβ (2.5 µM) and insulin (1 µM) could restore the normal levels of intracellular superoxide radical anions in control groups (p<0.05), indicating that miR-302-mediated Akt activation did inhibit Aβ-induced ROS. Furthermore, Nrf2, a redox-sensitive transcription factor, may also confer protection against ROS damage by upregulating antioxidant-response elements, such as HO-1. Since PI3K/Akt signaling has been reported to elevate HO-1 expression and Nrf2-dependent transcription (Kwon et al, 2015), we further elucidate this possible anti-oxidant effect of miR-302 by Western blot assays. As a result, FIG. 16B revealed that Aβ treatment reduced both Nrf2 and HO-1 expressions in control groups but not in miR-302-transfected cells (n=3, p<0.05). To further confirm the source of this effect, further treatment of LY294002 (20 µM) with Aβ (2.5 µM) also decreased Nrf2 expression in miR-302-transfected cells (n=3, p<0.05) (FIG. 16C), indicating that miR-302 regulates Nrf2 expression via the PI3K/Akt signaling pathway. Moreover, activation of Akt signaling significantly restored the Nrf2 expression after co-treatment of Aβ (2.5 µM) and insulin (1 µM) in control groups (n=3, p<0.05) (FIG. 16C), further suggesting that miR-302-mediated Akt activation can prevent Aβ-induced ROS accumulation through the upregulation of Nrf2 and HO-1.

To investigate the miR-302 effect on Aβ-mediated mitochondria dysfunction and apoptosis, we examined MMP with JC-1 staining assays and the expression of apoptotic-associated marker truncated Bid (tBid) and anti-apoptotic-associated marker Bcl-2 with western blotting assays. As shown in FIG. 16D, control cells displayed a significant deficiency of mitochondrial membrane depolarization in response to Aβ treatment (n=3, p<0.05), which was however not found in miR-302-transfected cells, as indicated by the concurrent loss of cytoplasmic red J-aggregate fluorescence and elevation of diffused green fluorescence. Yet, this miR-302-mediated protective effect on MMP integrity could be totally abolished by co-treatment of Aβ (2.5 µM) and LY294002 (20 µM) for 24 hours (n=3, p<0.05), indicating the involvement of Akt/PI3K signaling. In addition, Aβ treatment resulted in a marked increase of tBid expression (p<0.01) and decrease of Bcl-2 (p<0.05) in control groups, but not in miR-302-transfected cells (FIG. 16E). All these findings clearly suggest that miR-302-mediated Akt activation can inhibit Aβ-induced oxidative stress, mitochondria dysfunction and apoptosis via upregulating Nrf2 activities.

MiR-302 Regulates Akt Signaling by Targeting PTEN and Inducing Nanog Expression

After having determined the important role of miR-302 in activating Akt signaling to prevent Aβ-induced neurotoxicity, we further investigate the molecular mechanism underlying such miR-302-mediated Akt activation. Recent studies have indicated that miR-302 promotes pluripotency through Akt signaling by targeting PTEN (Alva et al, 2011). To search the miR-302 target site in PTEN, we performed screening analyses using a prediction program, TargetScan (http://www.targetscan.org/), and identified a specific miR-302 binding site located in the 3'UTR of human PTEN gene (FIG. 17A). As our western blotting data have shown a significantly decrease of PTEN expression in miR-302-transfected cells (n=3, p<0.05) (FIG. 17B), it suggests that miR-302 may target this 3'UTR binding site to suppress PTEN expression. Also, since knockdown of PTEN can increase the pluripotency-associated gene Nanog expression (Kuijk et al, 2010), which is further mediated by PI3K/Akt signaling in ESCs (Alva et al, 2011), we herein examined the miR-302 effects on PTEN, pSer473 Akt, and Nanog expressions with western blot assays. As a result, FIG. 17C showed a marked elevation of Nanog expression only detected in miR-302-transfected cells (n=3, p<0.05), while Aβ treatment (2.5 µM for 24 hours) stimulated a significant increase of PTEN as well as decreases of pSer473 Akt and Nanog expressions in control groups but not in miR-302-transfected cells (n=3, p<0.05) (FIG. 17D). Interestingly, further studies revealed that blocking Akt signaling with LY294002 (20 µM for 24 hours) could restore Aβ-mediated inhibitory effects on pSer473 Akt and Nanog expressions in miR-302-transfected cells (n=3, p<0.05) (FIG. 17E), demonstrating that miR-302 activates Akt signaling to induce Nanog expression.

To determine whether Nanog plays a protective role in Aβ treatment, we further performed shRNA-mediated knockdown of Nanog in miR-302-transfected cells. As shown in FIG. 17F, downregulation of Nanog resulted in an increase of p-Ser307 IRS-1 expression as well as a decrease of both tyrosine phosphorylation and p-Ser 473-Akt/p-Ser 9-GSK3β levels in miR-302-transfected cells after Aβ treatment. Taken together, our results strongly suggest that miR-302 may confer protection against Aβ-induced neurotoxicity by downregulating PTEN to activate Akt and the downstream Nanog signaling.

In Vitro and in Vivo Expression Patterns of Naong and miR-302 (from LARP7 Gene).

We observed that impaired Nanog expression is associated with Aβ-disrupted insulin sensitivity. To investigate this point, we first performed RT-qPCR to show that Aβ treatment significantly decreased Nanog mRNA expression in control neurons in vitro (n=3, p<0.05, FIG. 18A). Then, we further addressed the relevance of this finding to human AD patients in vivo by measuring the mRNA expression levels of Nanog in AD patients' PBMCs. A detailed overview of the testing subjects' characteristics is summarized in Table 1. A number of AD patients (n=7) had moderated dementia by MMSE and CASI measurement scales, which can differentiate between AD patients and age-matched healthy controls (n=6). As a result, both scales of MMSE and CASI were decreased in these AD patients (Table. 1). To this, FIG. 18B further showed that the level of Nanog mRNA was significantly decreased in AD patients compared to normal age-match controls (p<0.05). This observation confirmed our therapy goal of miR-302 treatment in that AD patients exhibit reduced Nanog expression, which contributes to the pathogenesis of AD-associated neurodegeneration and therefore can be a valid therapy target for the miR-302 treatments of the present invention in AD patients.

In addition, the miR-302 familial gene is known to be encoded in the human LARP7 gene on the chromosome 4 of human genome. To determine whether the endogenous level of miR-302 was affected by Aβ-induced neurotoxicity during the progression of AD, we examined the expression of miR-302-encoding LARP7 gene by RT-qPCR with a special primer directed against the joining region of exons 8 and 9. As a result, FIG. 18C showed that Aβ treatment markedly decreased LARP7 mRNA expression in control neurons in vitro (n=3, p<0.05). Further detection of LARP expression in AD patients' PBMCs also revealed that the expression of LARP7 mRNA was significantly reduced in AD patients compared to normal age-match controls (FIG. 18D, p<0.05). These results proved that endogenous LARP7/miR-302 expression likely plays an important role in preventing the progression of AD.

In conclusion, as summarized in FIG. 19, impairment of insulin signaling not only presents a serious threat to neuron survival but also plays a critical role in ageing-related diseases such as AD. Our present invention, for the first time, demonstrated that miR-302 can regulate cell survival and anti-ageing processes via activating the Akt signaling pathway, which confers protection against Aβ-induced neurotoxicity in human neuronal cells. We herein concluded that: (i) miR-302 silences PTEN to activate Akt signaling, which the stimulates Nrf2/HO-1 elevation and hence attenuates Aβ-induced apoptosis, and (ii) miR-302-mediated Akt activation also stimulates Nanog expression to suppress p-Ser307 IRS-1 expression and thus enhance IRS-1 tyrosine phosphorylation and p-Ser 473-Akt/p-Ser 9-GSK3β formation. Conceivably, both of these newly identified miR-302 effects are useful for developing AD-related therapies.

Although the invention has been described with references to all of the above examples, it will be understood that modifications and variations are encompassed within the spirit and scope of the invention.

A. Definitions

To facilitate understanding of the invention, a number of terms are defined below:

Nucleic Acid: a polymer of deoxyribonucleic acid (DNA) or ribonucleic acid (RNA), either single or double stranded.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Oligonucleotide: a molecule comprised of two or more monomeric units of DNA and/or RNA, preferably more than three, and usually more than ten. An oligonucleotide longer than 13 nucleotide monomers is also called polynucleotide. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Nucleic Acid Composition: a nucleic acid composition refers to an oligonucleotide or polynucleotide such as a DNA or RNA sequence, or a mixed DNA/RNA sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives. Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a gene without any RNA processing or modification.

Precursor messenger RNA (pre-mRNA): primary RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Intron: a part or parts of a gene transcript sequence encoding non-protein-reading frames, such as in-frame intron, 5'-UTR and 3'-UTR.

Exon: a part or parts of a gene transcript sequence encoding protein-reading frames (cDNA), such as cDNA for cellular genes, growth factors, insulin, antibodies and their analogs/homologs as well as derivatives.

Messenger RNA (mRNA): assembly of pre-mRNA exons, which is formed after intron removal by intracellular RNA splicing machineries (e.g. spliceosomes) and served as a protein-coding RNA for peptide/protein synthesis. The peptides/proteins encoded by mRNAs include, but not limited, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "−" symbol or with an "a" or "antisense" in front of the DNA or RNA, e.g., "aDNA" or "aRNA".

Base Pair (bp): a partnership of Watson-Crick base pairing between adenine (A) and thymine (T) or between cytosine (C) and guanine (G) in a double-stranded DNA molecule. In RNA, uracil (U) is substituted for thymine (T) and another partnership of non-Watson-Crick base pairing between guanine (G) and uracil (U) also occurs. Generally the partnership is achieved through hydrogen bonding. For example, a sense nucleotide sequence "5'-A-T-C-G-U-3'" can form complete base pairing with its antisense sequence "5'-A-C-G-A-T-3" or "5'-A-U-G-A-T".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroxyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides.

Complementary or Complementarity or Complementation: a term used in reference to matched base pairing between two polynucleotides (i.e. sequences of an mRNA and a cDNA) related by the aforementioned "base pair (bp)" rules. For example, the sequence "5'-A-G-T-3'" is complementary to the sequence "5'-A-C-T-3'", and also to "5'-A-C-U-3'". Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knockout or knockdown effect at the level of mRNA degradation or translational suppression, which is usually triggered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (shRNA) and small interfering RNA (siRNA). These small RNA molecules usually function as gene silencers, interfering with expression of intracellular genes containing either completely or partially complementarity to the small RNAs.

Gene Silencing Effect: a cell response after a gene function is suppressed, consisting but not limited of cell cycle attenuation, G0/G1-checkpoint arrest, tumor suppression, anti-tumorigenecity, cancer cell apoptosis, and a combination thereof.

Non-coding RNA: an RNA transcript that cannot be used to synthesize peptides or proteins through intracellular translation machineries. Non-coding RNA includes long and short regulatory RNA molecules such as microRNA (miRNA), small hairpin RNA (shRNA), small interfering RNA (siRNA) and double strand RNA (dsRNA). These regulatory RNA molecules usually function as gene silencers, interfering with expression of intracellular genes containing either completely or partially complementary to the non-coding RNAs.

MicroRNA (miRNA): single-stranded RNAs capable of binding to targeted gene transcripts that have partial complementarity to the miRNA. MiRNA is usually about 17-27 oligonucleotides in length and is able to either directly degrade its intracellular mRNA target(s) or suppress the protein translation of its targeted mRNA, depending on the complementarity between the miRNA and its target mRNA. Natural miRNAs are found in almost all eukaryotes, functioning as a defense against viral infections and allowing regulation of gene expression during development of plants and animals.

Precursor MicroRNA (Pre-miRNA): hairpin-like single-stranded RNAs containing stem-arm and stem-loop regions for interacting with intracellular RNaseIII endoribonucleases to produce one or multiple microRNAs (miRNAs) capable of silencing a targeted gene or genes complementary to the microRNA sequence(s). The stem-arm of a pre-miRNA can form either a perfectly (100%) or a partially (mis-matched) hybrid duplexes, while the stem-loop connects one end of the stem-arm duplex to form a circle or hairpin-loop conformation. In the present invention, however, precursor of microRNA may also includes pri-miRNA.

Small interfering RNA (siRNA): short double-stranded RNAs sized about 18-27 perfectly base-paired ribonucleotide duplexes and capable of degrading target gene transcripts with almost perfect complementarity.

Small or short hairpin RNA (shRNA): single-stranded RNAs that contain a pair of partially or completely matched stem-arm nucleotide sequences divided by an unmatched loop oligonucleotide to form a hairpin-like structure. Many natural miRNAs are derived from hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol-2) promoter, or both, a Kozak consensus translation initiation site, polyadenylation signals, a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, perhaps binds to, and initiates RNA transcription. For the purposes of the instant invention, a promoter can be a known polymerase binding site, an enhancer and the like, any sequence that can initiate synthesis of RNA transcripts by a desired polymerase.

Eukaryotic Promoter: a sequence of nucleic acid motifs which are required for RNA transcription and can be recognized by eukaryotic type II RNA polymerases (pol-2), pol-2 equivalent, and/or pol-2-like viral polymerases.

Type-II RNA Polymerase (Pol-II or pol-2) Equivalent: a eukaryotic transcription machinery selected from the group consisting of mammalian type-II RNA polymerases (Pol-II or pol-2) and Pol-II-like viral RNA polymerases.

Type-II RNA Polymerase (Pol-II or pol-2) Promoter: a RNA promoter that is recognized and used by eukaryotic type-II RNA polymerases (Pol-II or pol-2) which transcribe eukaryotic messenger RNAs (mRNAs) and/or microRNAs (miRNAs). For example, but not limited, mammalian EF1alpha promoter is a pol-2 promoter.

Pol-II-like Viral Promoter: a viral RNA promoter capable of using the eukaryotic pol-2 or equivalent transcription machinery for its gene expression. For example, but not limited, cytomegaloviral (CMV) promoter and retroviral long terminal repeat (LTR) promoter are pol-2-like viral promoters.

Cistron: a sequence of nucleotides in a DNA molecule coding for an amino acid residue sequence and including upstream and downstream DNA expression control elements.

RNA Processing: a cellular mechanism responsible for RNA maturation, modification and degradation, including RNA splicing, intron excision, exosome digestion, nonsense-mediated decay (NMD), RNA editing, RNA processing, and a combination thereof.

Antibiotic Resistance Gene: a gene capable of degrading antibiotics selected from the group consisted of penicillin G, streptomycin, ampicillin (Amp), neomycin, G418, kanamycin, erythromycin, paromycin, phophomycin, spectromycin, tetracycline (Tet), doxycycline (Dox), rifapicin, amphotericin B, gentamycin, chloramphenicol, cephalothin, tylosin, and a combination thereof.

Restriction/Cloning Site: a DNA motif for restriction enzyme cleavage including but not limited to AatII, AccI, AflII/III, AgeI, ApaI/LI, AseI, Asp718I, BamHI, BbeI, BclI/II, BglII, BsmI, Bsp120I, BspHI/LU11I/120I, BsrI/BI/GI, BssHII/SI, BstBI/U1/XI, ClaI, Csp6I, DpnI, DraI/II, EagI, Ecl136II, EcoRI/RII/47III/RV, EheI, FspI, HaeIII, HhaI, HinPI, HindIII, HinfI, HpaI/II, KasI, KpnI, MaeII/III, MfeI, MluI, MscI, MseI, NaeI, NarI, NcoI, NdeI, NgoMI, NotI, NruI, NsiI, PmlI, Ppu10I, PstI, PvuI/II, RsaI, SacI/II, SalI, Sau3AI, SmaI, SnaBI, SphI, SspI, StuI, TaiI, TaqI, XbaI, XhoI, XmaI cleavage site.

Gene Delivery: a genetic engineering method selected from the group consisting of polysomal transfection, liposomal transfection, chemical transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Cell Cycle Regulator: a cellular gene involved in controlling cell division and proliferation rates, consisting but not limited of CDK2, CDK4, CDK6, cyclins, BMI-1, p14/p19Arf, p15Ink4b, p16Ink4a, p18Ink4c, p21Cip1/Waf1, and p27Kip1, and a combination thereof.

Tumor Suppression: a cellular anti-tumor and anti-cancer mechanism consisting but not limited of cell cycle attenuation, G0/G1-checkpoint arrest, tumor suppression, anti-tumorigenecity, cancer cell apoptosis, and a combination thereof.

Targeted Cell: a single or a plurality of human cells selected from the group consisting of a somatic cell, a tissue, a stem cell, a germ-line cell, a teratoma cell, a tumor cell, a cancer cell, and a combination thereof.

Cancerous Tissue: a neoplastic tissue derived from the group consisting of skin cancer, prostate cancer, breast cancer, liver cancer, lung cancer, brain tumor/cancer, lymphoma, leukemia and a combination thereof.

Antibody: a peptide or protein molecule having a preselected conserved domain structure coding for a receptor capable of binding a pre-selected ligand.

Pharmaceutical or therapeutic Application: a biomedical utilization and/or apparatus useful for stem cell generation, stem cell research and/or therapy development, cancer therapy, disease treatment, wound healing and tissue regeneration treatment, high-yield production of drug and/or food supplies, and a combination thereof.

Prokaryote or Prokaryotic Cell: an one-cell organism that lacks a distinct membrane-bound nucleus and has its genetic materials in the form of a continuous strand of DNA, such as bacteria.

Eukaryote or Eukaryotic Cell: an one-cell or multiple-cell organism whose cells contain a nucleus and other structures (organelles) enclosed within membranes, such as yeast, plant and animal cells.

Transcription Inducer: a chemical agent that can induce and/or enhance hairpin-like RNA transcription from a eukaryotic pol-2 or pol-2-like viral promoter in prokaryotic cells. For example, a transcription inducer contains, but not limited, a chemical structure similar to 3-morpholinopropane-1-sulfonic acid (MOPS), ethanol and/or glycerin, as well as their functional analogs, such as mannitol, 2-(N-morpholino)ethanesulfonic acid (MES) and 4-(2-hydroxyethyl)-1-piperazineethanesulfonic acid (HEPES), or a mixture thereof.

B. Compositions and Applications

A composition for using hairpin-like RNA mimics of microRNA precursors (pre-miRNA) capable of protecting human brain neurons from Aβ-induced neurotoxicity in Alzheimer's diseases, comprising: (a) at least a vector capable of expressing said hairpin-like pre-miRNA mimics through a eukaryotic promoter, wherein said vector is pLenti-EF1alpha/CMV-RGFP/GFP-miR302; and (b) at least a transcription inducer capable of delivering and inducing the expression of said hairpin-like pre-miRNA mimics in treated neurons, wherein the expression of said hairpin-like pre-miRNA mimics is induced by mixing (a) and (b) in a cell substrate containing the treated neurons.

Alternatively, the present invention is a method of protecting human brain neurons from Aβ-induced neurotoxicity in Alzheimer's diseases with hairpin-like RNA mimics of microRNA precursors (hairpin-like pre-miRNA mimics), comprising: (a) treating at least one neuron with a vector, wherein the vector contains SEQ.ID.NO.2 and is capable of expressing at least one hairpin-like pre-miRNA mimic through a eukaryotic promoter; and (b) inducing an expression of said at least one hairpin-like pre-miRNA mimic in the treated neurons with an administration of at least one transcription inducer.

In principle, the present invention provides a novel composition design and its applicable strategy for inducing adaptation of prokaryotes to use eukaryotic promoters for producing a large amount of hairpin-like RNAs as drugs for treating Alzheimer's diseases in human brain neurons. Preferably, said hairpin-like pre-miRNA mimics are miR-302 precursors (pre-miR-302) in a structural conformation selected from the group consisting of microRNA (miRNA), small hairpin RNA (shRNA), small interfering RNA (siRNA), their precursors and homologs, and a combination thereof.

Preferably, said prokaryote is a bacterial cells in particular, *Escherichia coli* (*E. coli*), and said transcription inducer is 3-morpholinopropane-1-sulfonic acid (MOPS), ethanol or glycerin, or a combination thereof. Also preferably, said eukaryotic RNA promoter is either a eukaryotic pol-2 promoter, such as EF1alpha, or a pol-2 compatible viral promoter, such as cytomegaloviral (CMV) promoter or retroviral long terminal repeat (LTR) promoter. The gene mediated by said eukaryotic RNA promoter is coded for either a non-coding or a protein-coding RNA transcript, or both, selected from the group consisted of microRNA (miRNA), small hairpin RNA (shRNA), small interfering RNA (siRNA), messenger RNA (mRNA), their precursors and homologs, and a combination thereof.

DESCRIPTION OF THE DRAWINGS AND TABLES

The patent or application file contains at least one drawing executed in color. Copies of this patent or patent application publication with color drawings will be provided by the Office upon request and payment of the necessary fee.

Referring particularly to the drawings for the purpose of illustration only and not limitation, there is illustrated:

FIGS. 1A and 1B show the basic design of a eukaryotic promoter-driven hairpin RNA expression composition (A) and its related RNA processing and translation mechanisms (B). Individual components of the eukaryotic promoter-driven hairpin RNA expression composition (i.e. the pLenti-EF1alpha-RGFP-miR302 plasmid vector which may carry both EF1alpha and CMV promoters) can be re-located in different places of the vector or even deleted for providing more compact and effective delivery into targeted cells. According to the disclosed mechanisms in (B), it is possible for an ordinary skill in the art to use any microRNA/shRNA in place miR-302 or any mRNA/protein in place of RGFP as taught in the present invention. Black arrows indicate the pathways for protein/peptide production, while white arrows indicate the steps for hairpin RNA generation.

Figure 1A:
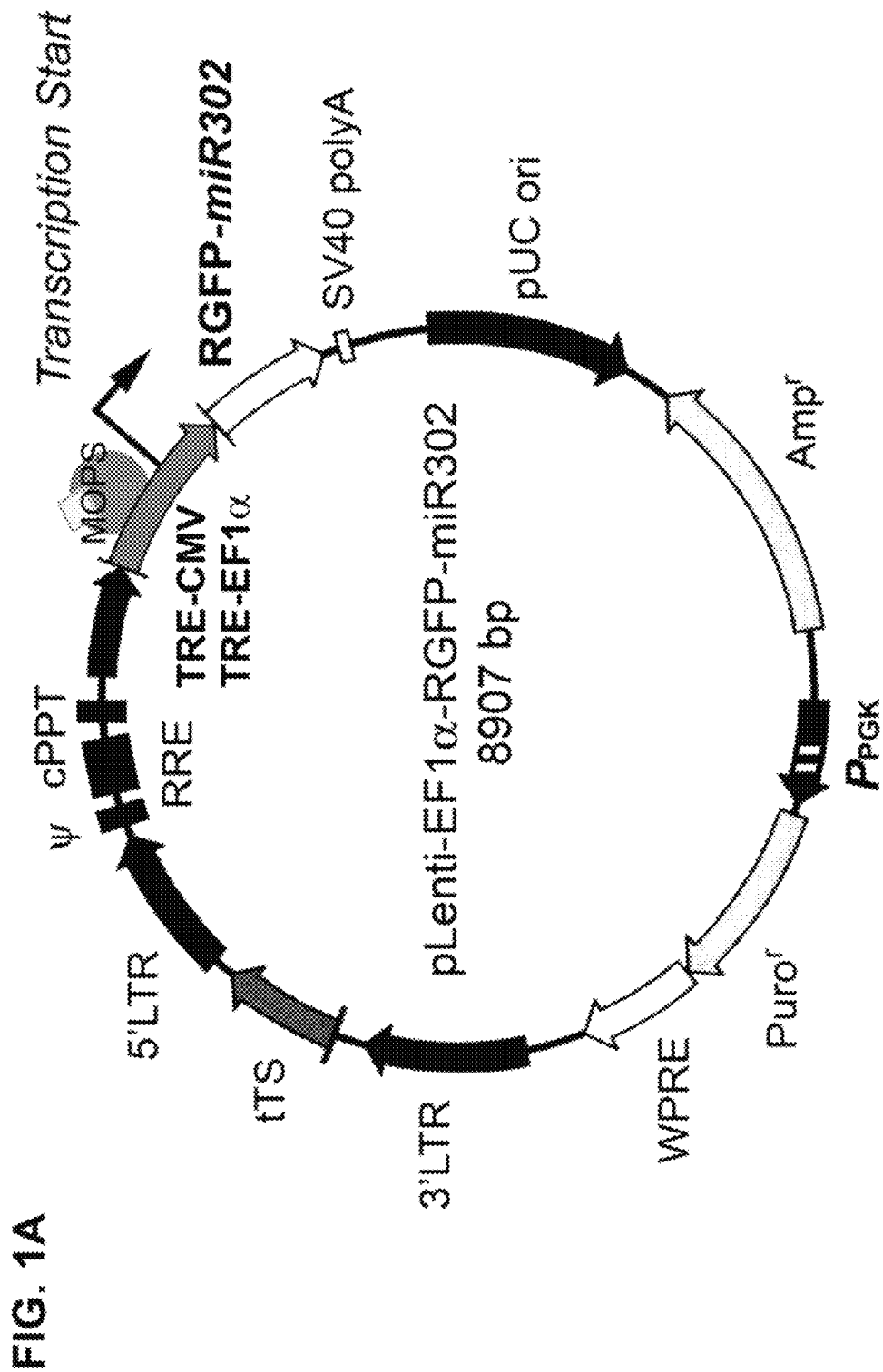
Figure 1B:
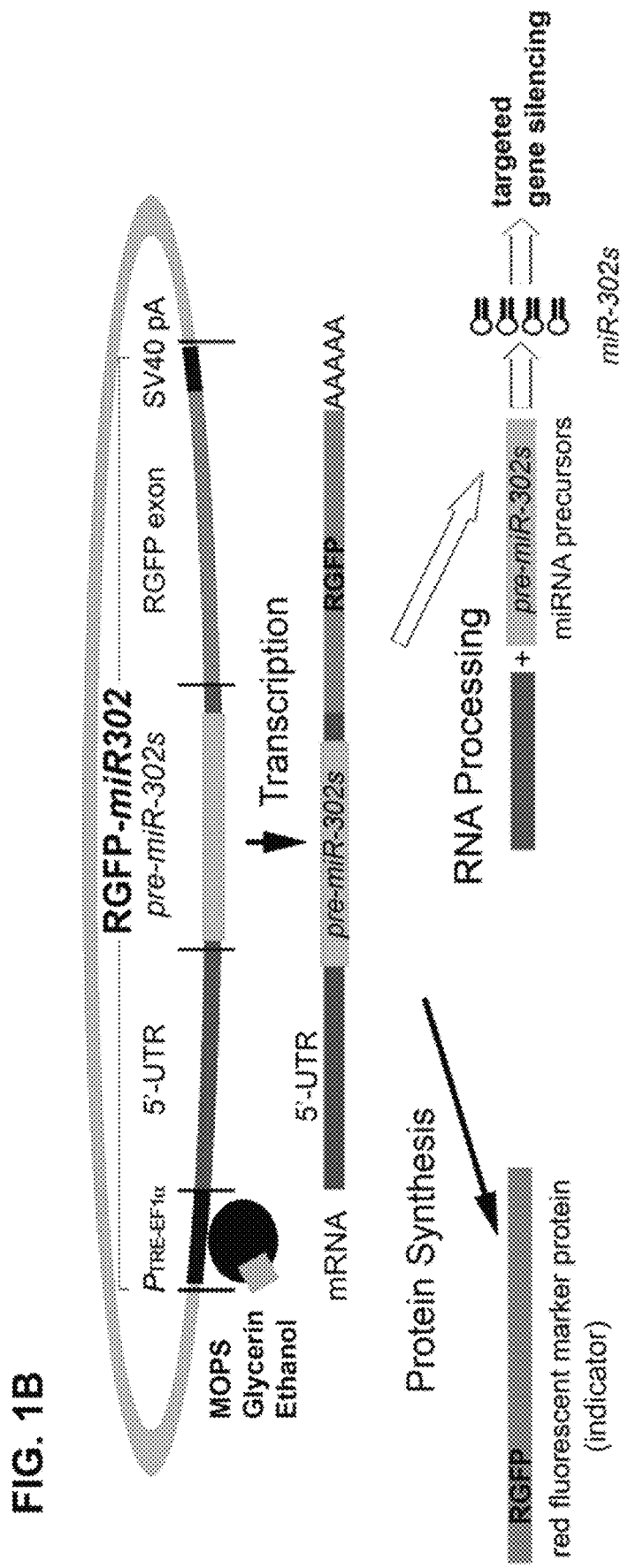
Figure 2:
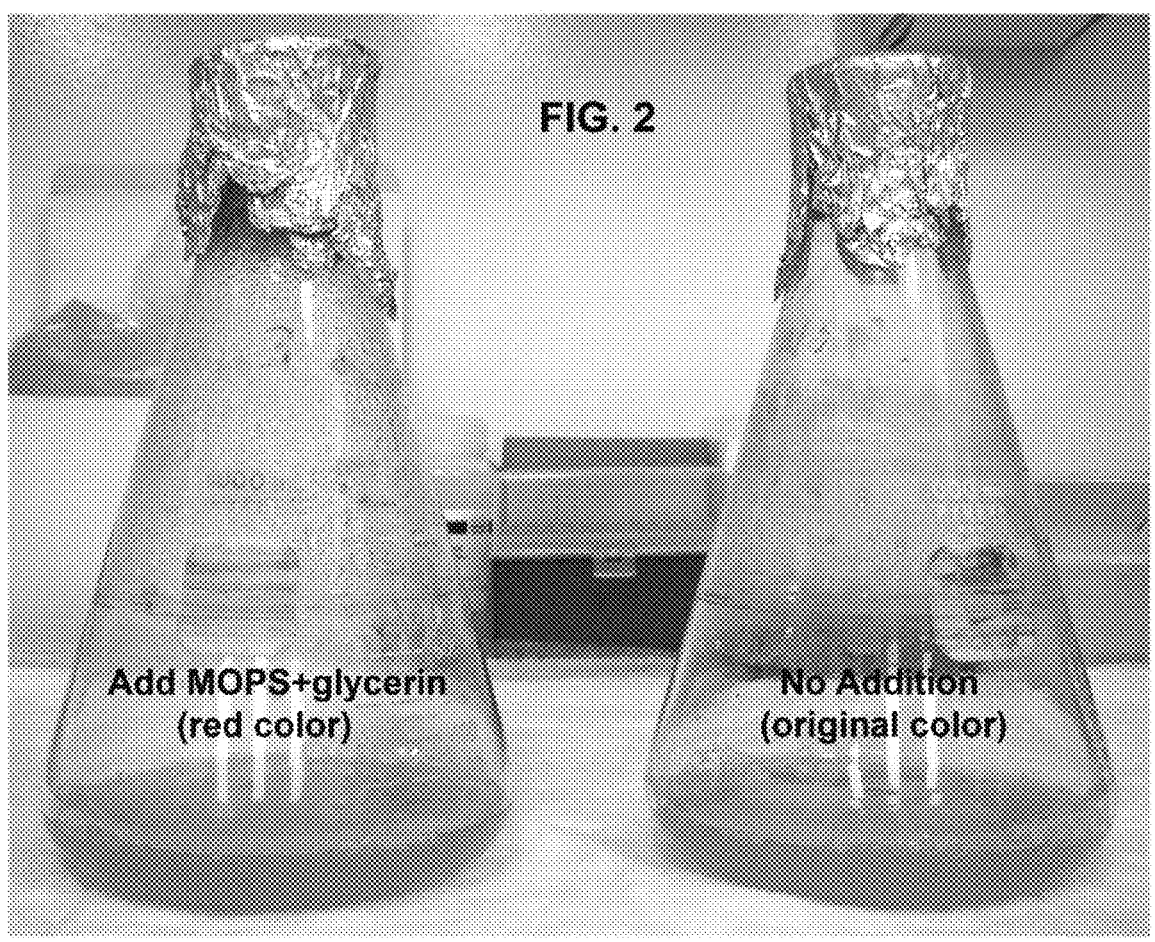
FIG. 2 depicts the results of *E. coli* culture broths treated with (left) or without (right) the mixture of about 0.1% (v/v) MOPS and about 0.05% (v/v) glycerin. The *E. coli* bacteria were transformed by pLenti-EF1alpha-RGFP-miR302 before treatments.
Figure 3:
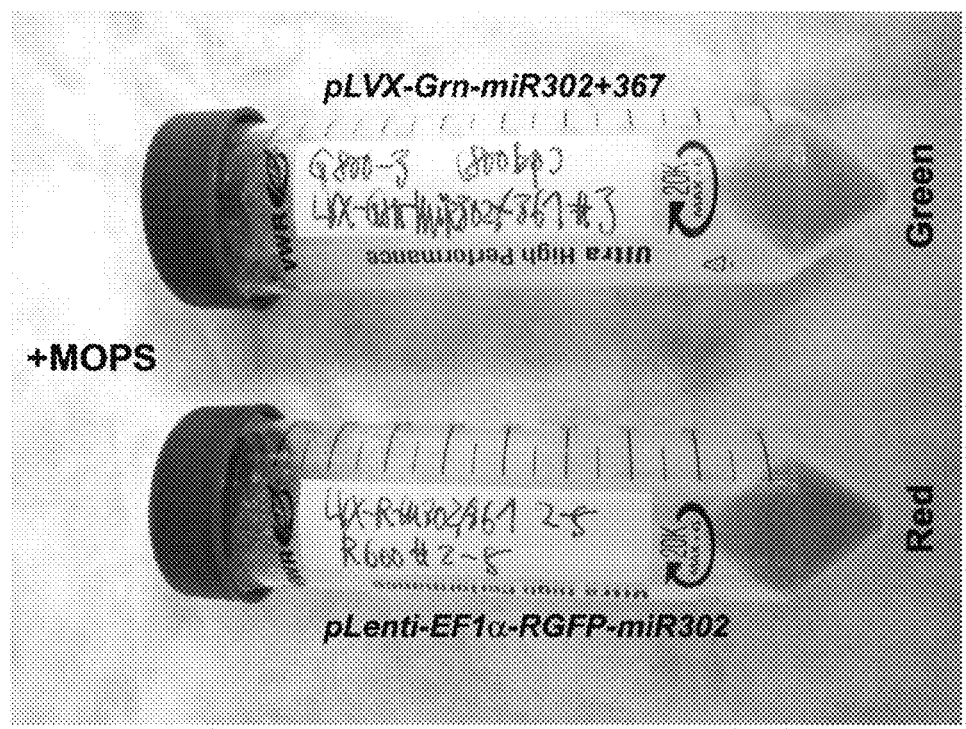
FIG. 3 shows the results of different bacterial pellets after treated with about 0.1% (v/v) MOPS. The *E. coli* bacteria were transformed by either pLVX-GFP-miR302+367 (green) or pLenti-EF1alpha-RGFP-miR302 (red) vector, respectively, before the MOPS treatment.
Figure 4:
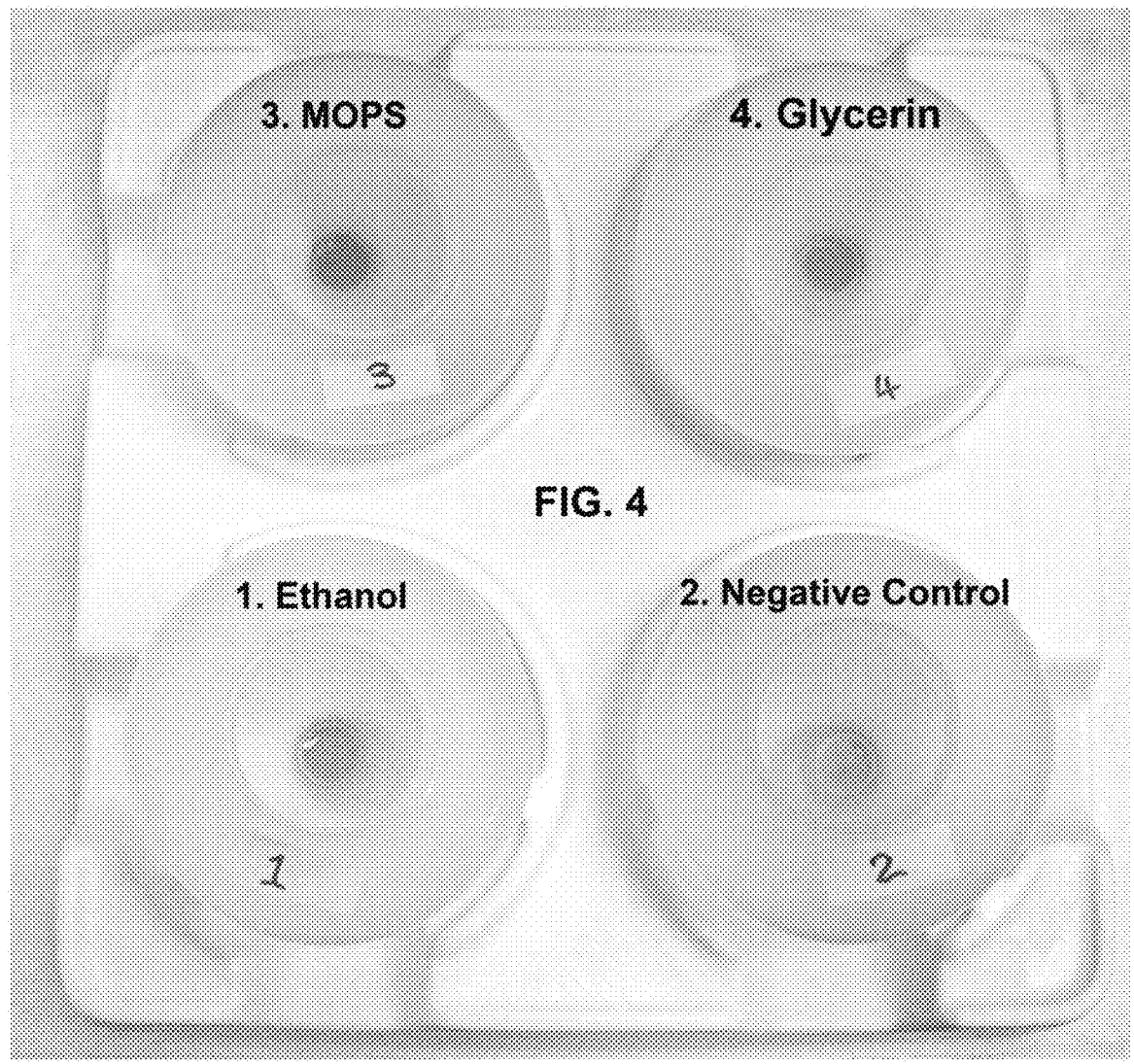

FIG. 4 shows the inducibility of different chemical inducers for stimulating EF1alpha and/or CMV promoter-driven gene expression in competent *E. coli* cells. Among all chemicals tested in the present invention, the top three most potent transcription inducers are MOPS, glycerin and ethanol. The inducer concentrations used can be ranged from about 0.001% to about 10%, most preferably, from about 0.05 to about 4%.

Figure 5:
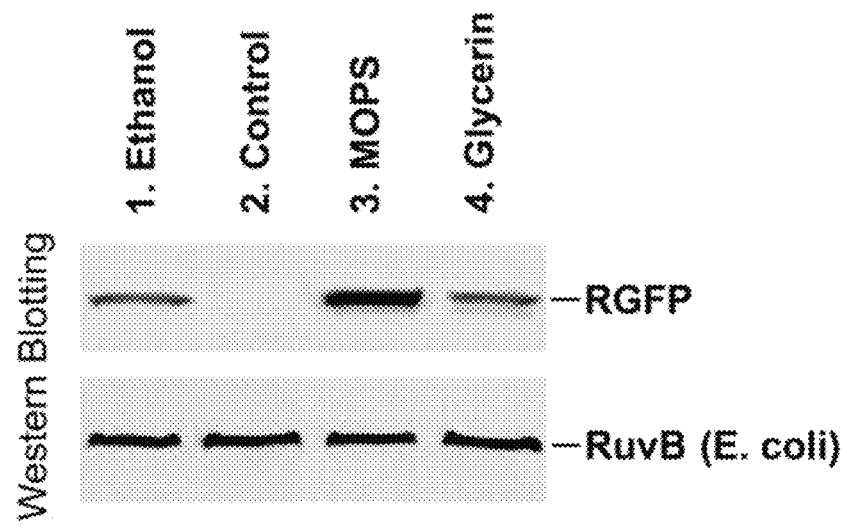

FIG. 5 shows the Western blotting results of red RGFP protein expression induced by MOPS, glycerin, and ethanol, respectively. Bacterial RuvB protein is used as a housekeeping standard to compare the levels of induced RGFP expression. Proteins and RNAs extracted from original *E. coli* cells without any vector transformation serve as negative controls.

Figure 6:
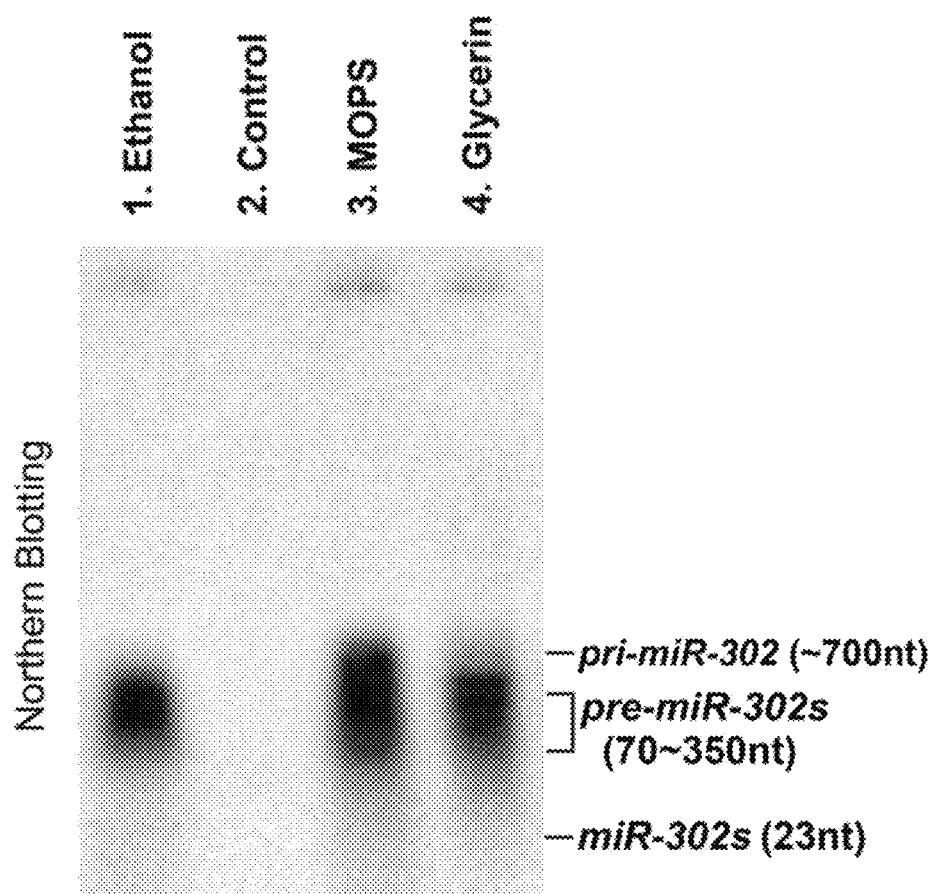

FIG. 6 shows the Northern blotting results of miR-302 and its pre-miRNA/pri-miRNA cluster expression induced by MOPS, glycerin, and ethanol, respectively. RNAs extracted from original *E. coli* cells without any vector transformation serve as negative controls.

Figure 7:
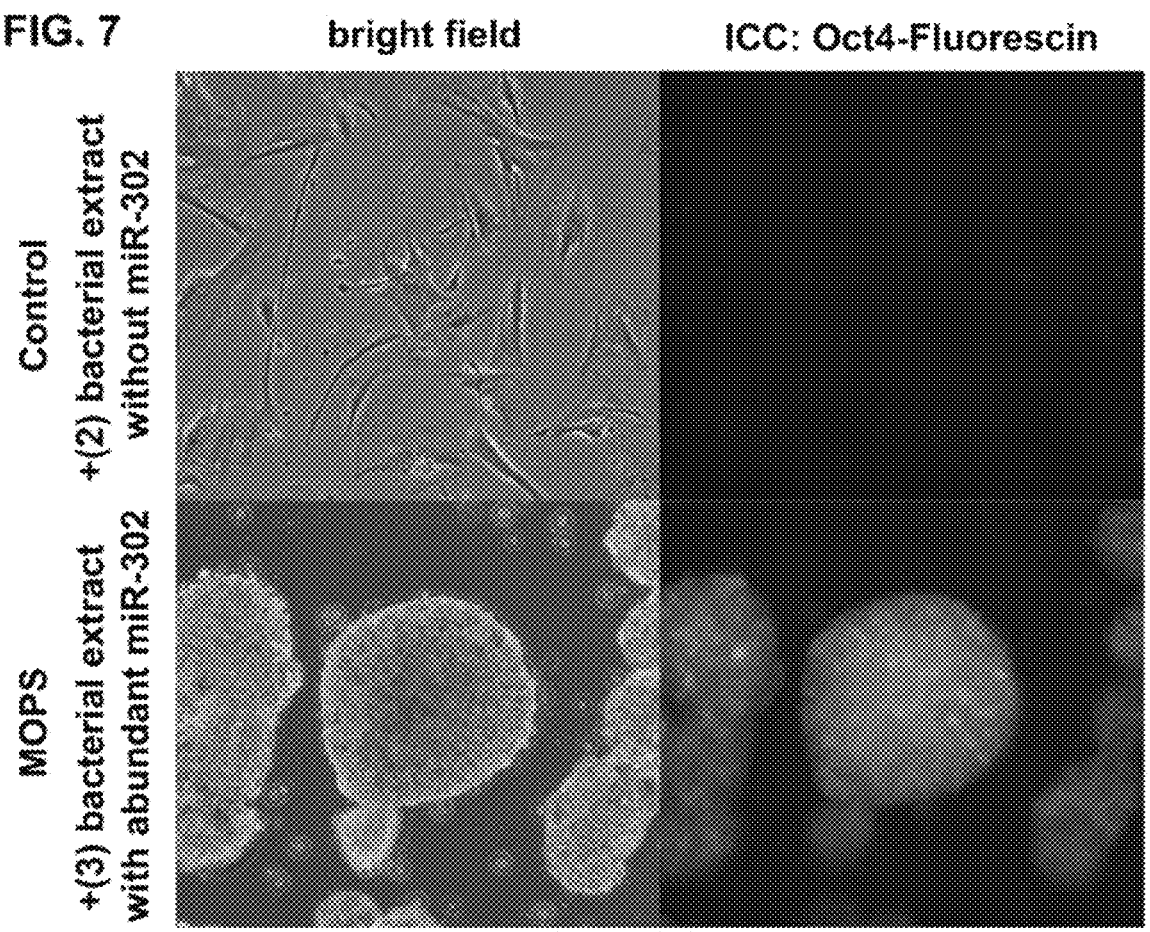

FIG. 7 shows iPS cell (iPSC) generation using miR-302 and pre-miR-302 isolated from bacterial extracts (BE), of which the miR-302/pre-miRNA expression has been confirmed by Northern blot analysis as shown in FIG. 6. As previously reported (Lin 2008, 2010, 2011), the miR-302-reprogrammed iPS cells (mirPSCs) form sphere-like cell colonies and express strong ESC marker Oct4 proteins (labeled by Oct4-promoter-driven green fluorescent protein expression).

Figure 8:
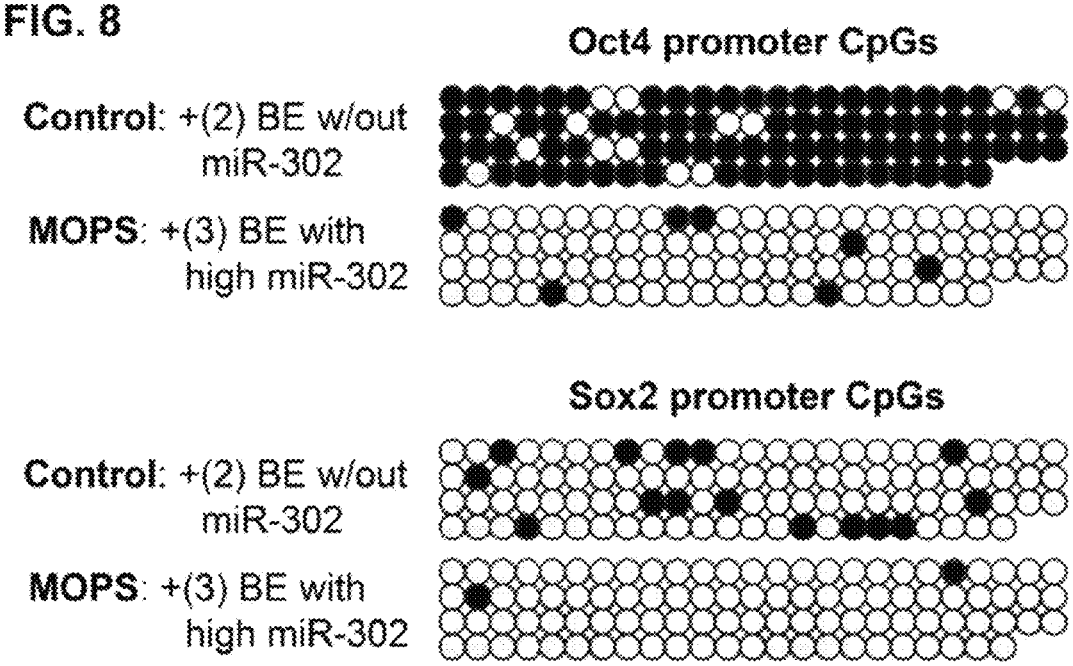

FIG. 8 shows the global DNA demethylation of Oct4 and Sox2 gene promoters induced by miR-302 and pre-miR-302 isolated from bacterial extracts (BE), of which the miR-302/pre-miRNA expression has been confirmed by Northern blot analysis as shown in FIG. 6. As reported by Simonsson and Gurdon (*Nat Cell Biol.* 6, 984-990, 2004), both events of global DNA demethylation and Oct4 expression are required for somatic cell reprogramming to form iPSCs.

FIGS. 9A and 9B show comparison of the healing results between untreated (9A) and miR-302-treated (9B) wounds in vivo. The isolated miR-302 molecules (20~400 µg/mL) were formulated with glycylglycerin and antibiotic ointment to form candidate drugs for testing topic treatments of large 2 cm×2 cm open wounds on pig back skins in vivo (n=6 for each group). After about two-week treatments (one treatment per day), the healed wounds were dissected and further made into tissue sections for histological examination under a microscope. The data showed that no or very little scar could be seen in the miR-302-treated wounds (9B top, n=6/6), whereas almost all untreated (treated with only antibiotic ointment) wounds contained large scars (9A top, n=5/6). Also, a significantly large amount of CD34-positive adult stem cell clusters (labeled by green fluorescent antibodies) were found in the miR-302-treated wounds (9B bottom, n=6/6), but not in untreated control wounds (9A bottom, n=0/6).

Figure 10A:
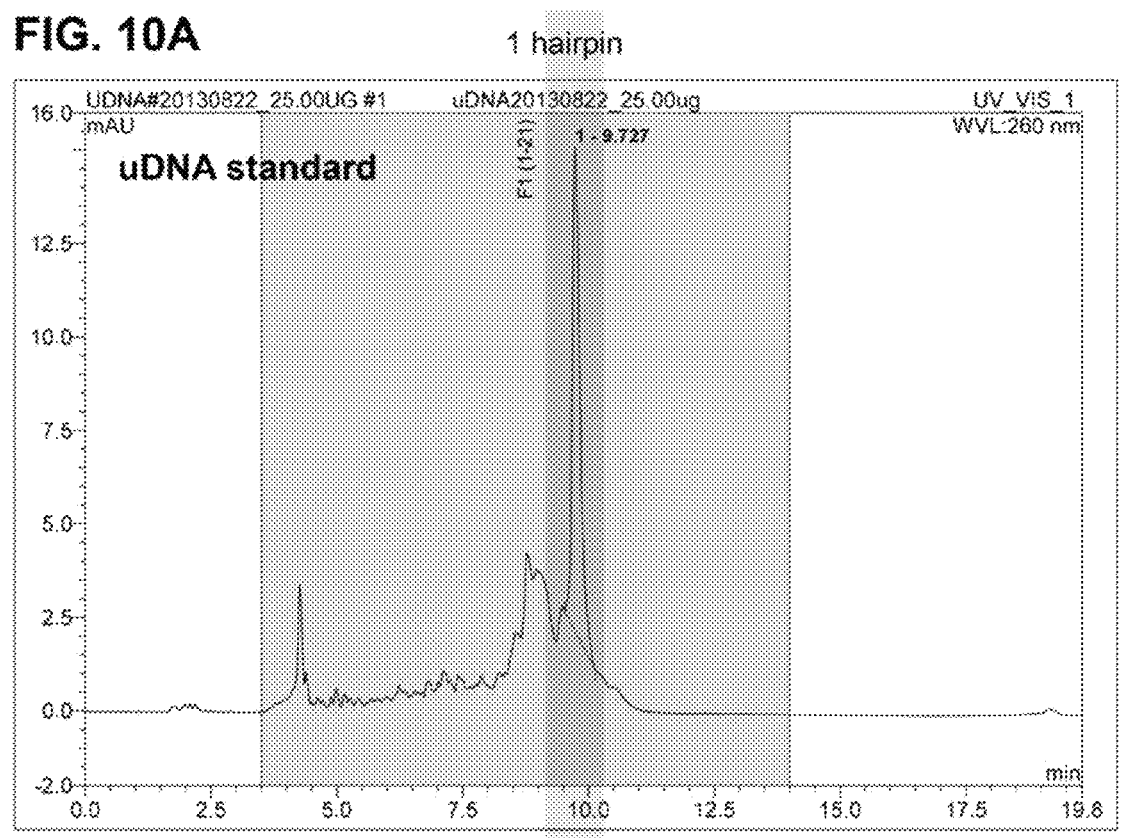
Figure 10B:
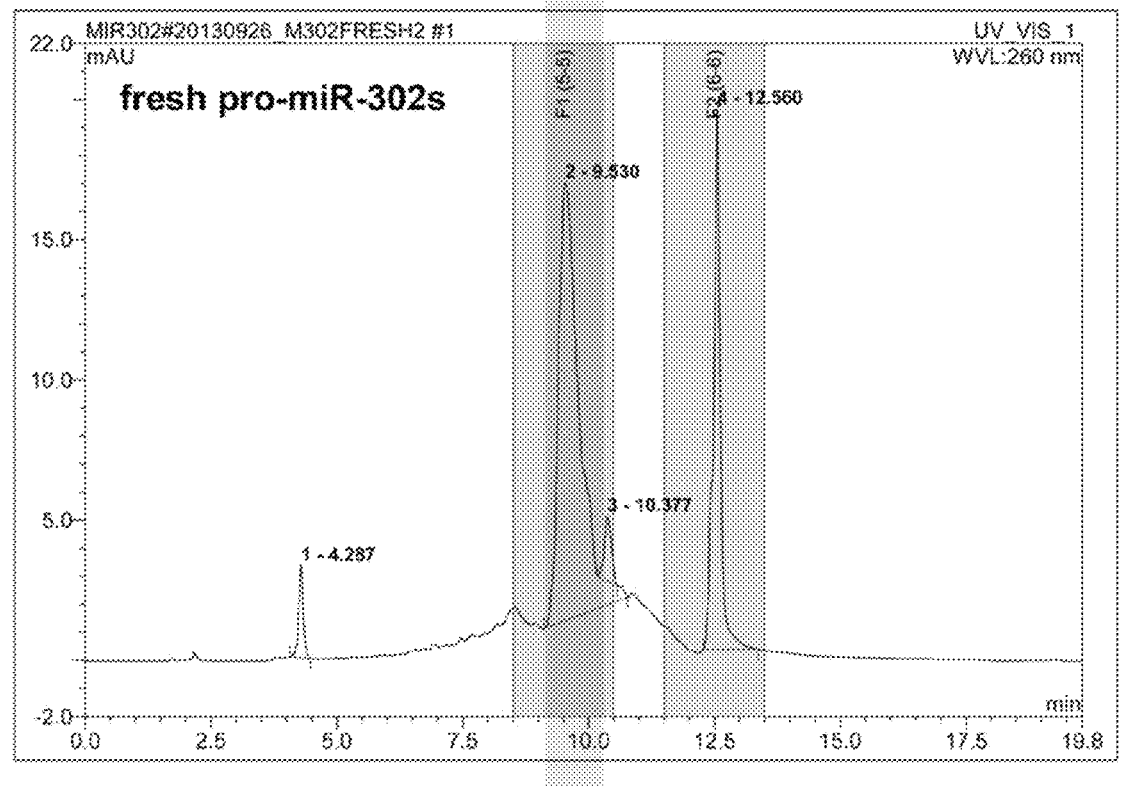

FIGS. 10A and 10B show the results of HPLC purification and analysis using a synthetic standard uDNA (made by Sigma-Genosys) and freshly extracted miR-302s/pre-miR-302s (or called pro-miR-302s) isolated from pLenti-EF1alpha-RGFP-miR302-transformed *E. coli* cells. The standard uDNA was designed to mimic a natural pre-miR-302a as: 5'-CCACCACUUA AACGUGGAUG UAC-UUGCUUU GAAACUAAAG AAGUAAGUGC UUC-CAUGUUU UGGUGAUGG-3' (SEQ.ID.NO.3).

Figure 11A:
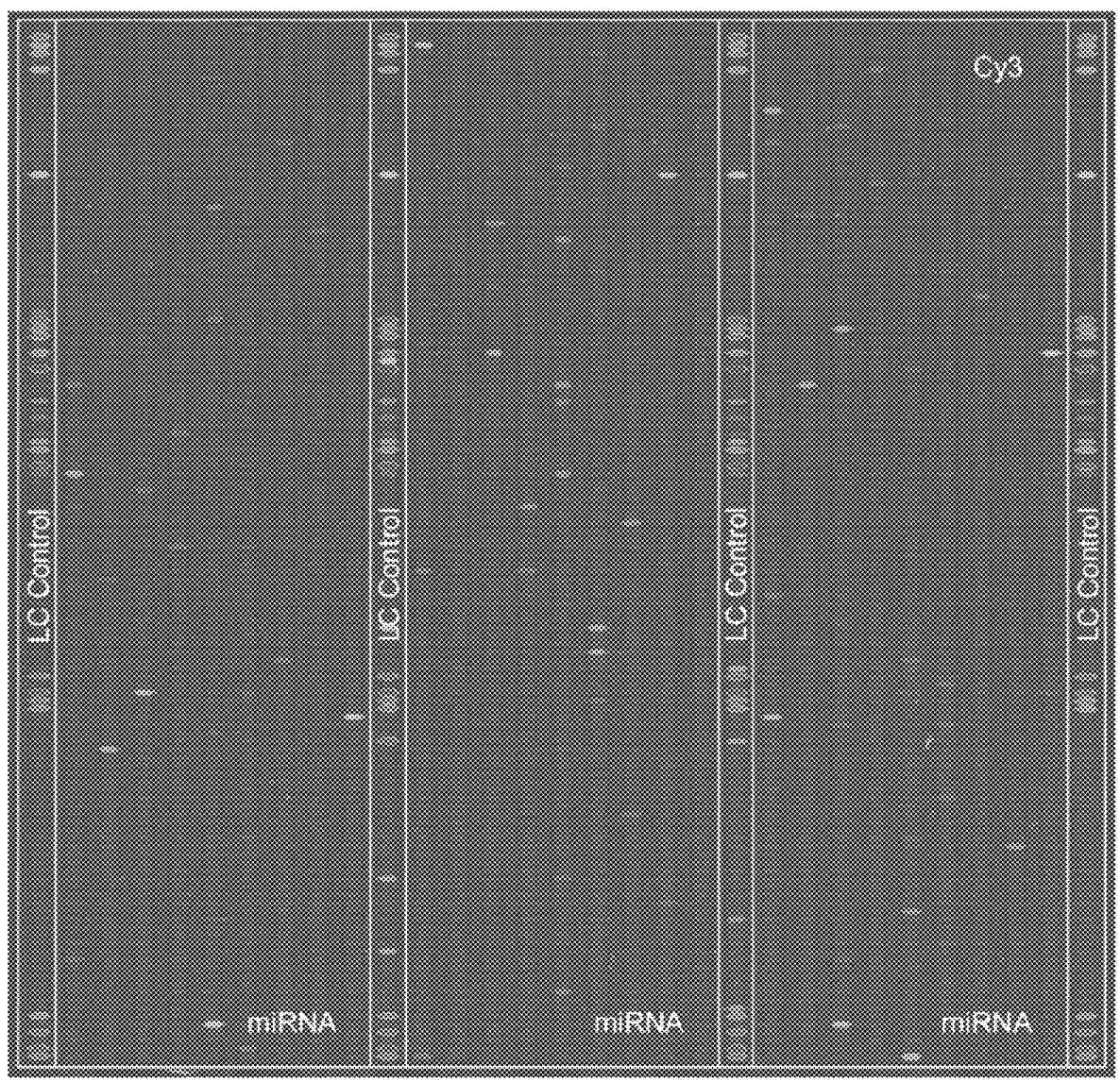
Figure 11B:
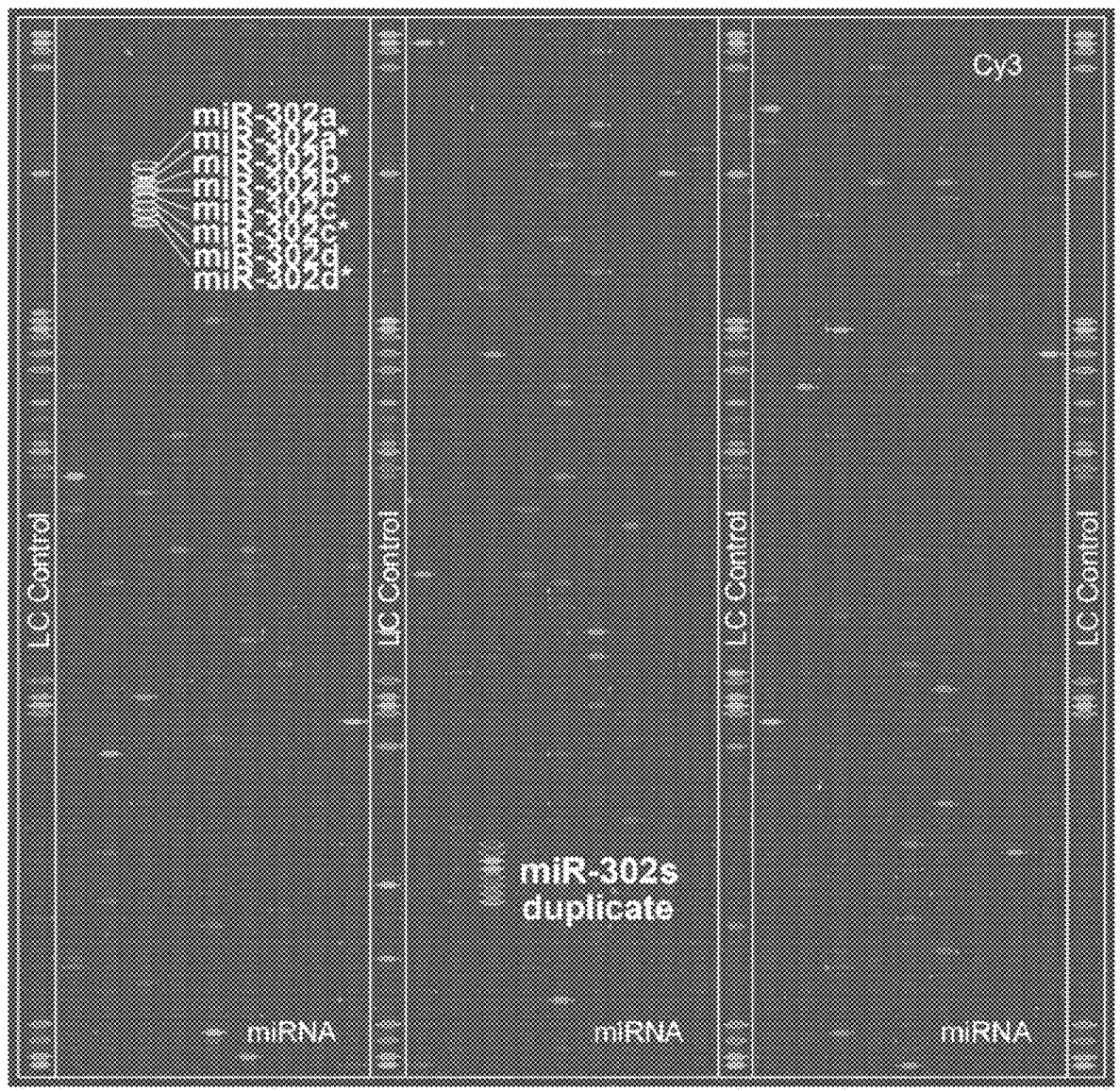
Figure 14A:
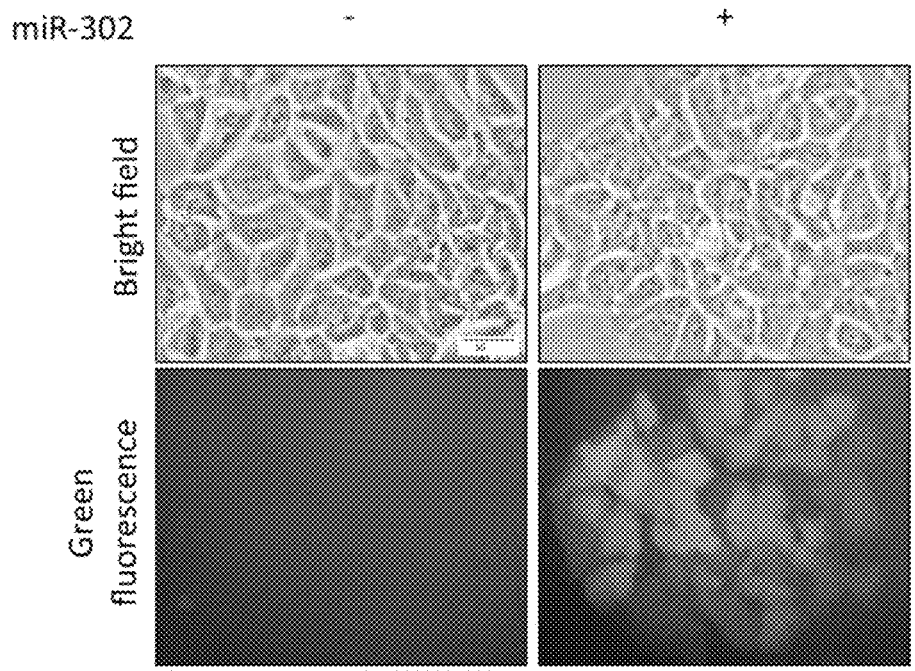
Figure 14B:
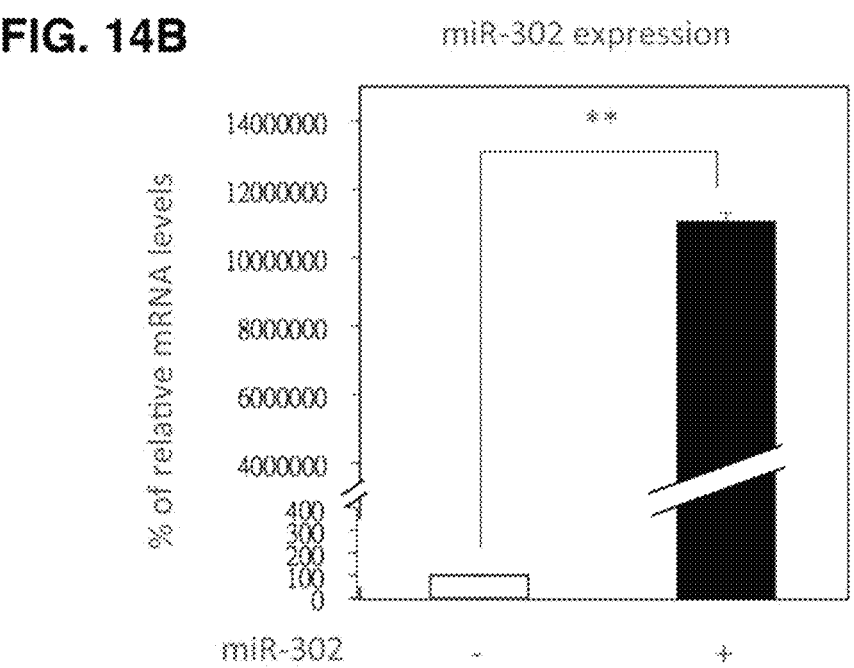
Figure 14C:
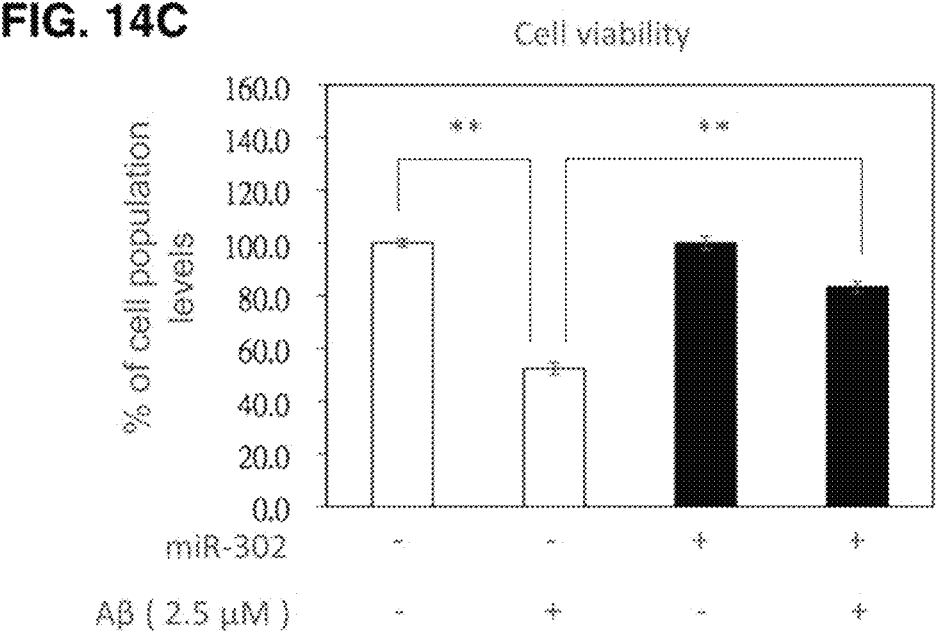
Figure 14D:
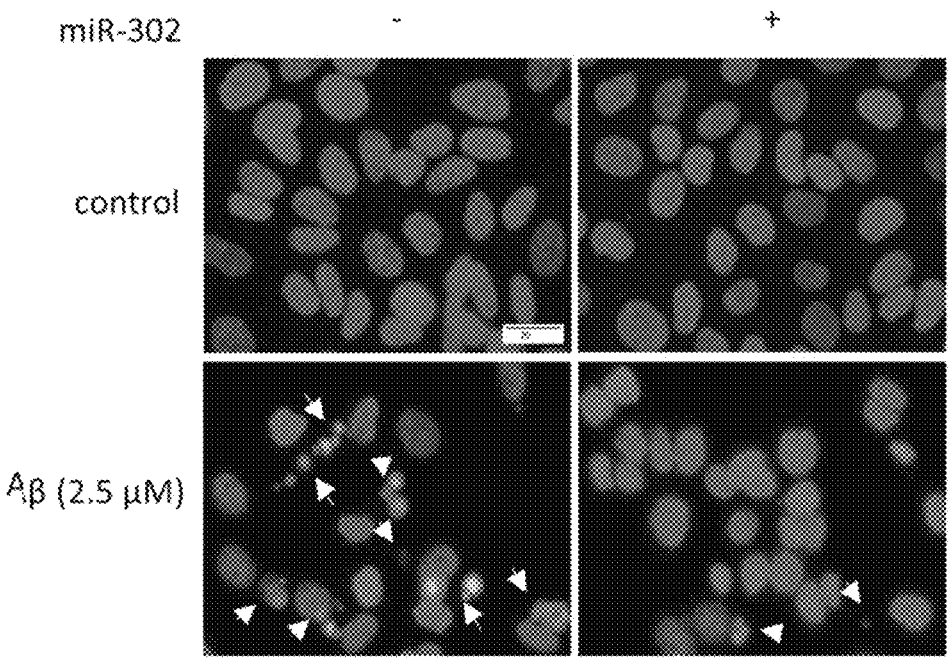
Figure 15A:
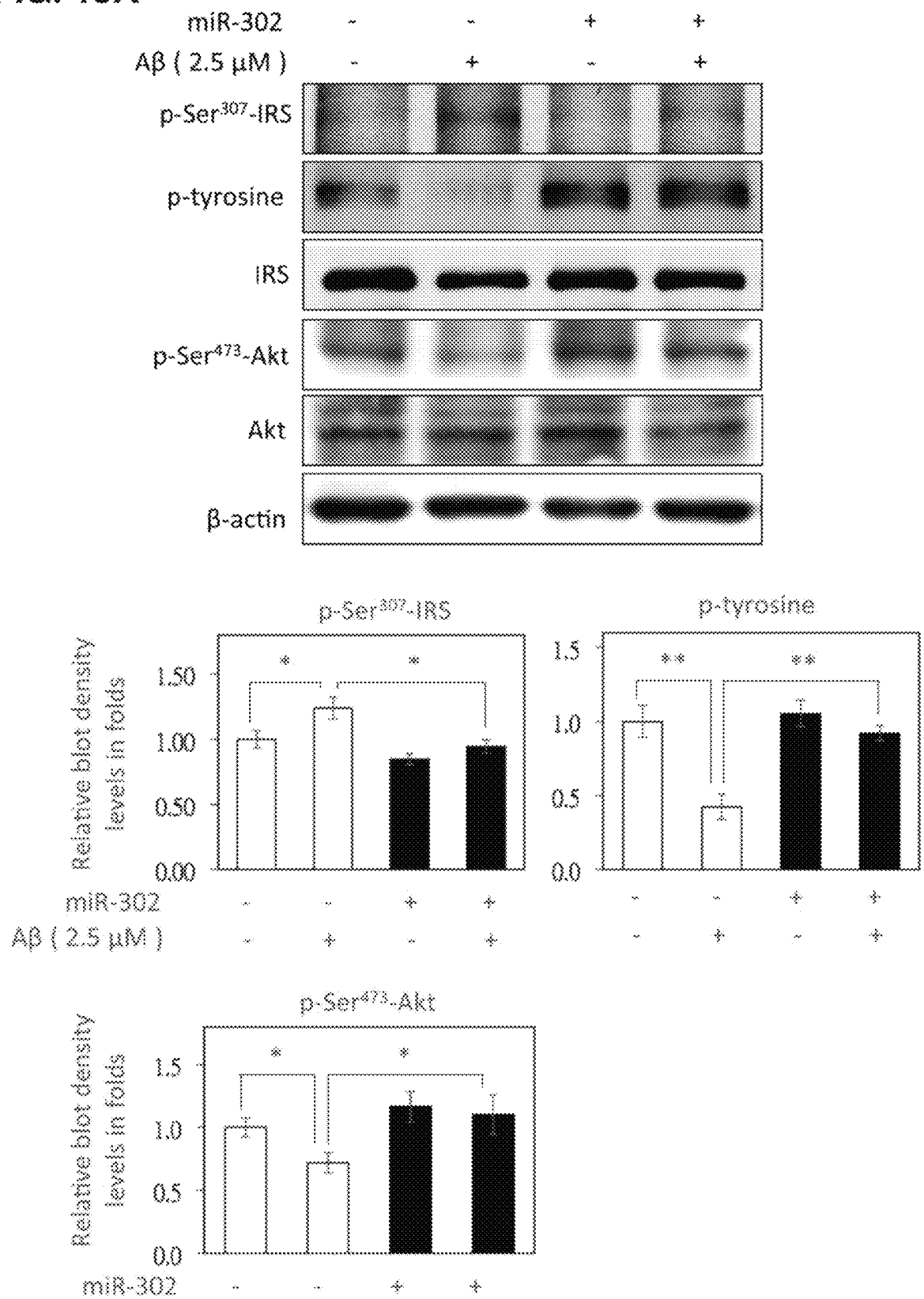
Figure 15B:
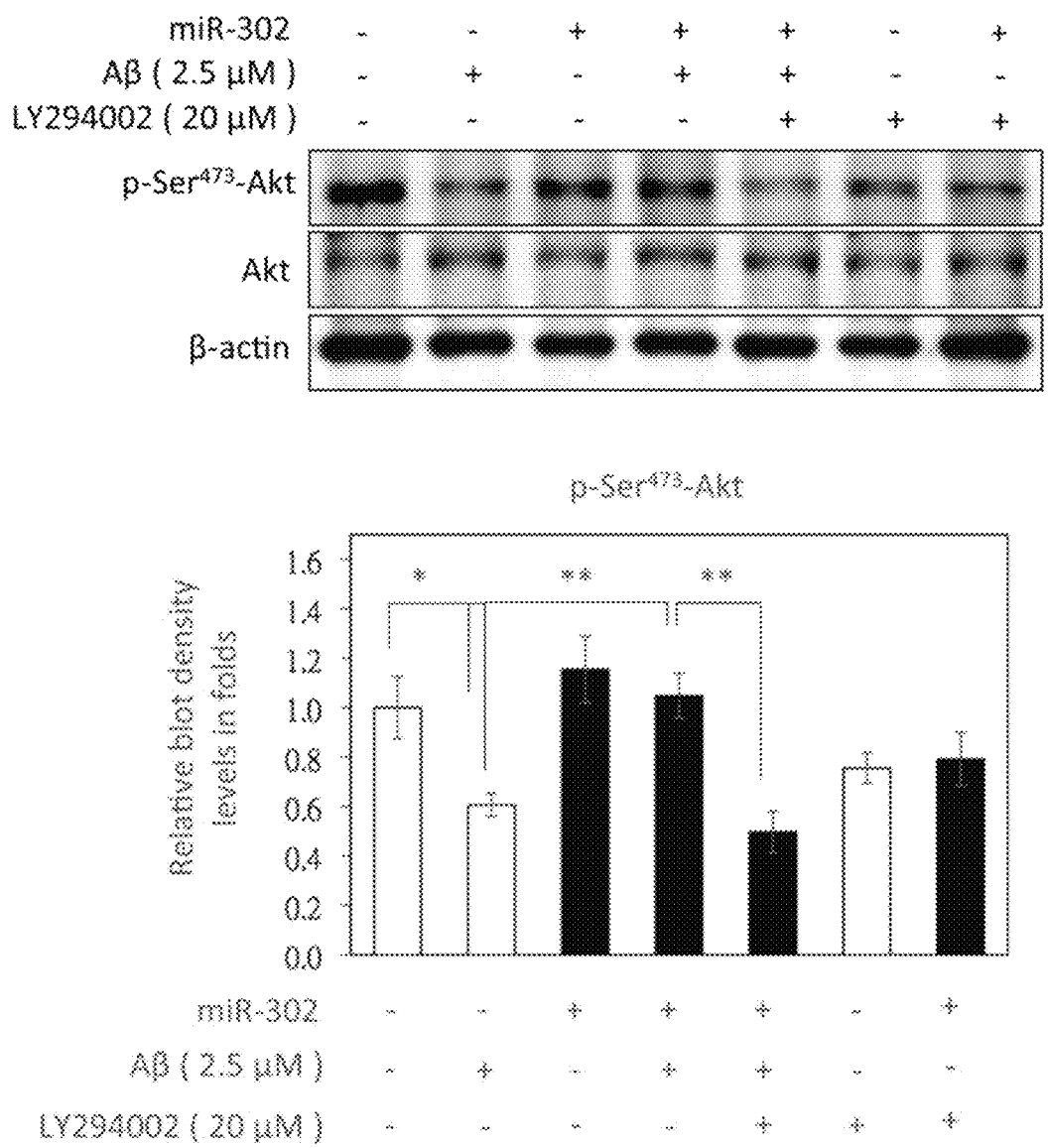
Figure 15C:
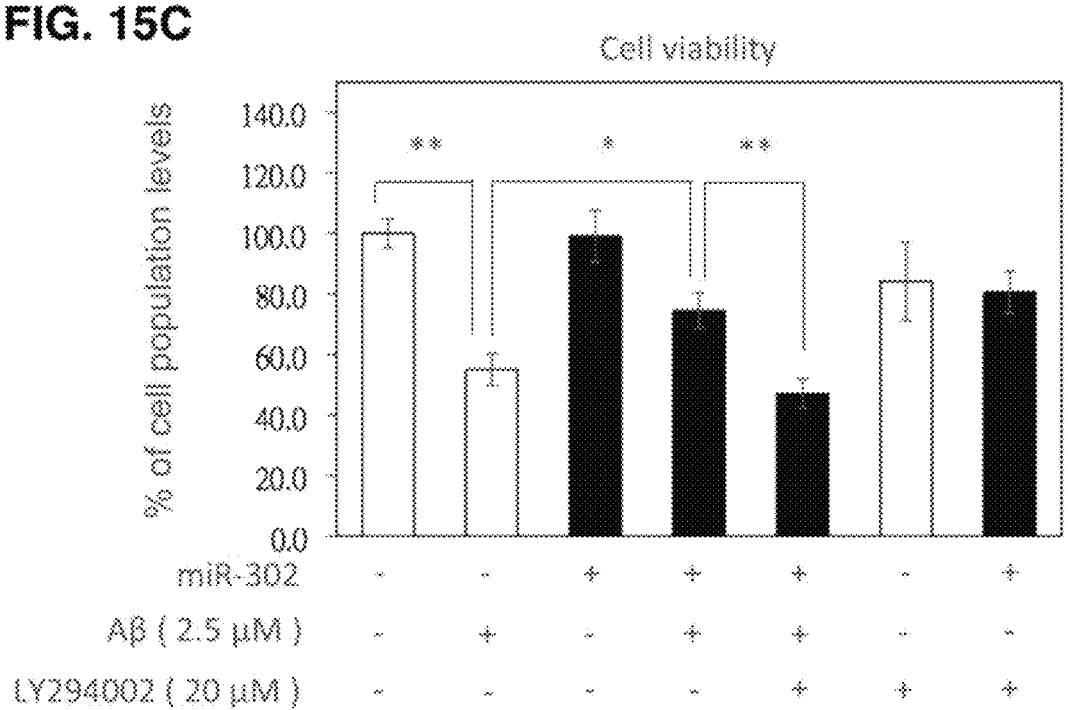
Figure 16E:
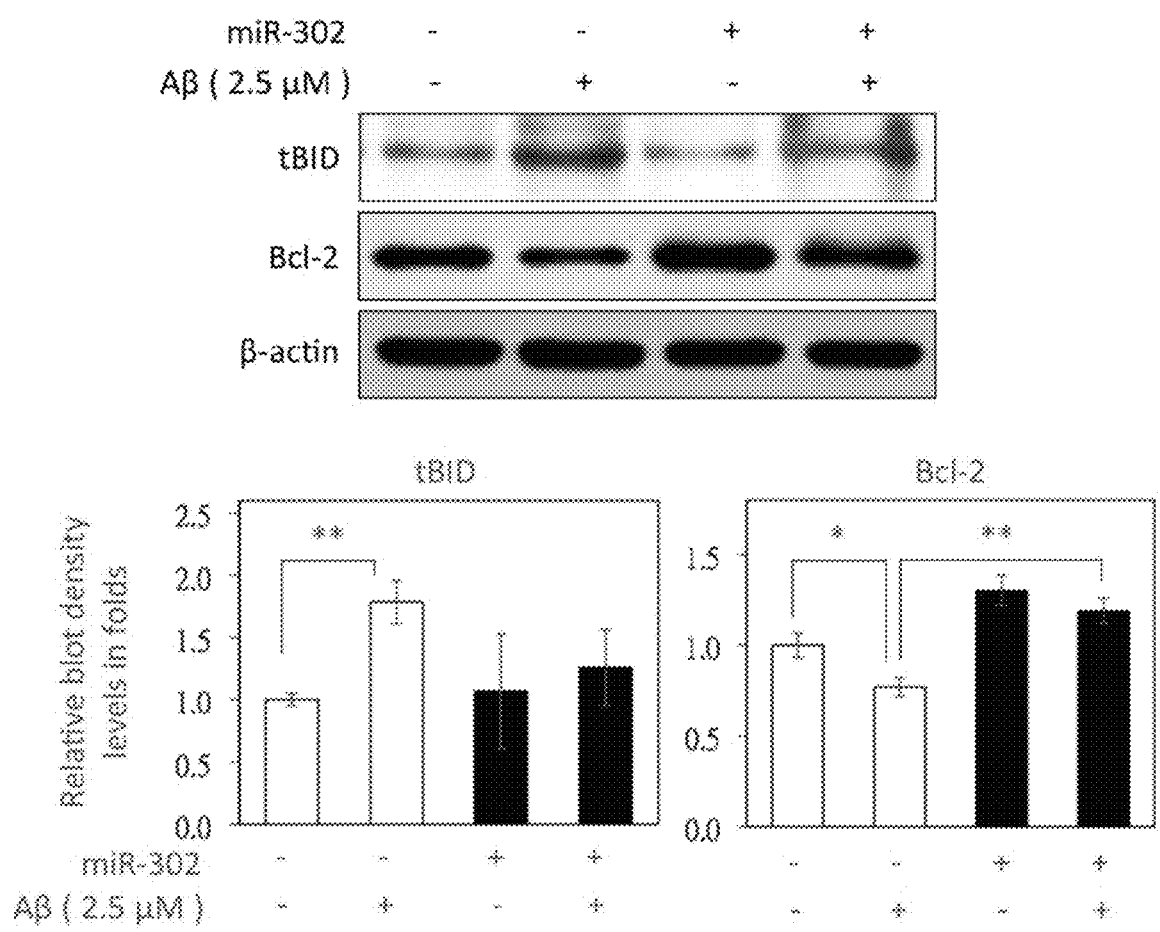
Figure 17A:
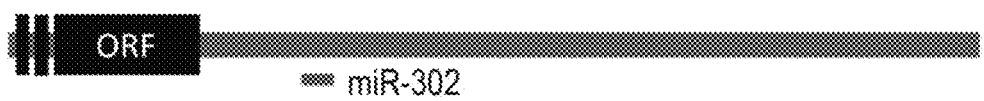
Figure 17B:
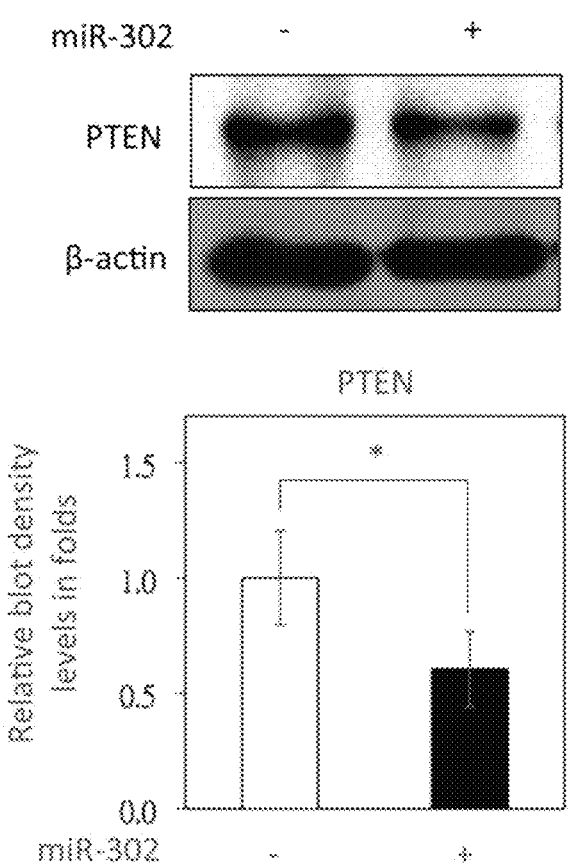
Figure 17D:
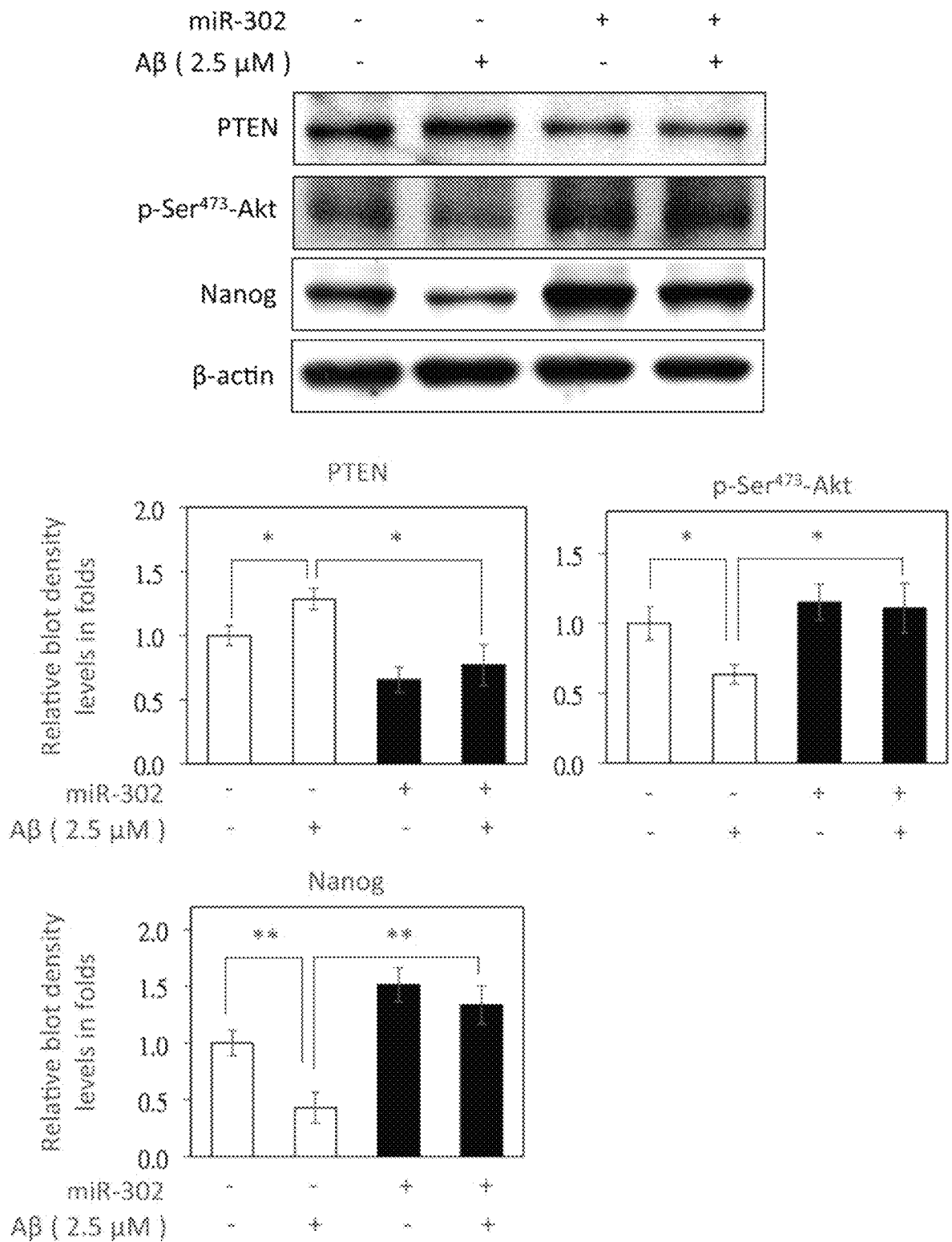
Figure 17E:
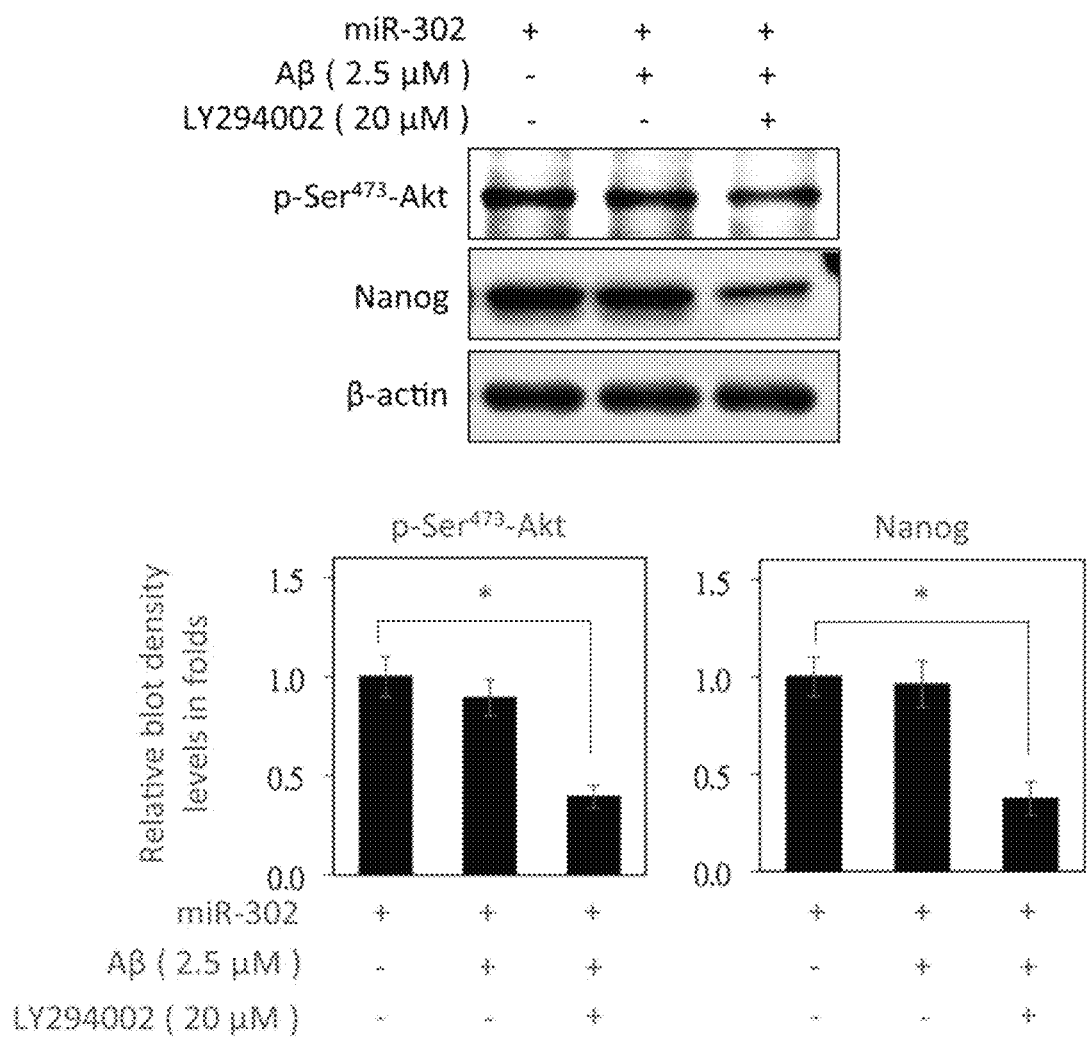
Figure 17F:
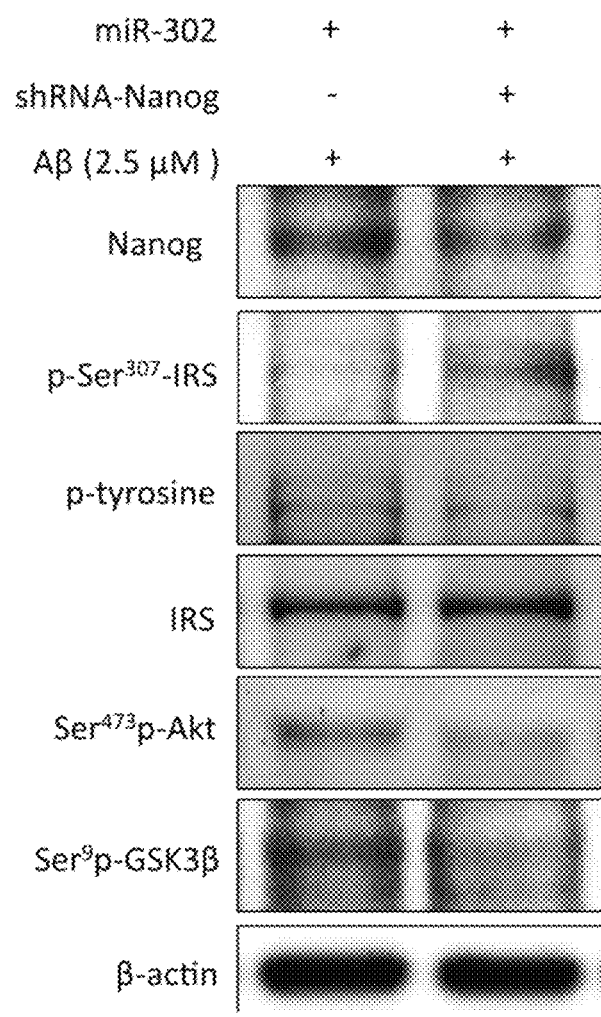
Figure 18A:
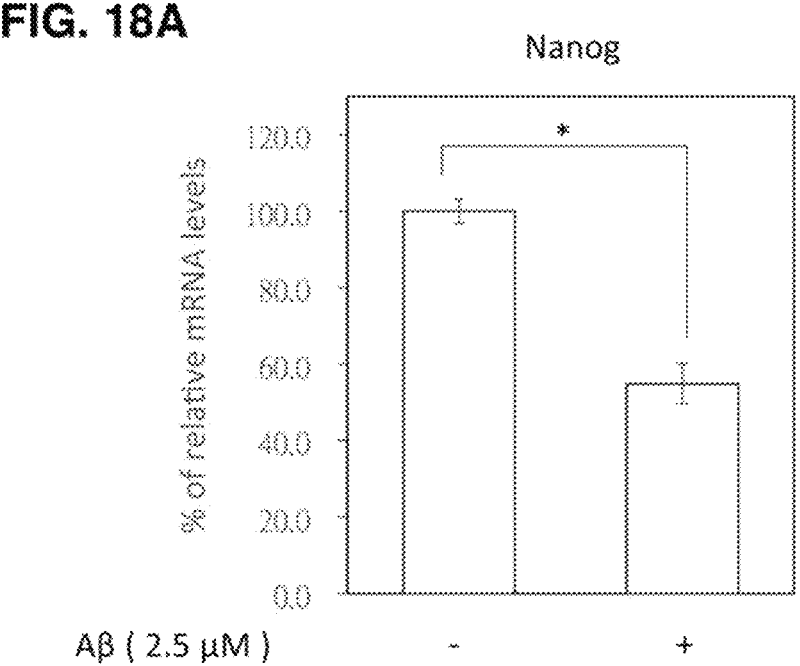
Figure 18B:
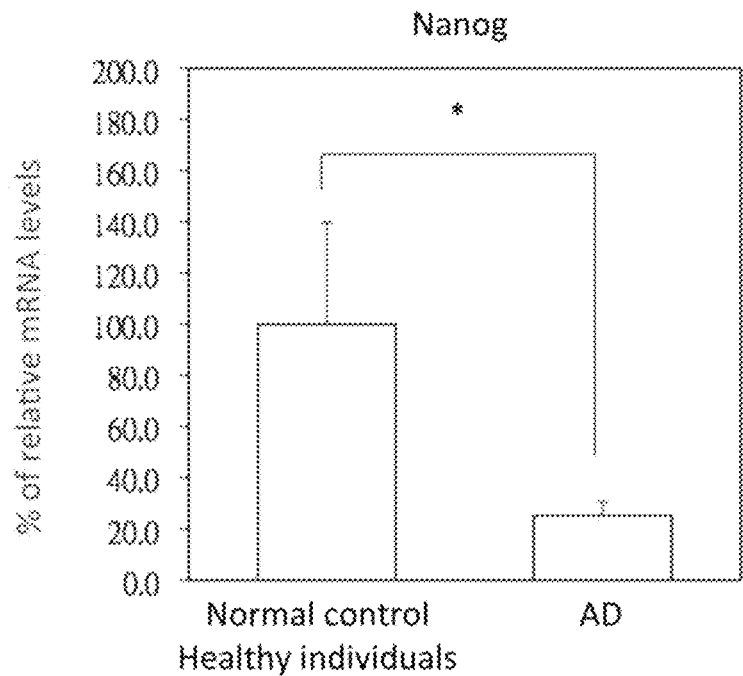
Figure 18C:
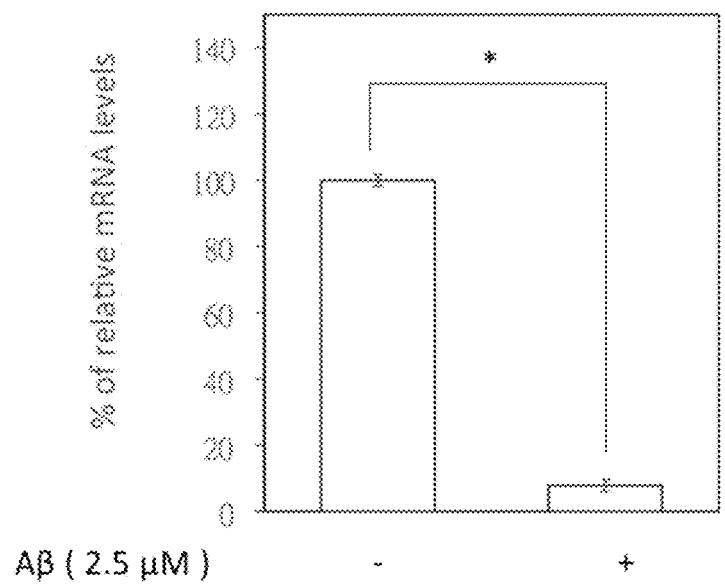
Figure 18D:
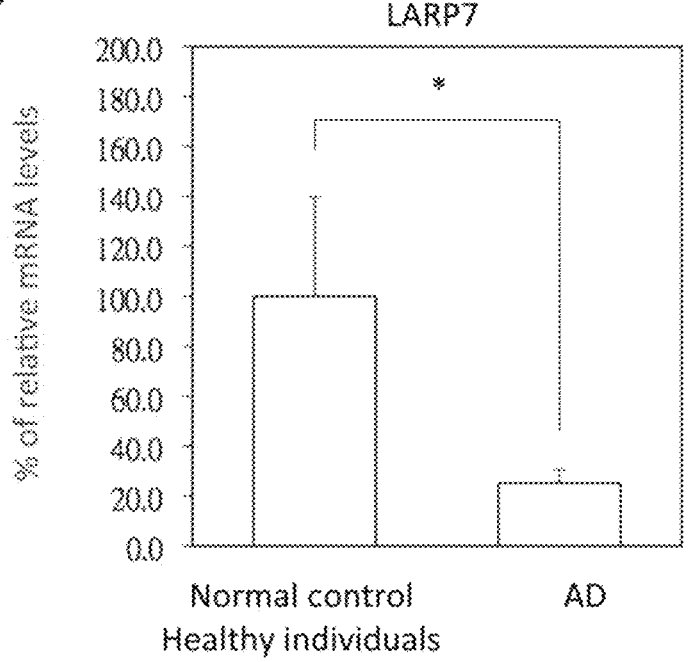

FIGS. 11A and 11B show the results of microRNA (miRNA) microarray analyses using small RNAs extracted from either blank *E. coli* competent cells or pLenti-EF1alpha-RGFP-miR302 (RGFP-miR302)-transformed/transfected cells. The extracted small RNAs were further purified by HPLC as shown in the green-labeled area of FIG. 10B. FIG. 11A shows that RNAs from blank *E. coli* cells present almost no microRNA (green dots mean non-statistically significant whereas red dots indicate positive results). This is because prokaryotes lack several essential enzymes required for microRNA expression and processing, such as Pol-2, Drosha and RNase III Dicer. Also, prokaryotic RNA polymerases do not transcribe small RNAs with high secondary structures, such as hairpin-like pre-miRNAs and shRNAs, which resemble intrinsic transcription termination signals in prokaryotes. As a result, only using the present invention, we can stimulate the expression of specific microRNAs, such as miR-302a, a*, b, b*, c, c*, d and d* as shown in FIG. 11B, in prokaryotic cells. Since prokaryotes do not possess Dicer, most microRNAs so obtained remain in their hairpin-like precursor conformations, such as pri-miRNA (4-hairpin cluster) and/or pre-miRNA (1 hairpin precursors).

FIG. 12 shows the lists of expressed microRNAs extracted from either blank *E. coli* cells (Group 1 as shown in FIG. 11A) or pLenti-EF1alpha-RGFP-miR302-transformed/transfected cells (Group 2 as shown in FIG. 11B). Signals less than 500 are not statistically significant (as shown in green in FIGS. 11A and 11B), which may be caused by either low copy number expression or high background.

FIGS. 13A and 13B show the sequencing results of the miR-302 familial cluster (13A) and the individual pro-miR-302a, pro-miR-302b, pro-miR-302c, and pro-miR-302d sequences (13B). The result of the whole miR-302 familial cluster transcript (=pri-miR-302) is (SEQ.ID.NO. 2)
5'-AAUUUUUUUC UUCUAAAGUU AUGCCAUUUU GUUUUCUUUC

UCCUCAGCUC UAAAUACUCU GAAGUCCAAA GAAGUUGUAU

GUUGGGUGGG CUCCCUUCAA CUUUAACAUG GAAGUGCUUU

CUGUGACUUU AAAAGUAAGU GCUUCCAUGU UUUAGUAGGA

GUGAAUCCAA UUUACUUCUC CAAAAUAGAA CACGCUAACC

UCAUUUGAAG GGAUCCCCUU UGCUUUAACA UGGGGGUACC

UGCUGUGUGA AACAAAAGUA AGUGCUUCCA UGUUUCAGUG

GAGGUGUCUC CAAGCCAGCA CACCUUUUGU UACAAAAUUU

-continued
UUUUGUUAUU GUGUUUUAAG GUUACUAAGC UUGUUACAGG

UUAAAGGAUU CUAACUUUUU CCAAGACUGG GCUCCCCACC

ACUUAAACGU GGAUGACUU GCUUUGAAAC UAAAGAAGUA

AGUGCUUCCA UGUUUUGGUG AUGGUAAGUC UUCUUUUUAC

AUUUUUAUUA UUUUUUUAGA AAAUAACUUU AUUGUAUUGA

CCGCAGCUCA UAUAUUUAAG CUUUAUUUUG UAUUUUUACA

UCUGUUAAGG GGCCCCCUCU ACUUUAACAU GGAGGCACUU

GCUGUGACAU GACAAAAAUA AGUGCUUCCA UGUUUGAGUG

UGGUGGUUCC UACCUAAUCA GCAAUUGAGU UAACGCCCAC

ACUGUGUGCA GUUCUUGGCU ACAGGCCAUU ACUGUUGCUA-3', while the individual sequences of pro-miR-302a, pro-miR-302b, pro-miR-302c, and pro-miR-302d are as follows: 5'-CCACCACUUA AACGUGGAUG UACUUGCUUU GAAACUAAAG AAGUAAGUGC UUCCAUGUUU UGGUGAUGG-3' (SEQ.ID.NO.3), 5'-GCUCCCUUCA ACUUUAACAU GGAAGUGCUU UCUGUGACUU UAAAAGUAAG UGCUUCCAUG UUUUAGUAGG AGU-3' (SEQ.ID.NO.4), 5'-CCUUUGCUUU AACAUGGGGG UACCUGCUGU GUGAAACAAA AGUAAGUGCU UCCAUGUUUC AGUGGAGG-3' (SEQ.ID.NO.5), and 5'-CCUCUACUUU AACAUGGAGG CACUUGCUGU GACAUGACAA AAAUAAGUGC UUCCAUGUUU GAGUGUGG-3' (SEQ.ID.NO.6), respectively.

FIGS. 14A-14F show that treatments of miR-302 inhibit Aβ-induced apoptosis in human SK-N-MC neuronal cells. (14A) Transfection of SK-N-MC cells with either the pLVX-Grn-miR302 vector (black bar, to form miR-302-overexpressed cells) or an empty vector (white bar, to serve as control cells), using a lipofectamine 2000 reagent. Positively transfected cells were detected by co-expression of a green fluorescent protein (AcGFP) under an inverted fluorescent microscope. (14B) RT-qPCR analyses of miR-302 expression using total RNA samples extracted from miR-302-transfected (black bar) or control (white bar) cells, respectively. The detected miR-302 expression levels in transfected cells were normalized with the levels of control cells (n=3, $p<0.01$). (14C) Cell viability was determined by MTT assays. Cells were seeded in 24-welled plates overnight and then treated with 2.5 μM Aβ for 24 hours. The results of cell viability were normalized using the level of control cells, showing that ectopic miR-302 expression significantly reduced Aβ-induced cell death. (14D) Morphological changes of nuclear chromatins during apoptosis were observed under fluorescent microscopy with DAPI staining. Cells were cultivated on coated slides and treated with 2.5 μM Aβ for 24 hours. The nuclei fragmentation was labeled (white arrow) and was quantified by counting four random fields per condition (14E). (14F) Aβ-induced cell apoptosis was determined by western blotting of Caspase 3 and PARP cleavage after Aβ treatment (2.5 μM Aβ for 24 hours). The results were normalized with the density levels of control cells, showing markedly attenuated Aβ-induced cell apoptosis in miR-302-transfected cells (n=3, $p<0.01$). (Aβ, amyloid-β; +, with treatment; -, without treatment. All values were presented as mean±S.E.M. Significant differences were determined by multiple comparisons using Dunnett's post-hoc trest for *$p<0.05$ and **$p<0.01$.)

FIGS. 15A-15D show that ectopic miR-302 expression activates Akt signaling and hence diminishes Aβ-induced cytotoxicity. (15A) Western blot analyses of pSer307-IRS-1, pTyr-IRS-1, and pSer473-Akt expressions 24 hours after Aβ treatment (2.5 μM), showing marked elevation of pSer307-IRS-1 (n=3, p<0.01) as well as reduction of both pTyr-IRS-1 and pSer473-Akt levels (n=3, p<0.05) in control groups compared to those of miR-302-transfected cells. (15B) Western blot analysis of pSer473-Akt levels after treatments of 2.5 μM Aβ or 20 μM LY294002, or both for 24 hours. (15C) Cell viability in response to the treatments of (15B), as determined by MTT assays. (15D) Western blot measurement of pSer9-GSK3β, and pThr231-tau levels in response to the treatments of miR-302s (15B), showing that miR-302 could stimulate Akt signaling to counteract Aβ-mediated cytotoxicity, resulting in a marked increase of GSK3β Ser9 phosphorylation and decrease of tau-Thr231 phosphorylation (n=3, p<0.05). Yet, further co-treatment of Aβ (2.5 μM) and LY294002 (20 μM) abolished all these protective effects of Akt signaling in miR-302-transfected cells (n=3, p<0.05). (Aβ, amyloid-β; +, with treatment; −, without treatment. All values were presented as mean±S.E.M. Significant differences were determined by multiple comparisons using Dunnett's post-hoc trest for *p<0.05 and **p<0.01.)

FIGS. 16A-16E show that miR302-induced Akt signaling activation attenuates Aβ-induced oxidative stress. (16A) Intracellular superoxide radical anions stained with DHE were detected by fluorescence microscopy. Cells were treated with 2.5 μM Aβ or 1 μM insulin, or both, for 2 hours and then analyzed with DHE staining. The intensity of red fluorescent dye was normalized with the level of control cells before comparison. (16B) After 24-hour Aβ treatment (2.5 μM), western blot analyses showed that the expression of Nrf2 and HO-1 were decreased in control cells compared to those of miR-302-transfected cells (n=3, p<0.05). (16C) Cells were treated with 2.5 μM Aβ in the presence of 1 μM insulin or 20 μM LY294002, or both, and then analyzed with western blotting for Nrf2. As shown, co-treatment of Aβ and LY294002 inhibited Nrf2 expression (n=3, p<0.05), whereas further treatment with insulin (1 μM) prevented this inhibitory effect on Nrf2 expression (n=3, p<0.05). (16D) Cells of (16C) were further stained with JC-1 dye and observed under an inverted fluorescent microscope, showing that Aβ treatment reduced the intensity of JC-1 green fluorescence in miR-302-transfected cells (n=3, p<0.05), while further treatment of LY294002 (20 μM) prevented this effect. (16E) Western blotting analyses showing that a significant increase of tBid and decrease of Bcl-2 were observed in control cells compared to miR-302-transfected cells after 24-hour Aβ treatment (2.5 μM). (Aβ, amyloid-β; +, with treatment; −, without treatment. For fluorescent density quantification, the levels of tested cells were normalized with that of control cells before comparison. Values were presented as mean±S.E.M. Significant differences were determined by multiple comparisons using Dunnett's post-hoc trest for *p<0.05 and **p<0.01.)

FIGS. 17A-17F show that miR-302 targets PTEN and upregulates Nanog through Akt signaling. (17A) Alignment of predicted miR-302 binding sites within human PTEN 3'UTR was shown. (17B and 17C) Cells lysates were obtained from untreated control cells and miR-302-transfected cells, respectively, and further analyzed with western blotting for PTEN and Nanog, showing the downregulation of PTEN and upregulation of Nanog in miR-302-transfected cells (n=3, p<0.05). (17D) Western blot analyses of PTEN, pSer473 Akt, and Nanog expressions after 24-hour Aβ treatment (2.5 μM), showing an increase of PTEN (p<0.05) and decreases of pSer473 Akt (p<0.05) and Nanog in control cells (n=3, p<0.01) compared to those of miR-302-transfected cells (n=3, p<0.05). (17E) Western blot analyses of pSer473 Akt and Nanog expressions 24 hours after treatment of Aβ (2.5 μM) or LY294002 (20 μM), or both, showing that both pSer473 Akt and Nanog were significantly decreased in miR-302-transfected cells treated with both Aβ and LY294002 (n=3, p<0.05). (17F) The miR-302-transfected cells were transiently transfected with shRNA-Nanog, and then treated with Aβ (2.5 μM) for 24 hours. shRNA-directed knockdown of Nanog markedly elevated pSer307-IRS-1 and reduced the levels of pTyr-IRS-1, pSer473-Akt and pSer9-GSK3β expressions in miR-302-transfected cells compared to those of control cells treated with Aβ alone. (Aβ, amyloid-β; shRNA-Nanog, shRNA gene silencer directed against human Nanog. +, with treatment; −, without treatment. The results of density quantification were normalized with the level of control cells. Values were presented as mean±S.E.M. Significant differences were determined by multiple comparisons using Dunnett's post-hoc trest for *p<0.05 and **p<0.01.)

FIGS. 18A-18D show that Comparison of the expression levels of Naong and LARP7 mRNAs in vitro and in vivo after miR-302 treatments. (18A) After 24-hour Aβ treatment (2.5 μM), the expression of Nanog mRNA was markedly decreased in control cells in vitro (n=3, p<0.05). (18B) Both AD patients' (n=7) and normal age-matched individual's (n=6) blood samples were collected, separately, and total RNAs were then extracted and used for RT-qPCR analyses. The results showed that AD patients' PBMCs express significantly lower Nanog mRNAs than that of normal individuals (p<0.05). (18C) Following 24-hour Aβ treatment (2.5 μM), the expression of LARP7 mRNA was markedly reduced in control cells compared to that of miR-302-transfected cells in vitro (n=3, p<0.05). (18D) AD patients' PBMCs expressed significantly lower LARP7 mRNA levels than that of normal individuals (p<0.05). (Aβ, amyloid-β; AD, Alzheimer diseases. Levels of mRNA expression were normalized with the levels of control cells or normal healthy individuals. Values were presented as mean±S.E.M. Significant differences were determined by using multiple comparisons of Dunnett's post-hoc trest for *p<0.05 and **p<0.01.)

Figure 19:
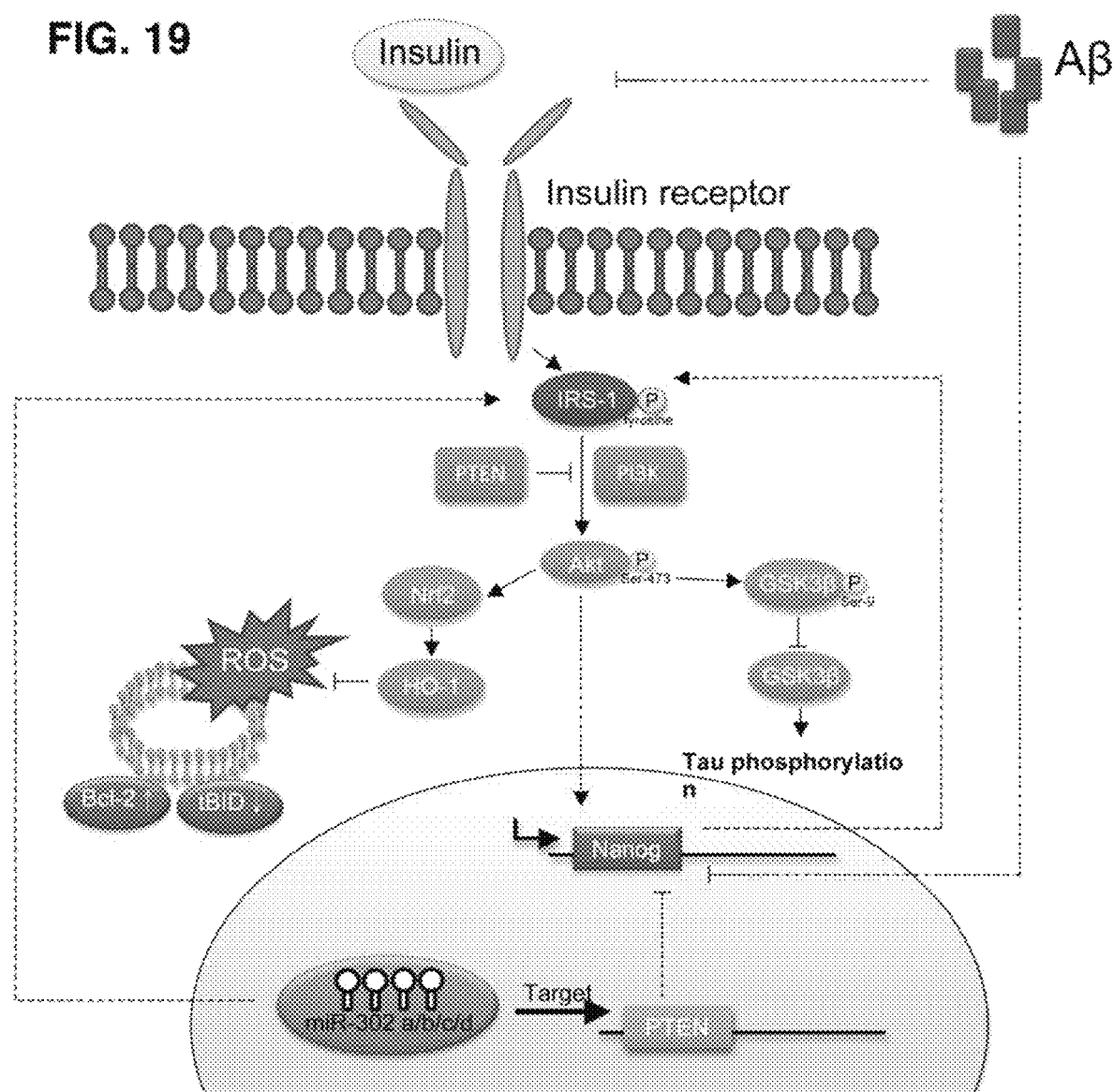

FIG. 19 shows a proposed scheme for the protective effects of miR-302 against Aβ-induced neurotoxicity. Upregulation of miR-302 can silence PTEN to activate Akt signaling, which subsequent (i) stimulates Nrf2/HO-1 elevation and hence attenuates Aβ-induced oxidative stress and apoptosis, and (ii) stimulates Nanog expression to suppress p-Ser307 IRS-1 expression, resulting in a significant increase of insulin/IRS-1/Akt signaling, so as to inhibit GSK3β-mediated tau hyperphosphorylation.

FIG. 20 shows Table 1, which shows data of AD patients and age-matched healthy individuals included in this trial study of miR-302 treatments for AD therapy. The table presents gender, age, MMSE and CASI scores for AD patients and healthy individual controls, respectively.

EXAMPLES

Referring particularly to the Examples provided for the purpose of practical demonstration only and not limitation.
1. Bacterial Cell Culture and Chemical Treatments Competent cells of E. coli DH5alpha strain were acquired from the z-competent E. coli transformation kit (Zymo Research, Irvine, Calif.) and transformed by mixing with about 1~10 μg of a desired plasmid vector such as pLVX-Grn-miR302+367 and/or pLenti-EF1alpha-RGFP-miR302 vectors. Non-transformed bacterial cells were normally grown in Luria-Bertani (LB) broth supplemented with 10 mM $MgSO_4$ and 0.2 mM glucose at 37° C. with frequent agitation at 170 rpm, whereas the transformed bacterial cells were cultivated under the same condition with further addition of 100 μg/mL ampicillin. For chemical induction, about 0.1~10 mL of MOPS, glycerin, and/or ethanol, respectively or in combination, was added into per litter of LB broth supplemented with 10 mM $MgSO_4$ and 0.2 mM glucose in the presence of 100 μg/mL ampicillin. As negative controls, the transformed cells were cultivated in the same ampicillin-added LB broth but without addition of any chemical inducer.

2. Human Cell Culture and MicroRNA Transfection

For inducing stem cell derivation with miR-302, human epidermal skin cells (hpESCs) were isolated and dissociated from a minimum of 2 cubic mm by 4 mg/mL collagenase I digestion at 37° C. for 35 min in fresh RPMI 1640 medium supplemented with 20% FBS. For culturing keratinocytes, the isolated cells were cultivated in EpiLife serum-free cell culture medium supplemented with human keratinocyte growth supplements (HKGS, Invitrogen, Carlsbad, Calif.) in the absence of antibiotics at 37° C. under 5% $CO_2$. Culture cells were passaged at 50%-60% confluency by exposing cells to trypsin/EDTA solution for 1 min and rinsing once with phenol red-free DMEM medium (Invitrogen), and the detached cells are replated at 1:10 dilution in fresh EpiLife medium with HKGS supplements. Human cancer/tumor cell lines MCF7, HepG2 and Tera-2 were obtained from the American Type Culture Collection (ATCC, Rockville, Md.) and maintained according to manufacturer's suggestions. For microRNA/shRNA transfection, 15 μg of isolated miR-302 and/or precursor thereof was dissolved in 1 mL of fresh EpiLife medium and mixed with 50 μL of X-tremeGENE HP DNA transfection reagent. After 10 min incubation, the mixture was added into a 100-mm cell culture dish containing 50%-60% confluency of hpESCs or the cancer/tumor cells, respectively. The medium was replaced by fresh EpiLife medium with HKGS supplements or the conditioned medium suggested by ATCC 12 to 18 hours later. This transfection procedure could be repeated 3 to 4 times every three-four days to increase transfection efficiency. After cell morphology became sphere-like, the cells (mirPSCs) were grown and passaged in knockout DMEM/F-12 medium (Invitrogen, CA) supplemented with 20% knockout serum, 1% MEM nonessential amino acids, 100 μM β-mercaptoethanol, 1 mM GlutaMax, 1 mM sodium pyruvate, 10 ng/mL bFGF, 10 ng/mL FGF-4, 5 ng/mL LIF, 100 IU/ml penicillin/100 μg/mL streptomycin, 0.1 μM A83-01, and 0.1 μM valproic acid (Stemgent, San Diego, Calif.), at 37° C. under 5% $CO_2$.

In the tests for treating AD with miR-302, human neuroblastoma SK-N-MC cells were obtained from the American Type Culture Collection (ATCC, Bethesda, Md., USA). Cells were maintained in Minimal Eagle's medium (MEM, Gibco), supplemented with 10% fetal bovine serum, 100 units/mL penicillin, 100 μg/mL streptomycin, and 2 mM L-glutamine at 37° C., 5% CO2. For inducing miR-302 expression, a pLVX-Grn-miR-302 vector was applied to transfect the SK-N-MC cells, using a lipofectamine 2000 reagent (Invitrogen) following the manufacturer's instructions, so as to form miR-302-transfected cells. The miR-302-transfected cells were identified by the presence of a co-expressed AcGFP green fluorescent protein. For silencing Nanog expression, another shRNA gene silencer vector directed against human Nanog mRNAs, called shRNA-Nanog, was obtained from Academia Sinica in Taiwan. In some experiments, we further transfected the shRNA-Nanog vector into the miR-302-transfected cells with the lipofectamine 2000 reagent.

3. Protein Extraction and Western Blot Analysis

Cells ($10^6$) are lysed with a CelLytic-M lysis/extraction reagent (Sigma) supplemented with protease inhibitors, Leupeptin, TLCK, TAME and PMSF, following the manufacturer's suggestion. Lysates are centrifuged at 12,000 rpm for 20 min at 4° C. and the supernatant is recovered. Protein concentrations are measured using an improved SOFTmax protein assay package on an E-max microplate reader (Molecular Devices, CA). Each 30 μg of cell lysate are added to SDS-PAGE sample buffer under reducing (+50 mM DTT) and non-reducing (no DTT) conditions, and boiled for 3 min before loading onto a 6~8% polyacylamide gel. Proteins are resolved by SDS-polyacrylamide gel electrophoresis (PAGE), electroblotted onto a nitrocellulose membrane and incubated in Odyssey blocking reagent (Li-Cor Biosciences, Lincoln, Nebr.) for 2 hours at room temperature. Then, a primary antibody is applied to the reagent and incubated the mixture at 4° C. Primary antibodies include Oct3/4 (Santa Cruz Biotechnology, Santa Cruz, Calif.), Sox2 (Santa Cruz), Nanog (Santa Cruz), CDK2 (Santa Cruz), cyclin D1 (Santa Cruz), cyclin D2 (Abcam), BMI-1 (Santa Cruz), keratin 16 (Abcam), β-actin (Chemicon, Temecula, Calif.), RuvB (Santa Cruz) and RGFP (Clontech). After overnight, the membrane is rinsed three times with TB S-T and then exposed to goat anti-mouse IgG conjugated secondary antibody to Alexa Fluor 680 reactive dye (1:2,000; Invitrogen-Molecular Probes), for 1 hour at the room temperature. After three additional TBS-T rinses, fluorescent scanning of the immunoblot and image analysis are conducted using Li-Cor Odyssey Infrared Imager and Odyssey Software v.10 (Li-Cor).

4. RNA Extraction and Northern Blot Analysis

Total RNAs (10 μg) are isolated with a mirVana™ miRNA isolation kit (Ambion, Austin, Tex.), fractionated by either 15% TBE-urea polyacrylamide gel or 3.5% low melting point agarose gel electrophoresis, and electroblotted onto a nylon membrane. Detection of miR-302 and/or pre-miR-302 is performed with a [LNA]-DNA probe (5'-[TCACTGAAAC] ATGGAAGCAC TTA-3') (SEQ-.ID.NO.1) probe. The probe has been purified by high-performance liquid chromatography (HPLC) and tail-labeled with terminal transferase (20 units) for 20 min in the presence of [$^{32}$P]-dATP (>3000 Ci/mM, Amersham International, Arlington Heights, Ill.).

5. Plasmid Amplification and Plasmid DNA/Total RNA Extraction

Competent E. coli DH5alpha cells treated with plasmid transformation (from Example 1) are cultivated overnight in LB broth supplemented with 10 mM $MgSO_4$ and 0.2 mM glucose at 37° C. with frequent agitation at 170 rpm. For inducing eukaryotic promoter-driven RNA and/or protein production, 0.5 to 2 ml of MOPS, glycerin, and/or ethanol is added into every 1 litter of LB broth for the above bacterial cultivation and amplification. All amplified plasmid DNAs and expressed mRNAs/microRNAs are isolated together using a HiSpeed plasmid purification kit (Qiagen, Valencia, Calif.), following the manufacturer's protocol but with a minor modification that RNase A is not added into the P1 buffer. The final extracted products containing both plasmids and mRNAs/microRNAs are dissolved in DEPC-treated dd$H_2O$ and stored at −80° C. before use. For purifying only the amplified plasmid vectors, RNase A is added into the P1 buffer and the extraction procedure is performed following the manufacturer's protocol.

6. MicroRNA and mRNA Isolation/Purification

Total RNAs isolated from the above Example 5 are further purified using a mirVana™ miRNA isolation kit (Ambion, Austin, Tex.), following the manufacturer's protocol. The final products are dissolved in DEPC-treated ddH$_2$O and stored at −80° C. before use. Because bacterial RNAs are degraded very fast (a few hours) in nature while eukaryotic poly-A RNAs (mRNAs) and hairpin-like microRNA precursors (pre-miRNA or pri-miRNA) remain relatively stable at 4° C. (half-life up to 3-4 days), we can use this difference to acquire pure mRNAs and/or pre-miRNAs for further applications. For example, RGFP mRNA can be used to identify the transfected cells, while pre-miR-302s are used to reprogram somatic cells to ESC-like iPS cells. The purified pre-miR-302s can also be added into stem cell culture medium to facilitate and maintain the reprogramming process.

7. Immunostaining Assay

Embedding, sectioning and immunostaining tissue samples are performed as reported (Lin et al., RNA 2008). Primary antibodies include Oct4 (Santa Cruz), Sox2 (Santa Cruz), Nanog (Santa Cruz), and RGFP (Clontech). Fluorescent dye-labeled goat anti-rabbit or horse anti-mouse antibody is used as the secondary antibody (Invitrogen-Molecular Probes). Positive results are examined and analyzed at 100× or 200× magnification under a fluorescent 80i microscopic quantitation system with a Metamorph imaging program (Nikon).

8. Bisulfite DNA Sequencing

Genomic DNAs are isolated from about two million cells using a DNA isolation kit (Roche, Indianapolis, Ind.) and 1 μg of the isolated DNAs are further treated with bisulfite (CpGenome DNA modification kit, Chemicon, Temecula, Calif.), according to the manufacturers' suggestions. The treatment with bisulfite converts all unmethylated cytosine to uracil, while methylated cytosine remains as cytosine. For bisulfite DNA sequencing analyses, we amplify the promoter regions of Oct4 and Nanog with PCR. Primers include 5'-GAGGCTGGAG CAGAAGGATT GCTTTGG-3' (SEQ.ID.NO.2) and 5'-CCCTCCTGAC CCATCACCTC CAC-CACC-3' (SEQ.ID.NO.3) for Oct4, and 5'-TGGTTAGGTT GGTTTTAAAT TTTTG-3' (SEQ.ID.NO.4) and 5'-AAC-CCACCCT TATAAATTCT CAATTA-3' (SEQ.ID.NO.5) for Nanog. The bisulfite-modified DNAs (50 ng) are first mixed with the primers (total 100 pmole) in 1× PCR buffer, heated to 94° C. for 2 min, and immediately cooled on ice. Next, 25 cycles of PCR are performed as follows: 94° C. for 1 min and 70° C. for 3 min, using an Expand High Fidelity PCR kit (Roche). The amplified DNA product with a correct size is further fractionized by 3% agarose gel electrophoresis, purified with a gel extraction filter (Qiagen), and then used in DNA sequencing. A detailed profile of the DNA methylation sites is then generated by comparing the unchanged cytosine in the converted DNA sequence to the unconverted one.

9. Materials and Preparations 3-(4,5-dimethylthiazol-2-yl)-2,5-diphenyltetrazolium bromide (MTT), 4',6-diamidino-2-phenylindole (DAPI), dihydroethidium (DHE), and JC-1 were purchased from Sigma (Munchen, Germany). Amyloid-β (Aβ) 1-42 was acquired from AnaSpec Inc. (San Jose, Calif., USA), and solutions were prepared according to our previous report (Li et al, 2015). Antibodies used were directed against Akt, p-Akt, GSK3β, p-GSK3β, IRS-1, Nrf2, HO-1, tBid, Bcl-2, Caspase 3, poly (ADP-ribose) polymerase (PARP) (from Santa Cruz, Calif., USA), p-tyrosine, p-Tau, Tau (from Merck Millipore, Darmstadt, Germany), β-actin (from Novus Biologicals, Littleton, Colo., USA), p-IRS-1, Nanog, and PTEN (from Cell Signaling Technology, Danvers, Mass., USA), respectively.

10. Cell Viability Assays

Cells were seeded in 24-well plates overnight and then treated as indicated. After 24 hours, the tetrazolium salt MTT was added to the medium following the manufacturer's instructions. Only viable cells could metabolize MTT into a purple formazan product, of which the color density (OD) was further quantified by a Bio-Rad spectrophotometer at 550 nm. Cell viability was determined by the percentage of OD from treated cells or transfected cells divided by OD from control cells.

11. Examination of Nucleus Morphology

Cells were cultivated on coated slides at 60% confluency and then treated with drugs for 24 hours. Thereafter, changes in cell nucleus morphology, in particular characteristics of apoptosis, were examined, using a fluorescence microscope. The cells were fixed in 4% paraformaldehyde after 24 hours of treatment with the indicated compounds, permeabilized in ice-cold methanol, incubated with 1 ng/mL of DAPI stain for 15 min at room temperature, and then observed under a fluorescence microscope (DP80/BX53, Olympus). Apoptotic cells were quantified by counting four random fields per condition of treatment.

12. Analysis of Mitochondrial Membrane Potential (MMP)

MMP was investigated using a vital mitochondrial cationic dye JC-1, which accumulates in mitochondria in a potential-dependent matter. Cells were treated with 1 μM of JC-1 in fresh medium and incubated at 37° C. for 30 min. Cell morphology was then observed and photographed using an inverted fluorescence microscope (DP72/CKX41, Olympus). In normal cells, JC-1 remained as red fluorescent aggregations, whereas during the induction of apoptosis the mitochondrial potential collapsed and hence JC-1 formed monomers producing green fluorescence. MMP was quantified by fluorescent intensity using Image J software (NIH, Bethesda, Md.). Then, the normalized fluorescence intensity levels from control cells were set as 100% for comparing the relative expression levels of the fluorescent intensities in tested groups.

13. Detection of ROS by Dihydroethidium (DHE) Staining

DHE is a fluorogenic reagent used for detecting intracellular superoxide radical anion. Cells were treated in fresh medium containing 10 μM DHE and incubated for 30 min in the dark at room temperature. After 30-min incubation, the staining medium was discarded and the cells were washed twice with PBS and then observed and photographed under an inverted fluorescence microscope (DP72/CKX41). ROS levels were determined by oxidized DHE fluorescence intensity using Image J software (NIH, Bethesda, Md.). Then, the normalized fluorescence intensity levels from control cells were set as 100% for comparing the relative expression levels of the fluorescent intensities in tested groups.

14. Study Population and Blood Sample

Blood sampling from AD patients (n=7) and age-matched healthy individuals (n=6) was performed according to standardized procedures approved by the Institutional Review Board (IRB) of Chung Shan Medical University Hospital (CSMUH No: CS 13233) (Table 1). Clinical AD diagnosis was determined by the Diagnostic and Statistical Manual of Mental Disorders IV (DSM-IV) criteria and completed with a Mini-Mental State Examination (MMSE) and cognitive abilities screening instrument (CASI) test. MMSE scores were used as a rough measurement of cognitive function. CASI scores ranged from 1 to 100 were used for quantitative assessment on attention, concentration, orientation, short-term memory, long-term memory, language abilities, visual construction, list-generating fluency, abstraction, and judgment. A detailed overview of AD patients (n=7, mean age 80.0±4.9 years, range 74-86 years) and age-matched healthy individuals (n=6, mean age 80.0±5.9 years, range 72-86 years) was summarized in Table 1. A number of AD patients (n=7, Female/Male=4/3) had moderate dementia under MMSE (mean scale=19.3±2.6, range 16-23) and CASI (mean scale=65.1±10.3, range 49-79) measurement scales, showing most differences between AD patients and age-matched healthy controls (n=6, Female/Male=3/3) (Table. 1). Age-matched healthy individuals were recruited by local advertisement at the Aging Research Unit, Chung Shan Medical University, Taichung, Taiwan. Neither cognitive impairment nor any dementia disorder was detected in all tested healthy individuals. Both AD patients and age-matched healthy individuals were volunteers with written informed consents had been obtained from all participants and/or their closest relatives according to the Declaration of Helsinki and the IRB-approved protocols. Approximately 20 mL of venous peripheral blood mononucleated cells (PBMCs) were obtained from each tested subject and then total RNAs were isolated from each blood sample with an Oiagen RNeasy Kit (Qiagen, Germantown, Md., USA) and further used for spectrophotometric quantification following the manufacturer's instructions.

15. Reverse Transcription (RT) and Quantitative PCR (qPCR)

Total RNAs were extracted from patients' PBMCs and cells, respectively, using a Qiagen RNeasy Kit (Qiagen) and further quantified spectrophotometrically. RT-qPCR was carried out using 1 µg of total RNAs and following the protocols of an ABI High-Capacity cDNA Archive Kit (ABI). Then, we diluted the resulting cDNA into ten folds and used only 5 µl of the diluted cDNA in each of triplicate qPCRs run on a Applied Biosystems 7300 Real Time PCR System with Maxima SYBR Green qPCR Master Mix (2×), ROX solution provided (Thermo), according to the manufacturer's instructions. Levels of relative mRNA or miRNA expression were acquired with the SDS software version 1.2.3 (Sequence Detection Systems 1.2.3-7300 Real Time PCR System, Applied Biosystems) and then further normalized with the level of housekeeping GAPDH expression in the same sample. The normalized mRNA levels from control cells or normal healthy individuals were set as 100% for comparing the relative expression levels of the mRNA expression in tested groups.

16. Statistic Analysis

Each experiment was repeated at least for three times (n>3). All data were presented as means±standard error of mean (S.E.M). For cell viability tests, the average population number of control cells was set as 100% for comparing the survival rates of other tested cells. For western blotting, the protein level measured in each blot was first normalized with the expression level of a housekeeping β-actin protein, and then compared to the normalized level of the protein expressed in control cells, of which the control protein level was then set as 100% for further comparison. For RT-qPCR, the measured values of mRNA expression were first normalized with the expression level of housekeeping GAPDH, and then compared to the normalized mRNA levels from control cells or normal healthy individuals, of which the control mRNA levels were set as 100% for comparing the relative expression levels of the mRNA in tested groups. For measuring fluorescence intensity, the normalized fluorescence intensity levels from control cells were set as 100% for comparing the relative expression levels of the fluorescent intensities in tested groups. Statistical significance of differences between compared groups was determined by one-way analysis of variance (ANOVA) following Dunnett's post-hoc test for multiple comparisons with a SPSS statistical software (SPSS, Inc., Chicago, Ill., USA) as well as the two-tailed Student's t-test. A probability value of <0.05 or <0.01 was taken to indicate statistical significance and hence the significant levels were set at *p<0.05 or **p<0.01, respectively, depending on individual experiments. Probability values of p<0.05 is considered significant. All p values are determined from two-tailed tests.

REFERENCES

1. Lin S L, Chang D, Chang-Lin S, Lin C H, Wu D T S, Chen D T, and Ying S Y. (2008) Mir-302 reprograms human skin cancer cells into a pluripotent ES-cell-like state. *RNA* 14, 2115-2124.
2. Lin S L and Ying S Y. (2008) Role of mir-302 microRNA family in stem cell pluripotency and renewal. Ying S Y. (Ed.) *Current Perspectives in MicroRNAs*. Springer Publishers press, New York, pp 167-185.
3. Lin S L, Chang D, Ying S Y, Leu D and Wu D T S. (2010) MicroRNA miR-302 inhibits the tumorigenecity of human pluripotent stem cells by coordinate suppression of CDK2 and CDK4/6 cell cycle pathways. *Cancer Res.* 70, 9473-9482.
4. Lin S L, Chang D, Lin C H, Ying S Y, Leu D and Wu D T S. (2011) Regulation of somatic cell reprogramming through inducible mir-302 expression. *Nucleic Acids Res.* 39, 1054-1065.
5. Lin, S. L. (2011) Deciphering the mechanism behind induced pluripotent stem cell generation. Stem Cells, 29, 1645-1649.
6. Lin, S. L. and Ying, S. Y. (2012) Mechanism and method for generating tumor-free iPS cells using intronic microRNA miR302 induction. Shao-Yao Ying (Ed.) MicroRNA Protocols, 2nd Ed. pp 295-324, Springer Publishers press, New York.
7. Lin, S. L. and Chen, J. (2013) Mechanism of miR-302-mediated iPS cell generation. Sell S (Ed.) Stem Cells Handbook. pp 119-127, Springer Publishers press, New York.
8. Chen, S. K. J. and Lin, S. L. (2013) Recent patents on microRNA-induced pluripotent stem cell generation. Recent Patents on Regenerative Medicine, 3, 5-16.
9. McDowell et al., (1994) Determination of intrinsic transcription termination efficiency by RNA polymerase elongation rate. *Science* 266, 822-825.
10. Cholerton B, Baker L D, and Craft S. (2011) Insulin resistance and pathological brain ageing. *Diabet Med.* 28, 1463-1475.
11. Spielman L J, Little J P, and Klegeris A. (2014) Inflammation and insulin/IGF-1 resistance as the possible link between obesity and neurodegeneration. *J Neuroimmunol* 273, 8-21.
12. Williamson R, McNeilly A, and Sutherland C. (2012) Insulin resistance in the brain: an old-age or new-age problem? *Biochem Pharmacol* 84, 737-745.
13. Butterfield D A. (2002) Amyloid beta-peptide (1-42)-induced oxidative stress and neurotoxicity: implications for neurodegeneration in Alzheimer's disease brain. A review. *Free Radic Res* 36, 1307-1313.
14. Li H H, Lu F J, Hung H C, Liu G Y, Lai T J, and Lin C L. (2015) Humic Acid Increases Amyloid beta-Induced Cytotoxicity by Induction of ER Stress in Human SK-N-MC Neuronal Cells. *Int J Mol Sci* 16, 10426-10442.

15. Lesne S E, Sherman M A, Grant M, Kuskowski M, Schneider J A, Bennett D A, and Ashe K H. (2013) Brain amyloid-beta oligomers in ageing and Alzheimer's disease. *Brain* 136, 1383-1398.
16. Kornelius E, Lin C L, Chang H H, Li H H, Huang W N, Yang Y S, Lu Y L, Peng C H, and Huang C N. (2015) DPP-4 Inhibitor Linagliptin Attenuates Abeta-induced Cytotoxicity through Activation of AMPK in Neuronal Cells. CNS *Neurosci Ther* 21, 549-557.
17. Hernandez F, Lucas J J, and Avila J. (2013) GSK3 and tau: two convergence points in Alzheimer's disease. *J Alzheimers Dis.* 33 Suppl 1, S141-144.
18. Bhat N R and Thirumangalakudi L. (2013) Increased tau phosphorylation and impaired brain insulin/IGF signaling in mice fed a high fat/high cholesterol diet. *J Alzheimers Dis.* 36, 781-789.
19. Majewski N, Nogueira V, Robey R B, and Hay N. (2004) Akt inhibits apoptosis downstream of BID cleavage via a glucose-dependent mechanism involving mitochondrial hexokinases. *Mol Cell Biol.* 24, 730-740.
20. Surh Y J, Kundu J K, and Na H K. (2008) Nrf2 as a master redox switch in turning on the cellular signaling involved in the induction of cytoprotective genes by some chemopreventive phytochemicals. *Planta Med.* 74, 1526-1539.
21. Kwon S H, Ma S X, Hwang J Y, Lee S Y, and Jong C G. (2015) Involvement of the Nrf2/HO-1 signaling pathway in sulfuretin-induced protection against amyloid beta neurotoxicity. *Neuroscience* 304, 14-28.
22. Alva J A, Lee G E, Escobar E E, and Pyle A D. (2011) Phosphatase and tensin homolog regulates the pluripotent state and lineage fate choice in human embryonic stem cells. *Stem Cells* 29, 1952-1962.
23. Kuijk E W, van Mil A, Brinkhof B, Penning L C, Colenbrander B, and Roelen B A. (2010) PTEN and TRP53 independently suppress Nanog expression in spermatogonial stem cells. *Stem Cells Dev* 19, 979-988.
24. Han J, Mistriotis P, Lei P, Wang D, Liu S, and Andreadis S T. (2012) Nanog reverses the effects of organismal aging on mesenchymal stem cell proliferation and myogenic differentiation potential. *Stem Cells* 30, 2746-2759.
25. Houbaviy et al. (2003) *Developmental Cell* 5, 351-358, Tablet 1.
26. Simonsson S and Gurdon J. (2004) DNA demethylation is necessary for the epigenetic reprogramming of somatic cell nuclei. *Nat Cell Biol.* 6, 984-990.
27. European Patent No. 2198025 to Lin.
28. U.S. patent application Ser. No. 12/149,725 to Lin.
29. U.S. patent application Ser. No. 12/318,806 to Lin.
30. U.S. patent application Ser. No. 12/792,413 to Lin.
31. U.S. Pat. No. 5,464,758 to Gossen.
32. U.S. Pat. No. 7,959,926 to Buechler.
33. U.S. Pat. No. 7,968,311 to Mehta.
34. PCT publication No. WO 2005/056797 to Kim.

The invention claimed is:

1. A method of protecting living human brain neurons from Aβ-induced neurotoxicity with hairpin-like RNA mimics of microRNA precursor (hairpin-like pre-miRNA mimics), comprising:
   (a) treating and transfecting at least one living neuron with a vector in vitro, wherein the vector contains SEQ.ID.NO.2 and a eukaryotic promoter, and is capable of expressing at least one hairpin-like pre-miRNA mimic through the eukaryotic promoter; and
   (b) expressing said at least one hairpin-like pre-miRNA mimic in the treated neurons.

2. The method as defined in claim 1, wherein said hairpin-like pre-miRNA mimics are miR-302 precursors (pre-miR-302) in a structural conformation selected from the group consisting of microRNA (miRNA), small hairpin RNA (shRNA), small interfering RNA (siRNA), their precursors and homologs, and a combination thereof.

3. The method as defined in claim 1, wherein said hairpin-like pre-miRNA mimics consist of SEQ.ID.NO3, SEQ.ID.NO4, SEQ.ID.NO5, and SEQ.ID.NO6.

4. The method as defined in claim 1, wherein said vector is pLenti-EF1alpha/CMV-RGFP/GFP-miR302.

5. The method as defined in claim 1, wherein the expression of said hairpin-like pre-miRNA mimics produces miR-302a, miR-302b, miR-302c and miR-302d in the treated neurons.

6. The method as defined in claim 1, further comprising a step of inducing Akt signaling activation.

7. The method as defined in claim 6, wherein said Akt signaling activation improves insulin resistance in the treated neurons.

8. The method as defined in claim 7, further comprising a step of suppressing p-307 IRS-1 serine phosphorylation, increasing IRS-1 tyrosine phosphorylation, or both.

9. The method as defined in claim 6, wherein said Akt signaling activation further stimulates Nanog expression to increase sensitivity of insulin signaling.

10. The method as defined in claim 1, further comprising a step of inducing Nrf2/HO-1 expression to reduce Aβ-induced intracellular ROS accumulation and apoptosis.

11. The method as defined in claim 1, wherein said vector is formulated with glycylglycerin for being delivered into the treated neurons.

12. The method as defined in claim 1, wherein said vector is useful for developing drugs and therapies for treating Alzheimer's diseases.

13. The method as defined in claim 1, wherein said hairpin-like pre-miRNA mimics are useful for developing drugs and therapies for treating Diabetes and Alzheimer's diseases.

14. A method of inducing Akt signaling activation in living human brain neurons by silencing at least one gene, comprising:
 (a) treating and transfecting at least one living neuron with a vector in vitro, wherein the vector contains SEQ.ID.NO.2 and a eukaryotic promoter, and is capable of expressing at least one hairpin-like pre-miRNA mimic through the eukaryotic promoter; and
 (b) expressing said at least one hairpin-like pre-miRNA mimic in the treated neurons.

15. The method as defined in claim 14, wherein said at least one gene includes PTEN gene.

* * * * *

SEQUENCE LISTING

```
<160> NUMBER OF SEQ ID NOS: 6

<210> SEQ ID NO 1
<211> LENGTH: 17
<212> TYPE: RNA
<213> ORGANISM: Artificial Sequence
<220> FEATURE:
<223> OTHER INFORMATION: chemical synthesis

<400> SEQUENCE: 1
uaagugcuuc cauguuu                                                      17

<210> SEQ ID NO 2
<211> LENGTH: 720
<212> TYPE: RNA
<213> ORGANISM: Artificial Sequence
<220> FEATURE:
<223> OTHER INFORMATION: chemical synthesis

<400> SEQUENCE: 2
aauuuuuuuc uucuaaaguu augccauuuu guuuucuuuc uccucagcuc uaaauacucu        60
gaaguccaaa gaaguuguau guugggugg cucccuucaa cuuuaacaug gaagugcuuu       120
cugugacuuu aaaaguaagu gcuuccaugu uuuaguagga gugaauccaa uuuacuucuc      180
caaaauagaa cacgcuaacc ucauuugaag ggaucccuu ugcuuuaaca uggggguacc       240
ugcuguguga aacaaaagua agugcuucca uguuucagug gaggugucuc caagccagca      300
caccuuuugu uacaaaauuu uuuguuauu guguuuuaag guuacuaagc uuguuacagg       360
uuaaaggauu cuaacuuuuu ccaagacugg gcuccccacc acuuaaacgu ggauguacuu      420
gcuuugaaac uaaagaagua agugcuucca uguuugggug augguaaguc uucuuuuuac      480
auuuuuauua uuuuuuuaga aaauaacuuu auuguauuga ccgcagcuca uauauuuaag      540
cuuuauuuug uauuuuuaca ucuguuaagg ggcccccucu acuuuaacau ggaggcacuu      600
```

```
gcugugacau gacaaaaaua agugcuucca uguuugagug uggugguucc uaccuaauca        660
gcaauugagu uaacgcccac acugugugca guucuuggcu acaggccauu acuguugcua        720

<210> SEQ ID NO 3
<211> LENGTH: 69
<212> TYPE: RNA
<213> ORGANISM: Artificial Sequence
<220> FEATURE:
<223> OTHER INFORMATION: chemical synthesis

<400> SEQUENCE: 3
ccaccacuua aacguggaug uacuugcuuu gaaacuaaag aaguaagugc uuccauguuu        60
uggugaugg                                                               69

<210> SEQ ID NO 4
<211> LENGTH: 73
<212> TYPE: RNA
<213> ORGANISM: Artificial Sequence
<220> FEATURE:
<223> OTHER INFORMATION: chemical synthesis

<400> SEQUENCE: 4
gcucccuuca acuuuaacau ggaagugcuu ucgugacuu uaaaaguaag ugcuuccaug         60
uuuuaguagg agu                                                          73

<210> SEQ ID NO 5
<211> LENGTH: 68
<212> TYPE: RNA
<213> ORGANISM: Artificial Sequence
<220> FEATURE:
<223> OTHER INFORMATION: chemical synthesis

<400> SEQUENCE: 5
ccuuugcuuu aacauggggg uaccugcugu gugaaacaaa aguaagugcu uccauguuuc        60
aguggagg                                                                68

<210> SEQ ID NO 6
<211> LENGTH: 68
<212> TYPE: RNA
<213> ORGANISM: Artificial Sequence
<220> FEATURE:
<223> OTHER INFORMATION: chemical synthesis

<400> SEQUENCE: 6
ccucuacuuu aacauggagg cacuugcugu gacaugacaa aaauaagugc uuccauguuu        60
gagugugg                                                                68
```